US009630997B2

(12) United States Patent
Hughes et al.

(10) Patent No.: US 9,630,997 B2
(45) Date of Patent: Apr. 25, 2017

(54) COMPOSITIONS AND METHODS FOR PEPTIDE EXPRESSION AND PURIFICATION USING A TYPE III SECRETION SYSTEM

(71) Applicant: UNIVERSITY OF UTAH RESEARCH FOUNDATION, Salt Lake City, UT (US)

(72) Inventors: Kelly T. Hughes, Salt Lake City, UT (US); Baldomero M. Olivera, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 14/404,919

(22) PCT Filed: May 30, 2013

(86) PCT No.: PCT/US2013/043384
§ 371 (c)(1),
(2) Date: Dec. 1, 2014

(87) PCT Pub. No.: WO2013/181404
PCT Pub. Date: Dec. 5, 2013

(65) Prior Publication Data
US 2015/0225466 A1 Aug. 13, 2015

Related U.S. Application Data

(60) Provisional application No. 61/689,284, filed on May 30, 2012.

(51) Int. Cl.
| | |
|---|---|
| *C07K 14/245* | (2006.01) |
| *C12N 15/74* | (2006.01) |
| *C07K 14/255* | (2006.01) |
| *C07K 14/34* | (2006.01) |
| *C07K 14/435* | (2006.01) |
| *C07K 14/46* | (2006.01) |
| *C12P 21/02* | (2006.01) |
| *C12N 15/62* | (2006.01) |
| *C12N 15/70* | (2006.01) |

(52) U.S. Cl.
CPC .......... *C07K 14/245* (2013.01); *C07K 14/255* (2013.01); *C07K 14/34* (2013.01); *C07K 14/43504* (2013.01); *C07K 14/43518* (2013.01); *C07K 14/43522* (2013.01); *C07K 14/46* (2013.01); *C12N 15/62* (2013.01); *C12N 15/70* (2013.01); *C12N 15/74* (2013.01); *C12P 21/02* (2013.01); *C07K 2319/036* (2013.01); *C07K 2319/21* (2013.01); *C07K 2319/50* (2013.01)

(58) Field of Classification Search
None
See application file for complete search history.

(56) References Cited

U.S. PATENT DOCUMENTS

| | | | | |
|---|---|---|---|---|
| 2005/0064549 A1* | 3/2005 | Aparicio | C07K 14/705 | 435/69.1 |
| 2005/0176000 A1* | 8/2005 | Callen | C12N 9/2417 | 435/6.19 |
| 2012/0027786 A1* | 2/2012 | Gupta | C07K 14/21 | 424/184.1 |

OTHER PUBLICATIONS

Zhang, "Fusion to FlgM Allows Secretion and Purification of Conotoxin Protein Through the Flagellar Type III Secretion system", Master of Science Thesis, University of Utah, 2008.*
Uhlen, Biotechniques 44:649-654, 2008.*
Honda et al. Appl. Microbiol. Biotechnol. 40:341=347, 1993.*
Abramoff, M.D., et al., "Image Processing with ImageJ," Biophotonics International 11(7):36-42, Laurin Publishing Co. Inc., United States (2004).
Aldridge, C., et al., "The Interaction Dynamics of a Negative Feedback Loop Regulates Flagellar Number in *Salmonella enterica* Serovar Typhimurium," Molecular Microbiology 78(6):1416-1430, Blackwell Scientific Publications, England (2010).
Aldridge, P.D., et al., "The Flagellar-specific Transcription Factor, $\sigma^{28}$, is the Type III Secretion Chaperone for the Flagellar-specific Anti-$\sigma^{28}$ Factor FlgM," Genes and Development 20(16):2315-2326, Cold Spring Harbor Laboratory Press, United States (2006).
Auvray, F., et al., "Flagellin Polymerisation Control by a Cytosolic Export Chaperone," Journal of Molecular Biology 308(2):221-229, Elsevier, England (2001).
Baneyx, F. and Georgiou, G., "In Vivo Degradation of Secreted Fusion Proteins by the *Escherichia coli* Outer Membrane Protease OmpT," Journal of Bacteriology 172(1):491-494, American Society for Microbiology, United States (1990).
Barembruch, C. and Hengge, R., "Cellular Levels and Activity of the Flagellar Sigma Factor FliA of *Escherichia coli* are Controlled by FlgM-modulated Proteolysis," Molecular Microbiology 65(1):76-89, Blackwell Scientific Publications, England (2007).
Berg, H.C. and Anderson, R.A., "Bacteria Swim by Rotating their Flagellar Filaments," Nature 245(5425):380-382, Nature Publishing Group, England (1973).
Bonifield, H.R. and Hughes, K.T., "Flagellar Phase Variation in *Salmonella enterica* Is Mediated by a Posttranscriptional Control Mechanism," Journal of Bacteriology 185(12):3567-3574, American Society for Microbiology, United States (2003).
Bulaj, G., et al., "Novel Conotoxins from *Conus striatus* and *Conus kinoshitai* Selectively Block TTX-resistant Sodium Channels," Biochemistry 44(19):7259-7265, American Chemical Society, United States (2005).
Chadsey, M.S. and Hughes, K.T., "A Multipartite Interaction Between *Salmonella* Transcription Factor $\sigma^{28}$ and its Anti-$\sigma$ Factor FlgM: Implications for $\sigma^{28}$ Holoenzyme Destabilization through Stepwise Binding," Journal of Molecular Biology 306(5):915-929, Elsevier, England (2001).

(Continued)

*Primary Examiner* — Nancy Treptow

(74) *Attorney, Agent, or Firm* — Sterne, Kessler, Goldstein & Fox P.L.L.C.

(57) ABSTRACT

Disclosed are compositions and methods for expressing and purifying a peptide of interest using a Flagellar Type III secretion system. Disclosed are nucleic acid sequences that contain a FlgM nucleic acid sequence, a cleavage site, and a nucleic acid sequence of interest. Also disclosed are polypeptides that contain FlgM, a cleavage site and a peptide of interest. Methods of producing polypeptides that have FlgM, a cleavage site and a peptide of interest are provided.

30 Claims, 27 Drawing Sheets

(56) References Cited

OTHER PUBLICATIONS

Chadsey, M.S., et al., "The Flagellar Anti-σ Factor FlgM Actively Dissociates *Salmonella typhimurium* σ$^{28}$ RNA Polymerase Holoenzyme," Genes and Development 12(19):3123-3136, Cold Spring Harbor Laboratory Press, United States (1998).
Chahine, M., et al., "Characterizing the μ-conotoxin Binding Site on Voltage-sensitive Sodium Channels with Toxin Analogs and Channel Mutations," Receptors and Channels 3(3):161-174, Taylor and Francis, England (1995).
Chahine, M., et al., "Extrapore Residues of the S5-S6 Loop of Domain 2 of the Voltage-gated Skeletal Muscle Sodium Channel (rSkM1) Contribute to the μ-conotoxin GIIIA Binding Site," Biophysical Journal 75(1):236-246, Cell Press, United States (1998).
Chang, N.S., et al., "Predominant Interactions Between μ-conotoxin Arg-13 and the Skeletal Muscle Na$^+$ Channel Localized by Mutant Cycle Analysis," Biochemistry 37(13):4407-4419, American Chemical Society, United States (1998).
Che, N., et al., "Soluble Expression and One-step Purification of a Neurotoxin Huwentoxin-I in *Escherichia coli*," Protein Expression and Purification 65(12):154-159, Academic Press, United States (2009).
Chevance, F.F. and Hughes, K.T., "Coordinating Assembly of a Bacterial Macromolecular Machine," Nature Reviews. Microbiology 6(6):455-465, Nature Publishing Group, England (2008).
Chubiz, J.E., et al., "FliZ Regulates Expression of the *Salmonella* Pathogenicity Island 1 Invasion Locus by Controlling HilD Protein Activity in *Salmonella enterica* Serovar Typhimurium," Journal of Bacteriology 192(23):6261-6270, American Society for Microbiology, United States (2010).
Datsenko, K.A. and Wanner, B.L., "One-Step Inactivation of Chromosomal Genes in *Escherichia coli* K-12 Using PCR Products," Proceedings of the National Academy of Sciences of the United States of America 97(12):6640-6645, National Academy of Sciences, United States (2000).
Daughdrill, G.W., et al., "The C-terminal Half of the Anti-sigma Factor, FlgM, Becomes Structured When Bound to its Target, σ$^{28}$," Nature Structural Biology 4(4):285-291, Nature Publishing Group, United States (1997).
Dobo, J., et al., "Application of a Short, Disordered N-terminal Flagellin Segment, A Fully Functional Flagellar Type III Export Signal, to Expression of Secreted Proteins," Applied and Environmental Microbiology 76(3):891-889, American Society for Microbiology, United Staes (2010).
Dorel, C., et al., "The Cpx System of *Escherichia coli*, A Strategic Signaling Pathway for Confronting Adverse Conditions and for Settling Biofilm Communities?," Research in Microbiology 157(4):306-314, Elsevier, France (2006).
Dudley, S.C., et al., "A μ-conotoxin-insensitive Na$^+$ Channel Mutant: Possible Localization of a Binding Site at the Outer Vestibule," Biophysical Journal 69(5):1657-1665, Cell Press, United States (1995).
Ellermeier, C.D. and Slauch, J.M., "RtsA and RtsB Coordinately Regulate Expression of the Invasion and Flagellar Genes in *Salmonella enterica* Serovar Typhimurium," Journal of Bacteriology 185(17):5096-5108, American Society for Microbiology, United States (2003).
Enomoto, M. and Stocker, B.A., "Integration, at Hag or elsewhere, of H2 (Phase-2 Flagellin) Genes Transduced from *Salmonella* to *Escherichia coli*," Genetics 81(4):595-614, Genetics Society of America, United States (1975).
Erhardt, M. and Hughes, K.T., "C-ring Requirement in Flagellar Type III Secretion is Bypassed by FlhDC Upregulation," Molecular Microbiology 75(2):376-393, Blackwell Scientific Publications, England (2010).
Erhardt, M., et al., "Bacterial Nanomachines: The Flagellum and Type III Injectisome," Cold Spring Harbor Perspectives in Biology 2(11):a000299, Cold Spring Harbor Laboratory Press, United States (2010).

Fattori, J., et al., "Bacterial Secretion Chaperones," Protein and Peptide Letters 18(2):158-166, Bentham Science Publishers, Netherland (2011).
Fiedler, B., et al., "Specificity, Affinity and Efficacy of Iota-conotoxin RXIA, An Agonist of Voltage-gated Sodium Channels Na$_v$1.2, 1.6 and 1.7," Biochemical Pharmacology 75(12):2334-2344, Elsevier Science, England (2008).
Flynn, J.M., et al., "Proteomic Discovery of Cellular Substrates of the ClpXP Protease Reveals Five Classes of ClpX-recognition Signals," Molecular Cell 11(3):671-683, Cell Press, United States (2003).
Francez-Charlot, A., et al., "RcsCDB His-Asp Phosphorelay System Negatively Regulates the *flhDC* Operon in *Escherichia coli*," Molecular Microbiology 49(3):823-832, Blackwell Scientific Publications, England (2003).
Fraser, G.M., et al., "Substrate-specific Binding of Hook-associated Proteins by FlgN and FliT, Putative Chaperones for Flagellum Assembly," Molecular Microbiology 32(3):569-580, Blackwell Scientific Publications, England (1999).
Frye, J., et al., "Identification of New Flagellar Genes of *Salmonella enterica* Serovar Typhimurium," Journal of Bacteriology 188(6):2233-2243, American Society for Microbiology, United States (2006).
Galan, J.E. and Curtiss, R., "Expression of *Salmonella typhimurium* Genes Required for Invasion is Regulated by Changes in DNA Supercoiling," Infection and Immunity 58(6):1879-1885, American Society for Microbiology, United States (1990).
Gillen, K.L. and Hughes, K.T., "Molecular Characterization of *flgM*, A Gene Encoding a Negative Regulator of Flagellin Synthesis in *Salmonella typhimurium*," Journal of Bacteriology 173(20):6453-6459, American Society for Microbiology, United States (1991).
Gillen, K.L. and Hughes, K.T., "Transcription from Two Promoters and Autoregulation Contribute to the Control of Expression of the *Salmonella typhimurium* Flagellar Regulatory Gene *flgM*," Journal of Bacteriology 175(21):7006-7015, American Society for Microbiology, United States (1993).
Green, B.R., et al., "Conotoxins Containing Nonnatural Backbone Spacers: Cladistic-based Design, Chemical Synthesis, and Improved Analgesic Activity," Chemistry and Biology 14(4):399-407, Elsevier, United States (2007).
Hughes, K.T., et al., "Sensing Structural Intermediates in Bacterial Flagellar Assembly by Export of a Negative Regulator," Science 262(5137):1277-1280, American Association for the Advancement of Science, United States (1993).
Hughes, K.T., et al., "The *Salmonella typhimurium nadC* Gene: Sequence Determination by Use of Mud-P22 and Purification of Quinolinate Phosphoribosyltransferase," Journal of Bacteriology 175(2):479-486, American Society for Microbiology, United States (1993).
Hui, K., et al., "Electrostatic and Steric Contributions to Block of the Skeletal Muscle Sodium Channel by μ-conotoxin," Journal of General Physiology 119(1):45-54, Rockefeller University Press, United States (2002).
Ikebe, T., et al., "Structure and Expression of the *fliA* Operon of *Salmonella typhimurium*," Microbiology 145(Pt 6): 1389-1396, Kluwer Academic/Plenum Publishers, United States (1999).
International Searching Authority, International Search Report for International Application No. PCT/US13/43384, ISA/US, Alexandria, Virginia, United States, mailed Oct. 25, 2013, 4 pages.
Iyoda, S., et al., "A Flagellar Gene fliZ Regulates the Expression of Invasion Genes and Virulence Phenotype in *Salmonella enterica* Serovar Typhimurium," Microbial Pathogenesis 30(2):81-90, Academic Press, England (2001).
Jones, R.M. and Bulaj, G., "Conotoxins—New Vistas for Peptide Therapeutics," Current Pharmaceutical Design 6(12):1249-1285, Bentham Science Publishers, Netherland (2000).
Karlinsey, J.E., et al., "Completion of the Hook-basal Body Complex of the *Salmonella typhimurium* Flagellum is Coupled to FlgM Secretion and fliC Transciption," Molecular Microbiology 37(5):1220-1231, Blackwell Scientific Publications, England (2000).

(56) References Cited

OTHER PUBLICATIONS

Karlinsey, J.E., et al., "Translation/secretion Coupling by Type III Secretion Systems," Cell 102(4):487-497, Cell Press, United States (2000).

Karlinsey, J.E., "lambda-Red Genetic Engineering in Salmonella enterica Serovar typhimurium," in 421 Methods in Enzymology, Advanced Bacterial Genetics: Use of Transposons and Phage for Genomic Engineering, 199-209 (Kelly T. Hughes and Stanley R. Maloy eds., Academic Press 2007), United States.

Kutsukake, K., "Excretion of the Anti-sigma Factor through a Flagellar Substructure Couples Flagellar Gene Expression with Flagellar Assembly in Salmonella typhimurium," Molecular and General Genetics 243(6):605-612, New York Springer-Verlag, Germany (1994).

Lee, H.J. and Hughes, K.T., "Posttranscriptional Control of the Salmonella enterica Flagellar Hook Protein FlgE," Journal of Bacteriology 188(9):3308-3316, American Society for Microbiology, United States (2006).

Lehnen, D., et al., "LrhA as a New Transcriptional Key Regulator of Flagella, Motility and Chemotaxis Genes in Escherichia coli," Molecular Microbiology 45(2):521-532, Blackwell Scientific Publications, England (2002).

Lemke, J.J., et al., "DksA and ppGpp Directly Regulate Transcription of the Escherichia coli Flagellar Cascade," Molecular Microbiology 74(6):1368-1379, Blackwell Scientific Publications, England (2009).

Lucas, R.L., et al., "Multiple Factors Independently Regulate hilA and Invasion Gene Expression in Salmonella enterica Serovar Typhimurium," Journal of Bacteriology 182(7):1872-1882, American Society for Microbiology, United States (2000).

Macnab, R.M., "How Bacteria Assemble Flagella," Annual Review of Microbiology 57:77-100, Annual Reviews, United States (2003).

Macnab, R.M., "Type III Flagellar Protein Export and Flagellar Assembly," Biochimica et Biophysica Acta 1694(1-3):207-217, Elsevier, Netherlands (2004).

Merdanovic, M., et al., "Protein Quality Control in the Bacterial Periplasm," Annual Review of Microbiology 65:149-168, Annual Reviews, United States (2011).

Miljanich, G.P., "Venom Peptides as Human Pharmaceuticals," Science and Medicine 4(5):6-15, Science and Medicine, Inc., United States(1997).

Miljanich, G.P., "Ziconotide: Neuronal Calcium Channel Blocker for Treating Severe Chronic Pain," Current Medicinal Chemistry 11(23):3029-3040, Bentham Science Publishers, Netherlands (2004).

Minamino, T. and Namba, K., "Distinct Roles of the FliI ATPase and Proton Motive Force in Bacterial Flagellar Protein Export," Nature 451(7177):485-488, Nature Publishing Group, England (2008).

Nakamura, M., et al., "Modification of Arg-13 of μ-conotoxin GIIIA with Piperidinyl-Arg Analogs and their Relation to the Inhibition of Sodium Channels," FEBS Letters 503(1):107-110, Elsevier Science B.V., Netherlands (2001).

Namba, K., "Roles to Partly Unfolded Conformations in Macromolecular Self-assembly," Genes to Cells 6(1):1-12, Blackwell Scientific Publications, England (2001).

Ohnishi, K., et al., "A Novel Transcriptional Regulation Mechanism in the Flagellar Regulon of Salmonella typhimurium: An Antisigma Factor Inhibits the Activity of the Flagellum-specific Sigma Factor, σF," Molecular Microbiology 6(21):3149-3157, Blackwell Scientific Publications, England (1992).

Ohnishi, K., et al., "Gene fliA Encodes an Alternative Sigma Factor Specific for Flagellar Operons in Salmonella typhimurium," Molecular and General Genetics 221(2):139-147, New York Springer-Verlag, Germany (1990).

Olivera, B.M., "ω-Conotoxin MVIIA: From Marine Snail Venom to Analgesic Drug," in Drugs From the Sea 74-85, Nobuhiro Fusetani ed., Karger 2000), Switzerland.

Osterberg, S., et al., "Regulation of Alternative Sigma Factor Use," Annual Review of Microbiology 65:37-55, Annual Reviews, United States (2011).

Paul, K., et al., "Energy Source of Flagellar Type III Secretion," Nature 451(7177):489-492, Nature Publishing Group, England (2008).

Sanderson, K.E. and Roth, J.R., "Linkage Map of Salmonella typhimurium, Edition VI," Microbiological Reviews 47(3):410-453, American Society for Microbiology, United States (1983).

Singer, H.M., et al., "Selective Purification of Recombinant Neuroactive Peptides Using the Flagellar Type III Secretion System," mBio 3(3):e00115-12, American Society for Microbiology, United States (2012).

Sorenson, M.K., et al., "Crystal Structure of the Flagellar σ/anti-σ Complex σ (28)/FlgM Reveals an Intact σ Factor in an Inactive Conformation," Molecular Cell 14(1):127-138, Cell Press, United States (2004).

Sourjik, V. and Wingreen, N.S., "Responding to Chemical Gradients: Bacterial Chemotaxis," Current Opinion in Cell Biology 24(2):262-268, Elsevier, England (2012).

Takaya, A., et al., "YdiV: A Dual Function Protein that Targets FlhDC for ClpXP-dependent Degradation by Promoting Release of DNA-bound FlhDC Complex," Molecular Microbiology 83(6):1268-1284, Blackwell Scientific Publications, England (2012).

Terlau, H. and Olivera, B.M., "Conus Venoms: A Rich Source of Novel Ion Cchannel-targeted Peptides," Physiological Reviews 84(1):41-68, American Physiological Society, United States (2004).

Tomoyasu, T., et al., "The ClpXP ATP-dependent Protease Regulates Flagellum Synthesis in Salmonella enterica Serovar Typhimurium," Journal of Bacteriology 184(3):645-653, American Society for Microbiology, United States (2002).

Wada, T., et al., "EAL Domain Protein YdiV Acts as an Anti-FlhD4C2 Factor Responsible for Nutritional Control of the Flagellar Regulon in Salmonella enterica Serovar Typhimurium," Journal of Bacteriology 193(7):1600-1611, American Society for Microbiology, United States (2011).

Wang, Q., et al., "The RcsCDB Signaling System and Swarming Motility in Salmonella enterica Terovar typhimurium: Dual Regulation of Flagellar and SPI-2 Virulence Genes," Journal of Bacteriology 189(23):8447-8457, American Society for Microbiology, United States (2007).

Wang, S., et al., "Structure of the Escherichia coli FlhDC Complex, A Prokaryotic Heteromeric Regulator of Transcription," Journal of Molecular Biology 355(4):798-808, Elsevier, England (2006).

Wei, B.L., et al., "Positive Regulation of Motility and flhDC Expression by the RNA-binding Protein CsrA of Escherichia coli," Molecular Microbiology 40(1):245-256, Blackwell Scientific Publications, England (2001).

Wozniak, C.E., et al., "T-POP Array Identifies EcnR and PefI-SrgD as Novel Regulators of Flagellar Gene Expression," Journal of Bacteriology 191(5):1498-1508, American Society for Microbiology, United States (2009).

International Searching Authority, Written Opinion for International Application No. PCT/US13/43384, ISA/US, Alexandria, Virginia, United States, mailed Oct. 25, 2013, 5 pages.

Yamamoto, S. and Kutsukake, K., "FliT Acts as an Anti-FlhD2C2 Factor in the Transcriptional Control of the Flagellar Regulon in Salmonella enterica Serovar Typhimurium," Journal of Bacteriology 188(18):6703-6708, American Society for Microbiology, United States (2006).

Yanagihara, S., et al., "Structure and Transcriptional Control of the Flagellar Master Operon of Salmonella typhimurium," Genetics Society of Japan, Japan 74(3):105-111, Genes and Genetic Systems (1999).

Yao, S., et al., "Structure, Dynamics, and Selectivity of the Sodium Channel Blocker mu-conotoxin SIIIA," Biochemistry 47(41):10940-10949, American Chemical Society, United States (2008).

Yokoseki, T., et al., "Functional Analysis of the Flagellar Genes in the fliD Operon of Salmonella typhimurium," Microbiology 141(Pt 7):1715-1722, Kluwer Academic/Plenum Publishers, United States (1995).

(56) References Cited

OTHER PUBLICATIONS

Jie Zhang, Fusion to FLGM Allows Secretion and Purification of Conotoxin Protein Through the Flagellar Type III Secretion System (Dec. 2008) (M.S. thesis, The University of Utah; available at Marriott Library Special Collections).

Berger, E., et al., "Extracellular secretion of a recombinant therapeutic peptide by Bacillus halodurans utilizing a modified flagellin type III secretion system," Microbial Cell Factories 10(62):1-10 (2011), BioMed Central Ltd., England.

Vonderviszt, F., et al., "The Use of a Flagellar Export Signal for the Secretion of Recombinant Proteins in *Salmonella*," in 824 Recombinant Gene Expression: Reviews and Protocols, Third Edition, Methods in Molecular Biology 131-143 (Angelia Lorence, ed., 2012), Humana Press, United States.

Extended European Search Report of European Appl. No. 13798228.6, European Patent Office, Munich, Germany, mailed Mar. 4, 2016, 5 pages.

Aldridge, P.D., et al., "The flagellar-specific transcription factor, $\sigma 28$, is the Type III secretion chaperone for the flagellar-specific anti-$\sigma 28$ factor FlgM," Genes & Development 20:2315-2326, Cold Harbor Springs Laboratory Press, United States (2006).

Mizusaki, H., et al., "Signal Pathway in Salt-Activated Expression of the *Salmonella* Pathogenicity Island 1 Type III Secretion Systems in *Salmonella enterica* Serovar Typhimurium," Journal of Bacteriology 190(13):4624-4631, American Society for Microbiology, United States (2008).

Widmaier, D.M., et al., "Engineering the *Salmonella* type III secretion system to export spider silk monomers," Molecualr Systems Biology 5:309, 9 pages, Wiley Blackwell, England (2009).

\* cited by examiner

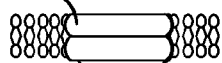
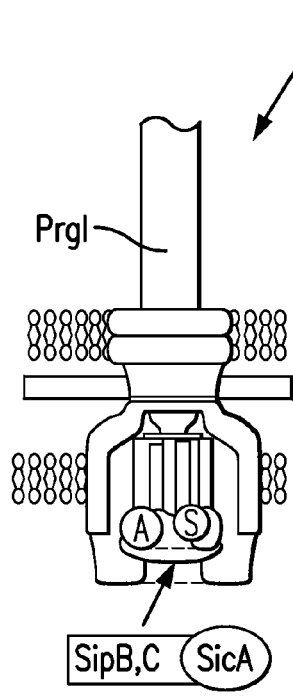
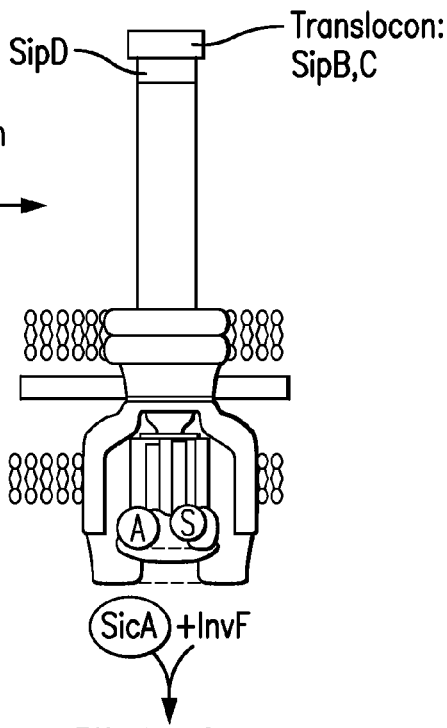
FIG. 15B
FIG. 15C
FIG. 15D
FIG. 15E

COMPOSITIONS AND METHODS FOR PEPTIDE EXPRESSION AND PURIFICATION USING A TYPE III SECRETION SYSTEM

CROSS-REFERENCE TO RELATED APPLICATIONS

This application claims benefit of U.S. Provisional Application No. 61/689,284, filed May 30, 2012, which is hereby incorporated herein by reference in its entirety.

STATEMENT REGARDING FEDERALLY SPONSORED RESEARCH

This invention was made with government support under GM062206 and GM48677 awarded by the National Institutes of Health. The government has certain rights in the invention.

REFERENCE TO SEQUENCE LISTING

The Sequence Listing submitted Jun. 3, 2015 as a text file named "21101_0290U1_updated_sequence_listing.txt," created on Jun. 1, 2015, and having a size of 18,912 bytes is hereby incorporated by reference pursuant to 37 C.F.R. § 1.52(e)(5).

FIELD OF THE INVENTION

The disclosed invention relates generally to the use of FlgM in a type III secretion system for expression of a peptide of interest.

BACKGROUND

Although large strides have been made in the recombinant expression of proteins, the efficient expression of certain classes of proteins remains a challenge. These include the small, highly stable pharmacologically active polypeptides with a high density of disulfide crosslinks. A major group within this general class includes the polypeptides present in animal venoms. Although several different phylogenetic lineages have evolved venoms independently, all polypeptides found have convergently evolved a common set of properties that allow them to be exceptionally stable upon injection into another organism. These polypeptides are of increasing interest because many of them have novel pharmacological activity and therefore serve as useful ligands in basic research or have direct diagnostic and therapeutic applications. One of these peptides, MVIIA a 25 amino acid peptide with three disulfide bonds, has become an approved drug for intractable pain.

When recombinant expression of small disulfide-rich polypeptides is attempted, the yields are generally low. A fundamental problem is that when expression levels are high, the resulting high concentrations of polypeptide in the cell lead to the formation of intermolecular aggregates, and recombinant polypeptides are mostly found in inclusion bodies. The ability to recover the polypeptide from an inclusion body in a biologically active form is not predictable and requires additional steps that vary depending on the polypeptide expressed.

BRIEF SUMMARY

Disclosed herein are compositions and methods for overcoming the current obstacles of production and purification of cysteine-rich polypeptides. The characterization of various factors of controlling flagellar gene expression, ionic conditions, cell growth phase, and removal of cellular proteases or secretion competitors for the purpose of improving yield of secreted protein are disclosed.

Disclosed herein are methods of utilizing the flagellar FlgM protein as a vector for the secretion of small, highly stable pharmacologically-active polypeptides that contain a high density of cysteine residues, which form disulfide crosslinks in the mature product. For example, a bacterial secretion system for the recombinant expression of μ-conotoxin SIIIA in *Salmonella typhimurium* is provided.

Also disclosed herein are bacterial strains that can be used to produce high yields of secreted protein for the purposes of protein purification via flagellar T3 S.

Disclosed are compositions and methods for production and purification of polypeptides using a bacterial flagellar system.

Disclosed are constructs comprising a FlgM nucleic acid sequence, a cleavage site, and a nucleic acid sequence of interest. The constructs can further comprise a nucleic acid sequence encoding a purification tag. The purification tag can be poly-histidine.

The FlgM nucleic acid sequence of the disclosed constructs can be wild type FlgM. The cleavage site can be a Tobacco Etch Virus (TEV) protease cleavage site or an Enterokinase (ETK) cleavage site.

The nucleic acid sequence of interest of the disclosed constructs can encode a cysteine-rich peptide. The cysteine-rich peptide can be a neuroactive toxin, such as a conopeptide. The conopeptide can be a μ-conotoxin such as SIIIA.

The disclosed constructs can have the cleavage site between the FlgM nucleic acid sequence and the nucleic acid sequence of interest. The order of the sequences in the constructs can be the FlgM nucleic acid sequence, the nucleic acid sequence encoding a purification tag, the cleavage site, and the nucleic acid sequence of interest. The order of the sequences in the constructs can be the nucleic acid sequence encoding a purification tag, the FlgM nucleic acid sequence, the cleavage site, and the nucleic acid sequence of interest. The order of the sequences in the constructs can also include the nucleic acid sequence encoding a purification tag being C-terminal to the nucleic acid sequence of interest.

The disclosed constructs can also comprise a $P_{ara}$BAD promoter.

Also disclosed are polypeptides comprising FlgM, a cleavage site, and a peptide of interest. The polypeptides can further comprise a purification tag. The purification tag can be poly-histidine.

The FlgM in the disclosed polypeptides can be wild type FlgM. The cleavage site can be a TEV protease cleavage site or an ETK cleavage site.

The peptide of interest in the disclosed polypeptides can be a cysteine-rich peptide. The cysteine-rich peptide can be a neuroactive toxin such as a conopeptide. The conopeptide can be a μ-conotoxin such as SIIIA.

The disclosed polypeptides can have the cleavage site between the FlgM and the peptide of interest. The order of the sequences in the polypeptides can be the FlgM is N-terminal to the purification tag, the purification tag is N-terminal to the cleavage site, and the cleavage site is N-terminal to the peptide of interest. The order of the sequences in the polypeptide can be the purification tag is N-terminal to FlgM, FlgM is N-terminal to the cleavage site, and the cleavage site is N-terminal to the peptide of interest. In some aspects, the purification tag is C-terminal to the peptide of interest.

Also disclosed are recombinant cell lines comprising any of the disclosed constructs. The recombinant cell line can be derived from a wild type strain of Salmonella enterica serovar Typhimurium.

The genome of the disclosed recombinant cell lines can comprise an alteration to one or more flagellin or hook-associated protein genes. The one or more flagellin genes can be selected from the group consisting of flgK, flgL, fliC, fljB, and fliD.

The disclosed recombinant cell lines can comprise an alteration to one or more inhibitors of the flagellar FlhD4C2 master regulatory protein complex. The inhibitors of the flagellar FlhD4C2 master regulatory protein complex can be selected from the group consisting of fimZ, srgD, hdfR, rbsR, ompR, clpX, clpP, lrhA, ydiV, dskA, ecnR, fliT, and rcsB.

The disclosed recombinant cell lines can comprise a mutation to increase transcription or translation of the FlgM T3S-chaperone gene fliA.

Also disclosed are methods of producing a peptide of interest comprising culturing a cell line comprising any of the disclosed polypeptides in culture media, wherein the polypeptide comprises the peptide of interest. The methods can further include purifying the peptide of interest from the culture media. The methods can use a cell line that comprises any of the disclosed constructs.

The purifying of the peptide of interest can comprise an affinity column such as $\sigma^{28}$ affinity column.

The disclosed methods can use a cell line that comprises a flagellar type III secretion (T3 S) system of Salmonella enterica serovar Typhimurium to secrete the polypeptide comprising the peptide of interest.

The disclosed methods can use a cell line that comprises an alteration to one or more flagellin hook-associated protein genes. The one or more flagellin or hook-associated protein genes can be selected from the group consisting of flgK, flgL, fliC, fljB, and fliD.

The disclosed methods can use a cell line that comprises an alteration to one or more inhibitors of the flagellar FlhD4C2 master regulatory protein complex. The inhibitors of the flagellar FlhD4C2 master regulatory protein complex can be selected from the group consisting of fimZ, srgD, hdfR, rbsR, ompR, clpX, clpP, lrhA, ydiV, dskA, ecnR, fliT, and rcsB.

The disclosed methods can use a cell line that comprises a mutation to increase transcription or translation of the FlgM T3S-chaperone gene fliA.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 3 shows the effect of *Salmonella* poly-hook background on secretion. (A) Immunostaining of the poly-hook background TH16778 used for secretion of FlgM-H6-TEV-toxin fusions. Top left: Membrane stained with FM-64. Top right: DNA stained with Hoechst. Bottom left: Flagellar hook-basal-body complexes (flgE::3xHA) labeled with anti-hemagglutinin antibodies coupled to Alexa Fluor-488. Scale bar is 5 μm. (B) Secreted proteins were precipitated using TCA and immunoblots with antibodies against FlgM and FliK are shown for cellular and supernatant fractions. Protein bands of native FlgM (open triangle) and FlgM-SIIIA fusions (filled triangle) are marked next to the blot. Secretion levels were compared by measuring the densitometric intensity of the detected bands using ImageJ. Secretion values relative to the secretion in a Para wildtype background (first lane) are displayed below the corresponding band.

FIG. 4 shows FlgM secretion under ParaBAD over-expression conditions. Western blot analysis of supernatant fractions of strains over-expressing FlgM from the chromosomal araBAD promoter (ParaBAD-FlgM+). Overnight cultures were diluted 100-fold into LB medium, incubated at 37° C. for 2 hours, followed by addition of arabinose to 0.2% to induce ParaBAD-FlgM+. After 5 hours further incubation at 37° C., cells were separated from the supernatant by centrifugation and TCA was added to the cell supernatant to precipitate secreted protein (see Example 2). For the secreted protein analysis, 100 OD units of sample were loaded into each lane. For whole cell protein analysis, 50 OD units of sample were loaded. Anti-FlgM antibody was used to determine levels of secreted and whole cell FlgM (secreted FlgM=Se FlgM, Whole cell FlgM=WC FlgM, 0.2% arabinose=Ara).

FIG. 5 shows the effect of flhDC operon expression on levels of secreted FlgM and cell motility. (A) Secreted levels of FlgM was determined in strains affected in flhDC operon expression by quantitative Western blot analysis using anti-FlgM antibody to detected FlgM in the supernatant of the spent growth medium. (secreted FlgM=Se FlgM, cellular soluble FlgM=So FlgM, cellular insoluble FlgM=Inso FlgM, and whole cellular DnaK=WC DnaK). (B) Relative FlgM secreted levels. (C) Swim phenotype on soft agar plates of strain TH18649 (ΔPflhDC8089::tetR-PtetA ΔaraBAD1156::FlgM+) with no inducers added, 1 μg/ml anyhdrotetracycline (ATc,) added and both ATc and 0.2% arabinose (Ara) added. (D) Motility assay in various mutant backgrounds depicted with ΔaraBAD1156::FlgM+ in the absence and presence of added 0.2% arabinose.

FIG. 6 shows the effect of fliA(σ28) alleles on levels of secreted FlgM and cell motility. (A) Secreted levels of FlgM was determined in strains carrying different alleles of the $\sigma^{28}$ structural gene fliA by quantitative Western blot analysis using anti-FlgM antibody to detected FlgM in the supernatant of the spent growth medium. (secreted FlgM=Se FlgM, whole cellular FlgM=WC FlgM, whole cellular FliA=WC FliA, and whole cellular DnaK=WC DnaK). (B) Relative FlgM secreted levels. (C) Motility assay in various mutant backgrounds depicted with ΔaraBAD1156::FlgM+ in the absence and presence of added 0.2% arabinose.

FIG. 7 shows the effect of flagellar late substrate deletion, growth phase, and fljBenx vh2 mutations on levels of secreted FlgM and cell motility. (A) Secreted levels of FlgM was determined in strains carrying different flagella late substrate genes (flgK, flgL, fliC, fliD and fljB) deletion mutants, growth phase (Δhin-5717, Δhin-5718) mutants and fljBenx vh2 mutants by quantitative Western blot analysis using anti-FlgM antibody to detected FlgM in the supernatant of the spent growth medium. (secreted FlgM=Se FlgM, cellular soluble FlgM=So FlgM, cellular insoluble FlgM=Inso FlgM, and whole cellular DnaK=WC DnaK). (B) Relative FlgM secreted levels.

FIG. 8 shows the effects of late flagella T3S chaperone deletion mutations on levels of secreted FlgM and cell motility. (A) Secreted levels of FlgM was determined in strains carrying different deletion mutant alleles of the flagellar T3 S chaperone genes flgN, fliS and fliT structural genes by quantitative Western blot analysis using anti-FlgM antibody to detected FlgM in the supernatant of the spent growth medium. (secreted FlgM=Se FlgM, whole cellular FlgM=WC FlgM, and whole cellular DnaK=WC DnaK). (B) Relative FlgM secreted levels.

FIG. 9 shows the effects of Spi-1 and Spi-2 mutations deletion mutations on levels of secreted FlgM and cell motility. (A) Secreted levels of FlgM was determined in strains carrying deletion mutant alleles of the either the Spi1 or Spi2 genes by quantitative Western blot analysis using anti-FlgM antibody to detected FlgM in the supernatant of the spent growth medium. (secreted FlgM=Se FlgM, whole cellular FlgM=WC FlgM, and whole cellular DnaK=WC DnaK). (B) Relative FlgM secreted levels.

FIG. 10 shows the effects of cellular protease mutant alleles on levels of secreted FlgM and cell motility. (A) Secreted levels of FlgM was determined in strains carrying deletion mutant alleles of the ompT, degP, clpA, clpX or clpP genes with and without a functional flhDC operon by quantitative Western blot analysis using anti-FlgM antibody to detected FlgM in the supernatant of the spent growth medium. (secreted FlgM=Se FlgM, whole cellular FlgM=WC FlgM, and whole cellular DnaK=WC DnaK). (B) Relative FlgM secreted levels in the flhD+C+ and flhDC null backgrounds, and relative whole cell FlgM accumulation level in flhDC null background. (C) Motility assay in various mutant backgrounds depicted with ΔaraBAD1156: FlgM+ in the absence and presence of added 0.2% arabinose.

FIG. 11 shows the effects of NaCl and KCl ionic strengths on levels of secreted FlgM and cell motility. (A) Secreted levels of FlgM was determined in medium with NaCl and KCl added at concentrations depicted by quantitative Western blot analysis using anti-FlgM antibody to detected FlgM in the supernatant of the spent growth medium. (secreted FlgM=Se FlgM, cellular soluble FlgM=So FlgM, cellular insoluble FlgM=Inso FlgM, and whole cellular DnaK=WC DnaK). (B) Relative FlgM secreted levels. (C) Motility assay in various mutant backgrounds depicted with ΔaraBAD1156::FlgM+ in the absence and presence of added 0.2% arabinose.

FIG. 12 shows the effects of different combined mutations on levels of secreted FlgM. (A) Secreted levels of FlgM was determined in strains carrying different combined mutations depicted by quantitative western blot analysis using anti-FlgM antibody to detected FlgM in the supernatant of the spent growth medium (secreted FlgM=Se FlgM, whole cellular FlgM=WC FlgM, and whole cellular DnaK=WC DnaK). (B) Relative FlgM secreted levels.

FIG. 13 shows the effects of different combined mutations on levels of secreted FlgM-6H-TEV-δ-SVIE and FlgM-6H-ETK-δ-SVIE. (A) Secreted levels of FlgM-6His-TEV-δ-SVIE and FlgM-6His-ETK-δ-SVIE was determined in strains carrying different combined mutations depicted by quantitative western blot analysis using anti-FlgM antibody to detected FlgM-6His-TEV-δ-SVIE and FlgM-6His-ETK-δ-SVIE in the supernatant of the spent growth medium (secreted FlgM-6His-TEV-δ-SVIE=Se FlgM-6His-TEV-SVIE, secreted FlgM-6His-ETK-δ-SVIE=Se FlgM-6His-ETK-δ-SVIE, secreted FlgM=Se FlgM, and whole cellular DnaK=WC DnaK). (B) Relative FlgM-6His-TEV-δ-SVIE and FlgM-6His-ETK-δ-SVIE secreted levels.

Figure 14:
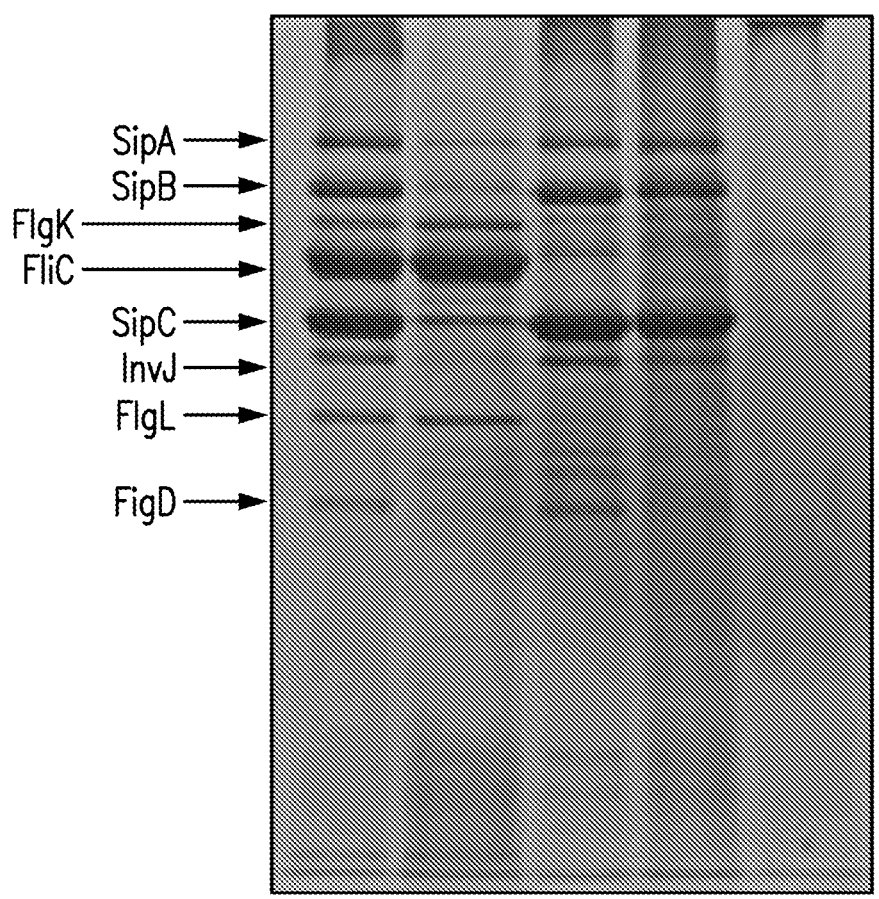

FIG. 14 shows type III secreted proteins. A coomassie-stained SDS gel from the spent growth medium of *Salmonella* cells in wild-type and mutant strains was run. Lane 1 wild-type, lane 2 mot, lane 3 fliK, lane 4 flhD, lane 5 flhD invA.

FIG. 15 shows the *Salmonella* SPI1 injectisome system. (A) All genes required for the structure and assembly of the SPI1 injectisome are clustered in the chromosome. (B) SPI1 genes are under control of the flagellar master operon flhDC, which leads to the successive transcription of the FliZ, HilD and HilA regulators and HilA is required for injectisome gene transcription. (C) Injectisome basal body (IBB) completion is followed by (D) needle and (E) translocon assembly.

Figure 16:
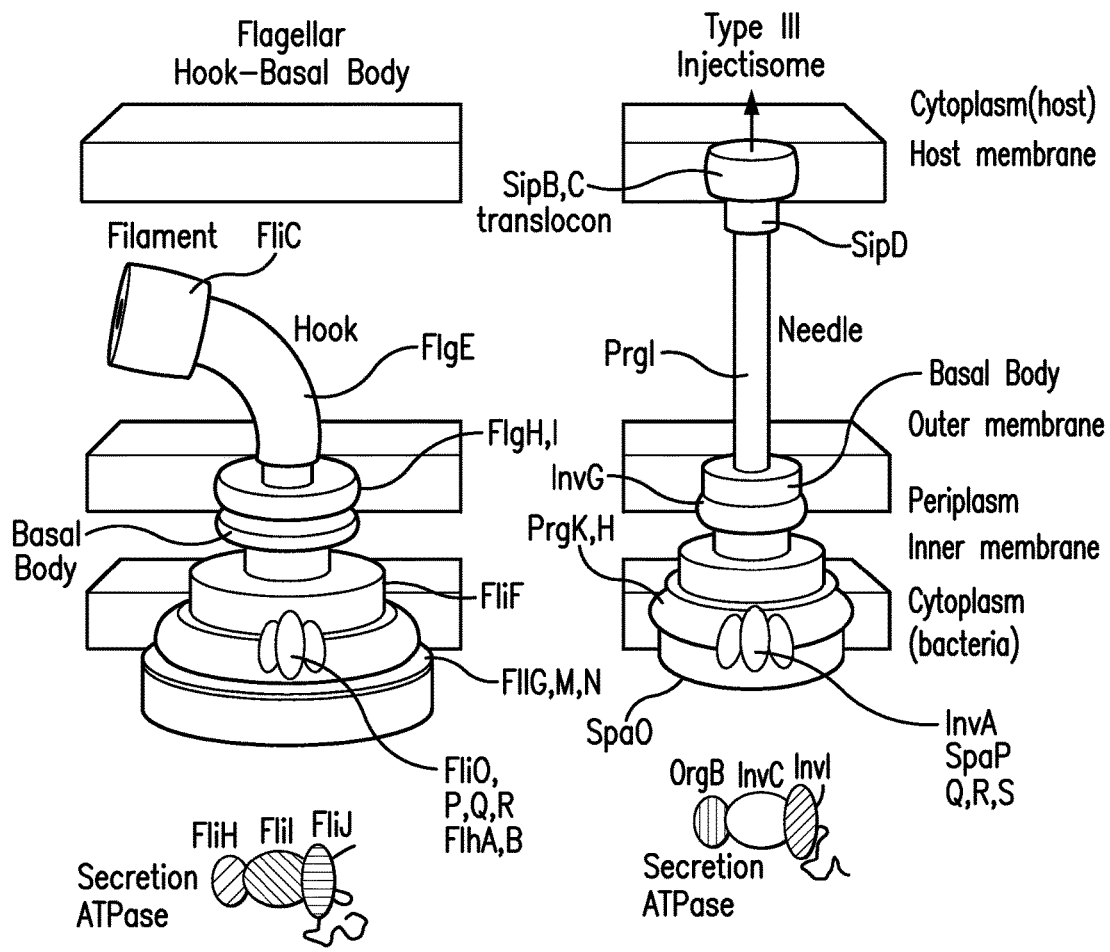

FIG. 16 shows flagellar and SPI1 injectisome structures. The structures show overall similarities in structure with strong homologies to basal and secretion-associated component proteins.

DETAILED DESCRIPTION

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

It must be noted that as used herein and in the appended claims, the singular forms "a", "an", and "the" include plural reference unless the context clearly dictates otherwise. Thus, for example, reference to "a polypeptide" includes a plurality of such polypeptides, reference to "the cell line" is a reference to one or more cell lines and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector. Moreover, the invention is intended to include other vectors which serve equivalent functions.

The term "sequence of interest" or "nucleic acid sequence of interest" can mean a nucleic acid sequence (e.g., gene capable of encoding a cysteine-rich peptide), that is partly or entirely heterologous, i.e., foreign, to a cell into which it is introduced.

The term "sequence of interest" or "nucleic acid sequence of interest" can also mean a nucleic acid sequence, that is partly or entirely homologous to an endogenous gene of the cell into which it is introduced, but which is designed to be inserted into the genome of the cell in such a way as to alter the genome (e.g., it is inserted at a location which differs from that of the natural gene or its insertion results in "a knock-in"). For example, a sequence of interest can be cDNA, DNA, or mRNA.

A "peptide of interest" or "protein of interest" means a peptide or polypeptide sequence (e.g., a cysteine-rich peptide), that is expressed from a sequence of interest or nucleic acid sequence of interest.

The term "operatively linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative linkage of DNA to a transcriptional control element can refer to the physical and functional relationship between the DNA and promoter such that the transcription of such DNA is initiated from the promoter by an RNA polymerase that specifically recognizes, binds to and transcribes the DNA.

The terms "transformation" and "transfection" mean the introduction of a nucleic acid, e.g., an expression vector, into a recipient cell including introduction of a nucleic acid to the chromosomal DNA of said cell.

Also disclosed are transcriptional control elements (TCEs). TCEs are elements capable of driving expression of nucleic acid sequences operably linked to them. The constructs disclosed herein comprise at least one TCE. TCEs can optionally be constitutive or regulatable.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a construct is disclosed and discussed and a number of modifications that can be made to a number of molecules including the construct are discussed, each and every combination and permutation of the construct and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed Those skilled in the art will recognize, or be able to ascertain using no more than routine experimentation, many equivalents to the specific embodiments of the method and compositions described herein. Such equivalents are intended to be encompassed by the following claims.

B. Bacteria Flagella

Many bacteria utilize flagella to move in a directed manner, either away from stressful environments or towards nutrients, $O_2$, light and other positive stimuli. The bacterial flagellum is a complex cellular machine that requires more than 30 gene products for its construction. For *Salmonella enterica* there are currently more than 60 genes involved in the biogenesis and function of its flagella. These genes are organized into a transcriptional hierarchy of 3 promoter classes. At the top of the flagellar transcriptional hierarchy is the flhDC operon encoding the master regulator proteins FlhD and FlhC, which form a heteromultimeric, transcriptional activation complex. The FlhD4C2 complex directs $\sigma^{70}$ RNA polymerase to transcribe from class 2 flagellar promoters. Class 2 flagellar genes encode proteins required for the structure and assembly of a rotary motor called the hook-basal body (HBB), a key structural intermediate in flagellum assembly. The HBB includes the flagellar type III secretion (T3 S) system, which exports flagellar proteins from the cytoplasm through the growing structure during assembly. In addition to HBB gene expression, flagellar class 2 transcription produces $\sigma^{28}$ (FliA) and FlgM. These are regulatory proteins that couple transcription of the flagellar class 3 promoters to completion of the HBB. The $\sigma^{28}$ protein is a flagellar-specific transcription factor that directs RNA polymerase to transcribe from the flagellar class 3 promoters. Class 3 genes include the structural genes of the flagellar filament and genes of the chemosensory signal transduction system that controls the direction of flagellar rotation according to changing concentrations of extracellular ligands. Prior to HBB completion, FlgM binds $\sigma^{28}$ and prevents flagellar class 3 promoter transcription. Upon HBB completion, a change in the flagellar T3S substrate specificity results in FlgM secretion and initiation of $\sigma^{28}$-dependent transcription from flagellar class 3 promoters. The secretion signal requirements for T3S substrates remains poorly defined, but all substrates utilize an N-terminal peptide secretion signal that is disordered in structure and unlike type II secretion, is not cleaved during the secretion process. Substrate secretion is often facilitated by T3S chaperone-assisted delivery to the secretion apparatus. The FlgM protein is 97 amino acids in length and its secretion is dependent on an N-terminal secretion signal. FlgM secretion is greatly enhanced by its secretion chaperone, $\sigma^{28}$, which binds to the C-terminal half of FlgM.

Because FlgM is a small T3S substrate and not part of the final flagellar structure, it can be used as a vehicle to direct secretion of proteins for purification purposes. Fusion of foreign peptides to the C-terminus of FlgM can be used to direct their secretion either into the periplasm or into the extracellular milieu. The FlgM type III secretion system can be used to express and purify recombined proteins.

Disclosed are constructs and methods that use an expression system that exploits the flagellar secretion system of *Salmonella enterica* serovar *Typhimurium* (*Salmonella typhimurium*) and bypasses the inclusion body problem of recombinant small peptide expression.

C. Nucleic Acids Constructs

Disclosed are nucleic acid constructs comprising a FlgM nucleic acid sequence, a cleavage site, and a nucleic acid sequence of interest. The constructs can further comprise a nucleic acid sequence encoding a purification tag.

The order of the FlgM nucleic acid sequence, the cleavage site, and the nucleic acid sequence of interest can vary. In some aspects, the order of the sequences can be from 5' to 3', the FlgM nucleic acid sequence, the nucleic acid sequence encoding a purification tag, the cleavage site, and the nucleic acid sequence of interest. In some aspects, the order of the sequences can be from 5' to 3', the nucleic acid sequence encoding a purification tag, the FlgM nucleic acid sequence, the cleavage site, and the nucleic acid sequence of interest. In some aspects, the order of the sequences can be from 5' to 3', the FlgM nucleic acid sequence, the cleavage site, the nucleic acid sequence encoding a purification tag, and the nucleic acid sequence of interest. In some aspects, the order of the sequences can be from 5' to 3', the FlgM nucleic acid sequence, the cleavage site, the nucleic acid sequence of interest, and the nucleic acid sequence encoding a purification tag. Thus, the nucleic acid sequence encoding a purification tag can be 5' or 3' to the nucleic acid sequence of interest.

1. FlgM

The disclosed constructs comprise a FlgM nucleic acid sequence. The FlgM nucleic acid sequence can be wild type FlgM. In some aspects, the FlgM nucleic acid sequence can be a mutant sequence of FlgM. The mutant sequence of FlgM can have one or more nucleotide mutations compared to wild type FlgM. In some aspects, the mutations do not change the encoded amino acid sequence. In some aspects, the mutations in the mutant nucleic acid sequence of FlgM does not affect the ability of the encoded FlgM peptide to act as a vector for the secretion of the peptide encoded by the nucleic acid sequence of interest.

2. Cleavage Site

The disclosed constructs can comprise a cleavage site between the FlgM nucleic acid sequence and the nucleic acid sequence of interest. The cleavage site can be a Tobacco Etch Virus (TEV) protease cleavage site or an Enterokinase (ETK) cleavage site. Other cleavage sites known to those of skill in the art can be used. Although the cleavage site is between the FlgM nucleic acid sequence and the nucleic acid sequence of interest, the cleavage site does not always have to be contiguous with those sequences. In other words, a sequence encoding a purification tag can be directly before or after the cleavage site.

The cleavage site can be a protease cleavage site. Therefore, the nucleic acid sequence of the cleavage site can encode a protease cleavage site. The cleavage site is not a nuclease cleavage site and thus the nucleic acid sequences present in the constructs are not cleaved. The cleavage site allows for cleavage of the polypeptide encoded by the disclosed constructs. Cleavage of the polypeptide encoded by the disclosed constructs can release the peptide of interest (encoded by the nucleic acid of interest) from FlgM peptide (encoded by the FlgM nucleic acid sequence).

3. Nucleic Acid Sequence of Interest

The disclosed constructs comprise a nucleic acid sequence of interest. The nucleic acid sequence of interest can encode a peptide of interest to be expressed and purified using the FlgM system provided herein.

In some aspects, the nucleic acid sequence of interest encodes a cysteine-rich peptide or a disulfide-rich peptide. Recombinant expression of small disulfide-rich polypeptides results in generally low yields. Overexpression of these polypeptides can lead to the formation of intermolecular aggregates, and the recombinant polypeptides can be found in the inclusion bodies. Because recovering the polypeptides from the inclusion bodies can be difficult and time consuming, these disulfide-rich polypeptides are best purified using the FlgM expression system disclosed herein.

In some aspects, the nucleic acid sequence of interest encodes a cysteine-rich peptide or a disulfide-rich peptide, wherein the disulfide-rich or cysteine-rich polypeptides is a neuroactive toxin. The neuroactive toxin can be any neuroactive toxin. In some aspects, the neuroactive toxin can be a conoidean derived toxin (i.e. a toxin from a conoidean). In some aspects, the neuroactive toxin can be a conopeptide. The conopeptide can be a μ-conotoxin. Examples of μ-conotoxins include but are not limited to SIIIA.

4. Purification Tag

The disclosed constructs can further comprise a sequence encoding a purification tag. Examples of purification tags include, but are not limited to poly-histidine, glutathione S-transferase (GST), Myc, HA, FLAG, and maltose binding protein (MBP). Thus, nucleic acid sequences that encode these purification tags are disclosed. Purification tags and the nucleic acid sequences that encode them are well known in the art.

5. Promoter

The disclosed constructs can also comprise transcriptional control elements (TCEs). TCEs are elements capable of driving expression of nucleic acid sequences operably linked to them. The constructs disclosed herein comprise at least one TCE. TCEs can optionally be constitutive or regulatable. For example, disclosed herein are constructs comprising a $P_{araBAD}$ promoter. The $P_{araBAD}$ promoter is an arabinose-inducible promoter. This allows for expression of the nucleic acid sequences downstream of the promoter to be turned on or off in the presence or absence of arabinose.

Regulatable TCEs can comprise a nucleic acid sequence capable of being bound to a binding domain of a fusion protein expressed from a regulator construct such that the transcription repression domain acts to repress transcription of a nucleic acid sequence contained within the regulatable TCE.

Alternatively, the construct comprising the regulatable TCE can further comprise the nucleic acid sequence capable of encoding a drug-controllable (such as a drug inducible) repressor fusion protein that comprises a DNA binding domain and a transcription repression domain. In such an arrangement, the nucleic acid sequence capable of encoding a drug-controllable (such as a drug inducible) repressor fusion protein is on the same construct as the regulatable TCE to which the repressor fusion protein binds.

Regulatable TCEs can optionally comprise a regulator target sequence. Regulator target sequences can comprise nucleic acid sequence capable of being bound to a binding domain of a fusion protein expressed from a regulator construct such that a transcription repression domain acts to repress transcription of a nucleic acid sequence contained within the regulatable TCE. Regulator target sequences can comprise one or more tet operator sequences (tetO). The regulator target sequences can be operably linked to other sequences, including, but not limited to, a TATA box or a GAL-4 encoding nucleic acid sequence.

The presence of a regulatable TCE and a regulator sequence, whether they are on the same or a different construct, allows for inducible and reversible expression of the sequences operably linked to the regulatable TCE. As such, the regulatable TCE can provide a means for selectively inducing and reversing the expression of a sequence of interest.

Regulatable TCEs can be regulatable by, for example, tetracycline or doxycycline. Furthermore, the TCEs can optionally comprise at least one tet operator sequence.

D. Polypeptides

Also disclosed herein are polypeptides encoded by the nucleic acid constructs disclosed above and elsewhere herein. For example, disclosed herein are polypeptides comprising FlgM, a cleavage site, and a peptide of interest. The polypeptides can further comprise a purification tag.

In the disclosed polypeptides, the FlgM can be N-terminal to the purification tag, the purification tag can be N-terminal to the cleavage site, and the cleavage site can be N-terminal to the peptide of interest. Alternatively, the purification tag can be N-terminal to FlgM, FlgM can be N-terminal to the cleavage site, and the cleavage site can be N-terminal to the peptide of interest. In some aspects, the purification tag can be C-terminal to the peptide of interest.

Thus, the order of the polypeptide can be, for example, 1) Tag-FlgM-cleavage site-peptide of interest, 2) FlgM-Tag-cleavage site-peptide of interest, 3) FlgM-cleavage site-Tag-peptide of interest, or 4) FlgM-cleavage site-peptide of interest-Tag.

1. FlgM

The disclosed polypeptides comprise FlgM. The FlgM can be wild type FlgM. In some aspects, the FlgM can be a mutant FlgM. The mutant FlgM can have one or more amino acid mutations compared to wild type FlgM. In some aspects, the mutations in the mutant FlgM does not affect the ability of FlgM to act as a vector for the secretion of the peptide of interest.

2. Cleavage Site

The disclosed polypeptides can comprise a cleavage site between FlgM and the peptide of interest. The cleavage site can be a TEV protease cleavage site or an ETK cleavage site. Although the cleavage site is between the FlgM and the peptide of interest, the cleavage site does not always have to be contiguous with FlgM and the peptide of interest. In other words, a purification tag can be directly before or after the cleavage site.

The cleavage site can be a protease cleavage site. The cleavage site allows for cleavage of the polypeptide. Cleavage of the polypeptide can release the peptide of interest from the FlgM.

3. Peptide of Interest

The disclosed polypeptides comprise a peptide of interest. The peptide of interest can be a peptide to be expressed using the FlgM system provided herein.

In some aspects, the peptide of interest can be a cysteine-rich peptide or a disulfide-rich peptide. The disulfide-rich or cysteine-rich peptides can be a neuroactive toxin. The neuroactive toxin can be any neuroactive toxin. In some aspects, the neuroactive toxin can be a conoidean derived toxin (i.e. a toxin from a conoidean). In some aspects, the neuroactive toxin can be a conopeptide. The conopeptide can be a μ-conotoxin. Examples of μ-conotoxins include but are not limited to SIIIA.

The peptide of interest can vary in size. In some aspects, the peptide of interest can be 5, 10, 15, 20, 25, 30, 35, 40, 45, 50, 55, 60, 65, 70, 75, 80, 85, 90, 95, or 100 amino acids long. In some aspects, the peptide of interest can be 5, 10, 15, 20, 25, 30, or 35 amino acids long. The peptide of interest can vary in size. In some aspects, the peptide of interest can be 50, 100, 150, 200, 250, 300, 350, 400, 450, 500, 550, 600, 650, 700, 750, 800, 850, 900, 950, or 1000 amino acids long. In some aspects, the peptide of interest can be 50, 100, 150, 200, 250, 300, 350, 400, 450, 500, 550, or 600 amino acids long.

4. Purification Tag

The disclosed polypeptides can further comprise a purification tag. Examples of purification tags include, but are not limited to poly-histidine, glutathione S-transferase (GST), Myc, HA, FLAG, and maltose binding protein (MBP).

The purification tag can be used to purify the polypeptide after it has been secreted into the culture media via the FlgM secretion system.

E. Cell Lines

Disclosed are recombinant cell lines as provided in Tables 1 and 4.

Also disclosed herein are recombinant cell lines that comprise any of the disclosed constructs comprising a FlgM nucleic acid sequence, a cleavage site, and a nucleic acid sequence of interest. In some aspects, the recombinant cell lines can comprise one or more of the following sequences: FlgM nucleic acid sequence, a cleavage site, and a nucleic acid sequence of interest. In some aspects, the recombinant cell lines can have a mutation of the construct comprising the FlgM nucleic acid sequence, a cleavage site, and a nucleic acid sequence of interest.

The recombinant cell lines can be derived from a wild type strain of *Salmonella enterica* serovar *Typhimurium*. In some aspects, the recombinant cell line can be derived from a mutant strain of *Salmonella enterica* serovar *Typhimurium*. The recombinant cell lines can be derived from other enteric bacterial species. For example, the recombinant cell lines can be derived from *E. Coli* or *Yersinia*.

Disclosed are recombinant cell lines, wherein the genome of the recombinant cell line comprises an alteration to one or more flagellin or hook-associated protein genes. The one or more flagellin genes can be selected from the group consisting of flgK, flgL, fliC, fljB, and fliD.

Disclosed are recombinant cell lines, wherein the cell line comprises an alteration to one or more inhibitors of the flagellar FlhD4C2 master regulatory protein complex. The inhibitors of the flagellar FlhD4C2 master regulatory protein complex can be selected from the group consisting of fimZ, srgD, hdfR, rbsR, ompR, clpX, clpP, lrhA, ydiV, dskA, ecnR, fliT, and rcsB. Together with $\sigma^{70}$, FlhD4C2 activates the transcription of class II promoters, including those of fliA, FlgM, and genes for hook basal body assembly Inhibition of FlhD4C2 can result in a reduction in FlgM or the number of hook basal body structures. Therefore, the recombinant cell lines having an alteration to one or more inhibitors of the flagellar FlhD4C2 master regulatory protein complex can positively affect the secretion of disclosed polypeptides.

The recombinant cell lines can comprise a mutation to increase transcription or translation of the FlgM T3 S-chaperone gene fliA. FliA is considered a FlgM T3 S-chaperone gene because fliA encodes for $\sigma^{28}$ and $\sigma^{28}$ binds to FlgM and protects FlgM from proteolysis in the cytoplasm of the cell. Therefore, a mutation that increases transcription or translation of the fliA gene can lead to more or better FlgM secretion. And as disclosed in the constructs herein, FlgM is part of a polypeptide that also contains a peptide of interest. Thus, more or better secretion of FlgM leads to more or better secretion of the peptide of interest. In some aspects, the mutations in the fliA gene resulted in an H14N, H14D, T138I or E203D mutation in the encoded $\sigma^{28}$.

Also disclosed are combinations of any of the cells lines disclosed. These combination strains can comprise any of the disclosed constructs having a FlgM nucleic acid sequence, a cleavage site, and a nucleic acid sequence of interest.

F. Methods

Disclosed are methods of producing a peptide of interest comprising culturing a cell line in culture media wherein the cell line comprises any of the disclosed polypeptides that contain FlgM, a cleavage site, and the peptide of interest. The methods can further include purifying the peptide of interest from the culture media.

The disclosed methods can include cell lines comprising any of the disclosed nucleic acid constructs that contain a FlgM nucleic acid sequence, a cleavage site, and a nucleic acid sequence of interest. The nucleic acid sequence of interest encodes the peptide of interest being produced.

The step of purifying the peptide of interest can include an affinity column. In some aspects, the affinity column can be a $\sigma^{28}$ affinity column. The affinity column can be any column designed to purify the peptide of interest or the polypeptide of interest that contains the peptide of interest by using an attraction between one of the peptides on the polypeptide and a molecule on the affinity column. For example, a $\sigma^{28}$ affinity column can be used because $\sigma^{28}$ binds to FlgM which is on the polypeptide which also contains the peptide of interest. The affinity column can also be based on the purification tag present in the polypeptide. In some aspects, the affinity column can have antibodies that bind to FlgM, the purification tag, or the peptide of interest.

The purification of the peptide of interest can include purification of the polypeptide that comprises FlgM, a cleavage site, and the peptide of interest.

The peptide of interest can be cleaved by using the cleavage site present between FlgM and the peptide of interest. The peptide of interest can be cleaved before, after, or during purification. For example, using the disclosed cell lines that have a polypeptide that includes FlgM, a cleavage site and the peptide of interest allows for FlgM to direct the polypeptide and be secreted through a flagellar type III secretion system into the media that the cells are cultured in. The peptide of interest can be cleaved away from the rest of the polypeptide by adding a protease specific to the cleavage site of the polypeptide. The peptide of interest can then be purified from the culture media. Alternatively, the peptide of interest can be purified along with the rest of the polypeptide that comprises the peptide of interest. After purification, the polypeptide can be cleaved and the peptide of interest released. Alternatively, the peptide of interest can be cleaved during purification. The polypeptide can be bound to the affinity column during purification and while bound, the polypeptide can be cleaved releasing the peptide of interest from the remaining polypeptide.

The cell lines of the disclosed methods can be any of the disclosed recombinant cell lines. In some aspects, the cell lines can have a flagellar type III secretion (T3 S) system of *Salmonella enterica* serovar *Typhimurium* to secrete the polypeptide comprising the peptide of interest. In some aspects, the cell lines can have an alteration to one or more flagellin genes or hook-associated protein genes. The one or more flagellin or hook-associated protein genes can be selected from the group consisting of flgK, flgL, fliC, fljB, and fliD. In some aspects, the cell lines can have an alteration to one or more inhibitors of the flagellar FlhD4C2 master regulatory protein complex. The inhibitors of the flagellar FlhD4C2 master regulatory protein complex can be selected from the group consisting of fimZ, srgD, hdfR, rbsR, ompR, clpX, clpP, lrhA, ydiV, dskA, ecnR, fliT, and rcsB. In some aspects, the cell lines can have a mutation to increase transcription or translation of the FlgM T3S-chaperone gene fliA.

G. Kits

The materials described above as well as other materials can be packaged together in any suitable combination as a kit useful for performing, or aiding in the performance of, the disclosed methods. It is useful if the kit components in a given kit are designed and adapted for use together in the disclosed method. For example disclosed are kits for producing a peptide of interest, the kit comprising one of the disclosed recombinant cell lines. The kits also can contain culture media.

The disclosed kits can also include materials for purifying the peptide of interest. For example, the kits can include an affinity column for purifying the peptide of interest based on the purification tag present on the polypeptide.

EXAMPLES

A. Example 1

Figure 1A:
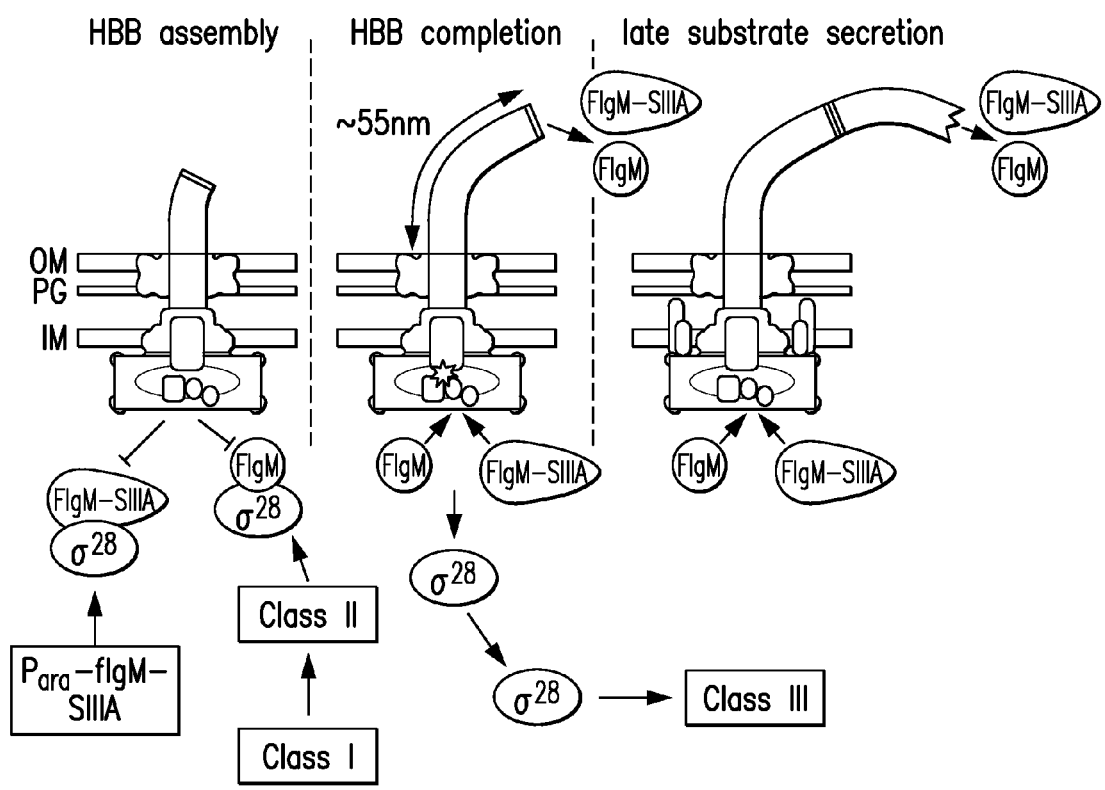
FIG. 1 shows engineering of a flagellar type III secretion system for the secretion of SIIIA conotoxins. (A) Model: A FlgM-SIIIA translational fusion is a secretion substrate of the bacterial T3SS. The fusion construct is secreted via the flagellar-specific T3SS through the flagellar channel into the culture medium through flagellar structures that are competent for FlgM secretion. Expression of FlgM-SIIIA is induced upon addition of arabinose and is independent of flagellar class I and II gene expression. During HBB assembly, FlgM remains inside the cytosol and acts as an anti σ28-factor preventing transcription of class III genes, e.g. genes encoding for the flagellin subunit FliC or the stator proteins MotAB. The HBB structure is completed within 30 min, which coincides with a substrate specificity switch within the flagellar secretion apparatus (indicated by an orange asterisk in the figure) from early to late-substrate secretion. This results in secretion of FlgM and substrates needed during the final phase of flagella assembly. OM: outer membrane, PG: peptidoglycan layer, IM: inner membrane. (B) Expression and secretion of FlgM-SIIIA fusion protein. Secreted FlgM-SIIIA was precipitated using TCA and immunoblots with antibodies against FlgM are shown for cellular and supernatant fractions. Protein bands of native FlgM (open triangle) and FlgM-SIIIA (filled triangle) fusions are marked next to the blot. Construct 1-3 (labeled c1-c3) represent the following protein fusions: c1=H6-FlgM-TEV-SIIIA, c2=FlgM-TEV-SIIIA-H6, c3=FlgM-H6-TEV-SIIIA. Secretion efficiencies of three FlgM-SIIIA constructs varying in their position of the poly-histidine tag were tested. Secretion levels are shown for TH437 (wt, lane 1), TH4885 (ΔfliF, lane 2), TH5139 (ΔFlgM, lane 3), TH10874 (Para::FlgM-FKF, lane 4), TH15705 (fliA* Para::construct 1, lane 5), TH15706 (fliA* Para::construct 2, lane 6), and TH15707 (fliA* Para::construct 3, lane 7). Wildtype FlgM bands in lane 5-7 were visible upon extended exposure. (C) FlgM-H6-TEV-SIIIA was expressed from the arabinose promoter and secretion was compared in a fliAwt (lane 2), fliA* (H14D, lane 3) and ΔfliCD (lane 4) background. Secretion of wildtype FlgM expressed from its native promoter is shown in lane 1 (TH437, labeled wt).
Figure 1B:
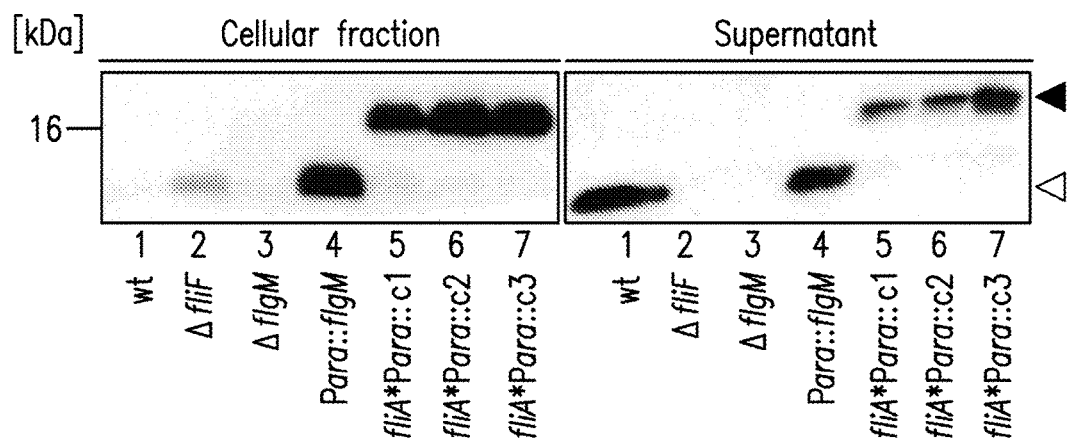
Figure 1C:
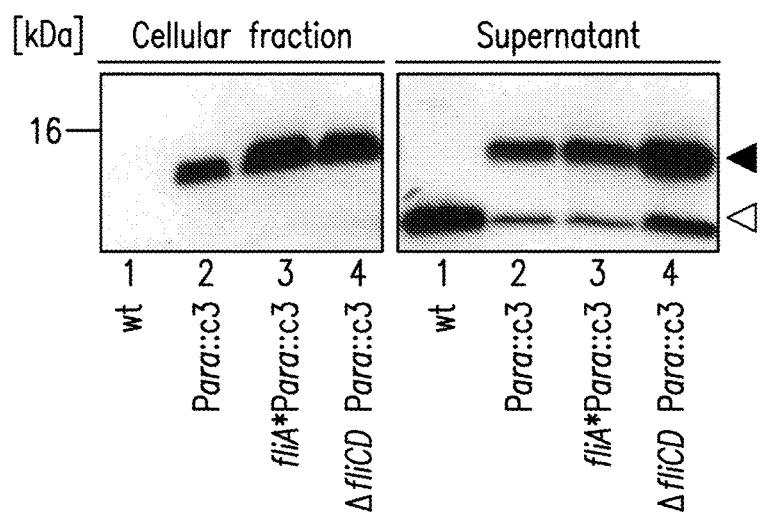

Selective Purification of Recombinant Neuroactive Peptides Using the Flagellar Type III Secretion System In this work the flagellar FlgM protein was utilized as a vector for the secretion of the small, highly stable pharmacologically-active polypeptides that contain a high density of cysteine residues, which form disulfide crosslinks in the mature product. As a proof-of-principle, a bacterial secretion system was engineered for the recombinant expression of μ-conotoxin SIIIA in *Salmonella typhimurium*. Using the flagellar type III secretion (T3S) apparatus, the recombinant conotoxin was selectively secreted into the culture medium, as shown in FIG. 1.

1. Materials and Methods i. Bacterial Strains, Plasmids and Media.

Exemplary bacterial strains that can be used are listed in Table 1. Cells were cultured in Luria-Bertani (LB) media and, when necessary, supplemented with ampicillin (100 μg/ml) or tetracycline (15 μg/ml). The generalized transducing phage of *S. typhimurium* P22 HT105/1 int-201 was used in transductional crosses.

TABLE 1

Strains used in this study

| Strain | Genotype |
|---|---|
| LT2 | Wild type |
| TH2788 | fliY5221::Tn10dTc |
| TH4885 | ΔfliF5629::FKF |
| TH5139 | ΔFlgM5628::FRT |
| TH10874 | ΔFlgM5628::FRT ΔaraBAD923::FlgM-FKF ParaBAD934 |
| TH15360 | ParaBAD1036::FlgM-H6-TEV-SIIIA |
| TH15705 | fliA5225 (H14D) ΔaraBAD1034::H6-FlgM-TEV-SIIIApre |
| TH15706 | fliA5225 (H14D) ΔaraBAD1035::FlgM-TEV-SIIIApre-H6 |
| TH15707 | fliA5225 (H14D) ΔaraBAD1036::FlgM-H6-TEV-SIIIApre |
| TH16229 | ΔaraBAD1064::FlgM-DTA (Y65A) |
| TH16240 | ΔfliCD7901 ΔaraBAD1036::FlgM-H6-TEV-SIIIApre |
| TH16778 | ΔprgH-hilA7791 ΔcheV7829 Δtcp-7829 ΔyhjH7740 Δaer-mcpC7834 PmotA7795 ΔmotA-cheZ7888 P*flhDC7793 ΔFlgMN7753 ΔflgKL7770 Δtrg-7775 ΔycgR7775 |

TABLE 1-continued

Strains used in this study

| Strain | Genotype |
|---|---|
| TH17020 | ΔmcpA7792 ΔfliB-T7771 Δtsr-7828 ecnR4::FKF Δhin-fljA7752 ΔmcpB7835 ΔlrhA ΔydiV252 flgE7742::3xHA ΔprgH-hilA7791 ΔcheV7829 Δtcp-7828 ΔyhjH7740 Δaer-mcpC PmotA7795 ΔmotA-cheZ7888 P*flhD7793 ΔFlgMN7753 ΔflgKL7770 Δtrg-7774 ΔycgR7775 ΔmcpA7792 ΔfljB-T7721 Δtsr-7828 ΔecnR4::FKF Δhin-fljA7752 ΔmcpB7852 ΔlrhA ΔydiV flgE7742::3xHA ΔaraBAD1036::FlgM-H6-TEV-SIIIApre |
| EM170 | ΔprgH-hilA7791 ΔcheV7829 Δtcp-7828 ΔyhjH7740 Δaer-mcpC7834 PmotA7795 ΔmotA-cheZ7888 P*flhD7793 ΔFlgMN7753 ΔflgKL7770 Δtrg-7774 ΔycgR7775 ΔmcpA7792 ΔfljB-T7721 Δtsr-7828 ΔecnR4::FKF Δhin-fljA7752 ΔmcpB7852 ΔlrhA ΔydiV flgE7742::3xHA ΔaraBAD1140::FlgM-H6-TEV-MVIIA |
| EM171 | ΔprgH-hilA7791 ΔcheV7829 Δtcp-7828 ΔyhjH7740 Δaer-mcpC7834 PmotA7795 ΔmotA-cheZ7888 P*flhD7793 ΔFlgMN7753 ΔflgKL7770 Δtrg-7774 ΔycgR7775 ΔmcpA7792 ΔfljB-T7721 Δtsr-7828 ΔecnR4::FKF Δhin-fljA7752 ΔmcpB7835 ΔlrhA ΔydiV flgE7742::3xHA ΔaraBAD1141::FlgM-H6-TEV-GVIA |
| EM172 | ΔprgH-hilA7791 ΔcheV7829 Δtcp-7828 ΔyhjH7740 Δaer-mcpC7834 PmotA7795 ΔmotA-cheZ7888 P*flhD7793 ΔFlgMN7753 ΔflgKL7770 Δtrg-7774 ΔycgR7775 ΔmcpA7792 ΔfljB-T7721 Δtsr-7828 ΔecnR4::FKF Δhin-fljA7752 ΔmcpB7835 ΔlrhA ΔydiV flgE7742::3xHA ΔaraBAD1142::FlgM-H6-TEV-(Contulakin-G) |
| EM173 | ΔprgH-hilA7791 ΔcheV7829 Δtcp-7828 ΔyhjH7740 Δaer-mcpC7834 PmotA7795 ΔmotA-cheZ7888 P*flhD7793 ΔFlgMN7753 ΔflgKL7770 Δtrg-7774 ΔycgR7775 ΔmcpA7792 ΔfljB-T7721 Δtsr-7828 ΔecnR4::FKF Δhin-fljA7752 ΔmcpB7835 ΔlrhA ΔydiV flgE7742::3xHA ΔaraBAD1143::FlgM-H6-TEV-αVc1.1 |
| EM174 | ΔprgH-hilA7791 ΔcheV7829 Δtcp-7828 ΔyhjH7740 Δaer-mcpC7834 PmotA7795 ΔmotA-cheZ7888 P*flhD7793 ΔFlgMN7753 ΔflgKL7770 Δtrg-7774 ΔycgR7775 ΔmcpA7792 ΔfljB-T7721 Δtsr-7828 ΔecnR4::FKF Δhin-fljA7752 ΔmcpB7835 ΔlrhA ΔydiV flgE7742::3xHA ΔaraBAD1147::FlgM-H6-TEV-(Conantokin-G) |
| EM175 | ΔprgH-hilA7791 ΔcheV7829 Δtcp-7828 ΔyhjH7740 Δaer-mcpC7834 PmotA7795 ΔmotA-cheZ7888 P*flhD7793 ΔFlgMN7753 ΔflgKL7770 Δtrg-7774 ΔycgR7775 ΔmcpA7792 ΔfljB-T7721 Δtsr-7828 ΔecnR4::FKF Δhin-fljA7752 ΔmcpB7835 ΔlrhA ΔydiV flgE7742::3xHA ΔaraBAD1148::FlgM-H6-TEV-SIIIAmat |
| EM176 | ΔprgH-hilA7791 ΔcheV7829 Δtcp-7828 ΔyhjH7740 Δaer-mcpC7834 PmotA7795 ΔmotA-cheZ7888 P*flhD7793 ΔFlgMN7753 ΔflgKL7770 Δtrg-7774 ΔycgR7775 ΔmcpA7792 ΔfljB-T7721 Δtsr-7828 ΔecnR4::FKF Δhin-fljA7752 ΔmcpB7835 ΔlrhA ΔydiV flgE7742::3xHA ΔaraBAD1150::FlgM-H6-TEV-Shk |
| EM177 | ΔprgH-hilA7791 ΔcheV7829 Δtcp-7828 ΔyhjH7740 Δaer-mcpC7834 PmotA7795 ΔmotA-cheZ7888 P*flhD7793 ΔFlgMN7753 ΔflgKL7770 Δtrg-7774 ΔycgR7775 ΔmcpA7792 ΔfljB-T7721 Δtsr-7828 ΔecnR4::FKF Δhin-fljA7752 ΔmcpB7835 ΔlrhA ΔydiV flgE7742::3xHA ΔaraBAD1149::FlgM-H6-TEV-Chlorotoxin |
| EM178 | ΔprgH-hilA7791 ΔcheV7829 Δtcp-7828 ΔyhjH7740 Δaer-mcpC7834 PmotA7795 ΔmotA-cheZ7888 P*flhD7793 ΔFlgMN7753 ΔflgKL7770 Δtrg-7774 ΔycgR7775 ΔmcpA7792 ΔfljB-T7721 Δtsr-7828 ΔecnR4::FKF Δhin-fljA7752 ΔmcpB7835 ΔlrhA ΔydiV flgE7742::3xHA ΔaraBAD1144::FlgM-H6-TEV-GsMTx4 |
| EM179 | ΔprgH-hilA7791 ΔcheV7829 Δtcp-7828 ΔyhjH7740 Δaer-mcpC7834 PmotA7795 ΔmotA-cheZ7888 P*flhD7793 ΔFlgMN7753 ΔflgKL7770 Δtrg-7774 ΔycgR7775 ΔmcpA7792 ΔfljB-T7721 Δtsr-7828 ΔecnR4::FKF Δhin-fljA7752 ΔmcpB7835 ΔlrhA ΔydiV flgE7742::3xHA ΔaraBAD1145::FlgM-H6-TEV-Calciseptine | ii. Construction of Chromosomally Expressed FlgM-Toxin Fusions.

SIIIA was amplified in a de novo fill-in PCR-reaction using a long primer SIIIA_long_fw (CAGAACTGCTG-CAACGGCGGCTGCAGCAGCAAATGGTGCCGCGAT-CATGCG CGCTGCTGCGGCCGC; SEQ ID NO:1) covering all 66 base pairs encoding for SIIIA (QNCCNGGCSSKWCRDHARCCGR; SEQ ID NO:2). The SIIIA sequence was designed according to the optimal codon usage of Salmonella typhimurium. The 66 bp sequence was duplexed with the help of a short reverse primer (SIIIA_short_rv: GCGGCCGCAGCAGCGCG-CATG; SEQ ID NO:3) initiating the fill-in from the 3' end of the template primer.

A cleavage site for the TEV protease (ENLYFQG; SEQ ID NO:4) and a poly-histidine tag (H6 encoded by (CAT-CAC)$_3$; SEQ ID NO:5) were inserted during amplification of flgM and SIIIA at various positions, resulting in three different construct (named construct 1-3).

In the following, the construction procedure of construct 1 will be explained exemplarily in more detail, Construct 2 and construct 3 were designed accordingly (see Table 2 for primer sequences). The flgM gene was amplified from genomic DNA (TH2788) using forward primers 1_HS1_FlgM_fw and reverse primers 1_HS2_FlgM_rv. The reverse primers encoded for an 18 bp overhang that was homologous to the 5' SIIIA sequence (see above). To increase the length of the homologous region, SIIIA was amplified from the previous synthesized template with primers 1_HS3_SIIIA_fw and 1_HS4_SIIIA_rv—adding an additional 10 bp overlap with homology to the sequence of the TEV protease cleavage site. The PCR products of FlgM and SIIIA were purified and used in a subsequent fusion PCR as a template together with forward primers 1_HS1_FlgM_fw and reverse primers 1_HS4_SIIIA_rv. This method allows the fusion of two PCR products that share a homology of (in case of construct 1) 28 base pairs, resulting in one long flgM-SIIIA fusion construct. All constructs contained a 5'-BamH1 and a 3'-EcoR1 restriction site for cloning into pUC18, resulting in the subcloning vectors (pHS1 (pUC18 BamHI-His6-FlgM-TEV-SIIIA-EcoRI), pHS2 (pUC18 BamHI-FlgM-TEV-SIIIA-His6-EcoRI) and pHS3 (pUC18 BamHI-FlgM-His6-TEV-SIIIA-EcoRI).

TABLE 2

Primer sequences for toxin construction.

| Primer name | Sequence |
|---|---|
| SIIIA_long_fw | CAGAACTGCTGCAACGGCGGCTGCAGCAGCAAATGGTG CCGCGATCATGCGCGCTGCTGCGGCCGC (SEQ ID NO: 1) |
| SIIIA_short_rv | GCGGCCGCAGCAGCGCGCATG (SEQ ID NO: 3) |
| 1_HS1_FlgM_fw | cgggatcccgATGCATCACCATCACCATCACATGAGCATTGA CCGTACCTC (SEQ ID NO: 6) |

TABLE 2-continued

Primer sequences for toxin construction.

| Primer name | Sequence |
|---|---|
| 1_HS2_FlgM_rv | CCGTTGCAGCAGTTCTGgccctgaaaatacaggttttcTTTACTCTGT AAGTAGCTCTG (SEQ ID NO: 7) |
| 1_HS3_SIIIA_fw | ttttcagggcCAGAACTGCTGCAACGGCGG (SEQ ID NO: 8) |
| 1_HS4_SIIIA_rv | ggaattccTTAGCGGCCGCAGCAGCGCG (SEQ ID NO: 9) |
| DTA-FlgM_fw | ACTCGCTCATTCGCGAGGCGCAGAGCTACTTACAGAGT AAAGGCAGCTCTCACCACCACC (SEQ ID NO: 10) |
| DTA-FlgM_rv | TTCATCAACGCGCCCCCCATGGGACGCGTTTTTAGAGGC ATTAACGGTTACCTGCACAAG (SEQ ID NO: 11) |
| 2_HS5_FlgM_fw | cgggatcccgATGAGCATTGACCGTACCTC (SEQ ID NO: 12) |
| 2_HS6_FlgM_rv | CCGTTGCAGCAGTTCTGgccctgaaaatacaggttttcTTTACTCTGT AAGTAGCTCTGC (SEQ ID NO: 13) |
| 2_HS7_SIIIA_fw | ttcagggcCAGAACTGCTGCAACGGC (SEQ ID NO: 14) |
| 2_HS8_SIIIA_rv | ggaattccTTAGTGATGGTGATGGTGATGGCGGCCGCAGCA GCGCGCAT (SEQ ID NO: 15) |
| 3_HS9_FlgM_rv | gccctgaaaatacaggttttcGTGATGGTGATGGTGATGTTACTCT GTAAGTAGCTCTG (SEQ ID NO: 16) |
| 3_HS10_SIIIA_fw | TCACgaaaacctgtattttcagggcCAGAACTGCTGCAACGGCGGC (SEQ ID NO: 17) |
| 3_HS11_SIIIA_rv | ggaattccTTAGCGGCCGCAGCAGCGCG (SEQ ID NO: 18) |
| 1A-MVIIA_fw | TGCAAAGGTAAAGGTGCAAAATGTAGCCGTCTGATGTA TGATTGTTGTACCGGTAGCTGT (SEQ ID NO: 19) |
| 1B-MVIIA_rv | TTAACATTTACCGCTACGACAGCTACCGGTACAACAAT (SEQ ID NO: 20) |
| 1C-MVIIA_homology_fw | ACATCACCATCACCATCACgaaaacctgtattttcagggcTGCAAAG GTAAAGGTGCAAA (SEQ ID NO: 21) |
| 1D-MVIIA_homology_rv | ttcatcaacgcgccccccatgggacgcgttttagaggcaTTAACATTTACCGC TACGAC (SEQ ID NO: 22) |
| 2A-GVIA_fw | TGTAAAAGTCCGGGTAGCAGCTGTAGCCCGACCAGCTA TAATTGTTGTCGTAGCTGTAAT (SEQ ID NO: 23) |
| 2B-GVIA_rv | TTAATAGCAACGTTTGGTATACGGATTACAGCTACGAC AACAAT (SEQ ID NO: 24) |
| 2C-GVIA_homology_fw | ACATCACCATCACCATCACgaaaacctgtattttcagggcTGTAAAA GTCCGGGTAGCAG (SEQ ID NO: 25) |
| 2D-GVIA_homology_rv | ttcatcaacgcgccccccatgggacgcgttttagaggcaTTAATAGCAACGTT TGGTAT (SEQ ID NO: 26) |
| 3A-Contulakin-G_fw | GAAAGCGAAGAAGGTGGTAGCAACGCAACCAAAAAAC CGTATATTCTGTAA (SEQ ID NO: 27) |
| 3B-Contulakin-G_rv | TTACAGAATATACGGTTTTTTGGTTGCGTTGCTACCACC TTCTTCGCTTTC (SEQ ID NO: 28) |
|

TABLE 2-continued

Primer sequences for toxin construction.

| Primer name | Sequence |
| --- | --- |
| 4D-alpha-Vc1.1_homology_rv | ttcatcaacgcgc TABLE 2-continued Primer sequences for toxin construction.

| Primer name | Sequence |
|---|---|
| 8Bb-Chlorotoxin_rv | ttaACGACACAGACACTGCGGACCATAACAT (SEQ ID NO: 59) |
| 8C-Chlorotoxin_homology_fw | ACATCACCATCACCATCACgaaaacctgtattttcagggcATGTGTA TGCCGTGTTTTAC (SEQ ID NO: 60) |
| 8D-Chlorotoxin_homology_rv | ttcatcaacgcgcccccatgggacgcgttttagaggcattaACGACACAGACA CTGCG (SEQ ID NO: 61) |

All flgM-SIIIA fusions were amplified from the respective subcloning vectors with primers having homologous regions for the native flgM locus or the arabinose locus (ΔaraBAD), respectively. Chromosomal insertions were constructed using λ-Red mediated recombination.

The expression of SIIIA in *Salmonella* resulted in a recombinant peptide that was lacking posttranslational modifications that are usually present under physiological conditions. Those include a neutral N-terminal pyroglutamate, C-terminal amidation and cleavage of a two-residue fragment—named SIIIApre. However, according to functional studies on the related μ-conotoxin GIIIA, the potency of SIIIA is determined by the lysine at position 11 and therefore not affected by any N- and C-terminal sequence variations.

All other toxins from various organisms (snails, spiders, snakes, and sea anemone) were constructed correspondingly, and their sequences are listed in Table 3 and Table 2.

TABLE 3

Toxins used in this study.

| Toxin name | Organism | Species | Toxin size [aa] | Amino acid sequence (w/o modifications) |
|---|---|---|---|---|
| ω-MVIIA | Cone snail | *Conus magus* | 25 | CKGKGAKCSRLMYDCCTGSCR SGKC (SEQ ID NO: 62) |
| ω-GVIA | Cone snail | *Conus geographus* | 27 | CKSPGSSCSPTSYNCCRSCNPY TKRCY (SEQ ID NO: 63) |
| Contulakin-G | Cone snail | *Conus geographus* | 16 | ESEEGGSNATKKPYIL (SEQ ID NO: 64) |
| α-Vc1.1 | Cone snail | *Conus victoriae* | 16 | GCCSDPRCNYDHPEIC (SEQ ID NO: 65) |
| Conantokin-G | Cone snail | *Conus geographus* | 17 | GEEELQENQELIREKSN (SEQ ID NO: 66) |
| μ-SIIIAmat | Cone snail | *Conus striatus* | 20 | ENCCNGGCSSKWCRDHARCC (SEQ ID NO: 67) |
| μ-SIIIApre | Cone snail | *Conus striatus* | 22 | QNCCNGGCSSKWCRDHARCC GR (SEQ ID NO: 68) |
| Shk | Sea anemone | *Stichodactyla helianthus* | 35 | RSCIDTIPKSRCTAFQCKHSMK YRLSFCRKTCGTC (SEQ ID NO: 69) |
| Chlorotoxin | Scorpion | *Leiurus quinquestriatus* | 36 | MCMPCFTTDHQMARKCDDCC GGKGRGKCYGPQCLCR (SEQ ID NO: 70) |
| GsMTx4 | Spider | *Grammostola spatulata* | 35 | GCLEFWWKCNPNDDKCCRPK LKCSKLFKLCNFSSG (SEQ ID NO: 71) |
| Calciseptine | Snake | *Dendroaspis p. polylepis* | 60 | RICYIHKASLPRATKTCVENTC YKMFIRTQREYISERGCGCPTA MWPYQTECCKGDRCNK (SEQ ID NO: 72) |
| DTA Y65A | Bacterium | *Corynebacterium diphtheriae* | 190 | GADDVVDSSKSFVMENFSSYH GTKPGYVDSIQKGIQKPKSGTQ GNYDDDWKGFYSTDNKYDAA GASVDNENPLSGKAGGVVKVT YPGLTKVLALKVDNAETIKKEL GLSLTEPLMEQVGTEEFIKRFG |

TABLE 3-continued

Toxins used in this study.

| Toxin name | Organism | Species | Toxin size [aa] | Amino acid sequence (w/o modifications) |
| --- | --- | --- | --- | --- |
| | | | | DGASRVVLSLPFAEGSSSVEYIN NWEQAKALSVELEINFETRGK RGQDAMYEYMAQACAGNR (SEQ ID NO: 73) |

Fragment A of the diphtheria toxin (DTA Y65A) was amplified from plasmid pTH794 with primers DTA-FlgM_fw (ACTCGCTCATTCGCGAGGCGCAGAGCTACTTACAGAGTAAAGGCAGCTCTC ACCACCACC; SEQ ID NO:10) and DTA-FlgM_rv (TTCATCAACGCGCCCCCCATGGGACGCGTTTTTAGA GGCATTAACGGTTACCTGCACAAG; SEQ ID NO:11). DTA amplification included a poly-histidine-tag (H6) with a GSS-linker before the His-tag and a SSGLVPR-linker between the His-tag and the first amino acid of DTA. DTA was chromosomally inserted by 2-Red-mediated recombination. The insertion was carried out in a ΔaraBAD::FlgM$^+$ background. DTA was targeted in front of the flgM stop codon resulting in a translational FlgM-DTA fusion.

iii. Recombinant Expression and Purification of SIIIA Conotoxin.

Strains expressing SIIIA conotoxin fusions were picked from a fresh single colony and grown in 10 ml LB overnight. The overnight cultures were diluted 1:100 into 1 1 fresh media and grown for six hours. If appropriate, SIIIA expression was induced after the first two hours by addition of 0.2% arabinose. Cells were pelleted by centrifugation (7,000 rpm), and the supernatant containing FlgM-SIIIA was passed through a 0.22 μm polyethersulfone filter (Corning, N.Y., USA)—a low protein binding membrane for removal of residual bacteria. For further purification, a gravity-flow column (Bio-Rad) packed with 3 g Ni-IDA resin (Protino Ni-IDA, Machery-Nagel) was used and affinity tagged proteins were eluted under native conditions at pH 7.5 with a buffer containing 250 mM imidazole.

iv. Secretion Assay.

Overnight cultures were diluted 1:100 in LB and grown for two hours at 37° C. before inducing the expression of the respective FlgM-toxin fusion by adding 0.2% L-arabinose. Cells were kept at 37° C. for an additional four hours, while the fusion proteins were expressed. After a total of six hours, the optical density (OD) at 600 nm was determined for all strains.

Two ml aliquots of the resulting cell culture were centrifuged for 10 min at 4° C. and 7,000 rpm to obtain, for each aliquot, a pellet and supernatant. The supernatant was filtered through a low protein binding filter with 0.2 μm pore size (Acrodisk Syringe Filter, PALL Life Sciences) to remove remaining cells. Alternatively, aliquots were centrifuged twice at maximum speed to remove residual cells. Secreted proteins in the filtered or twice-centrifuged supernatant were precipitated by addition of TCA (10% final concentration). The supernatant samples were resuspended in 2×SDS sample buffer (100 mM Tris pH 6.8, 4% SDS, 10% glycerol, 2% β-mercaptoethanol, 25 mM EDTA, 0.04% bromophenol blue) and adjusted to 20 $OD_{600}$ units per μl. The cellular, pellet fraction was suspended in 2×SDS sample buffer, whose volume was adjusted to yield 20 $OD_{600}$ units per μl.

v. SDS PAGE and Western Blotting.

Expressed FlgM-toxin fusions of whole-cell lysate and cultural supernatant were subjected to SDS polyacrylamide gel electrophoresis and analyzed by immunoblotting using polyclonal anti-FlgM and polyclonal anti-FliK antibodies (rabbit) for detection. Antigen-antibody complexes were visualized by chemiluminescent or infrared detection using the LI-COR Odyssey imaging system. For chemiluminescent development, secondary goat α-rabbit antibodies (Bio-Rad) conjugated with horseradish peroxidase (HRP) and an ECL detection kit (Amersham Biosciences) were used. For infrared detection, secondary anti-rabbit-IRDye690 (LI-COR) was used. Densitometric measurements of FlgM-SIIIA and FliK bands were performed using ImageJ 1.45s for Mac OS X.

vi. TEV Protease Cleavage.

SIIIA was cleaved off flagellar secretion substrates using AcTEV Protease (Invitrogen). 450 U of TEV protease was added to 15 ml of the elution fraction, which corresponds to the secreted proteins from a 750 ml culture. Cleavage was performed overnight at room temperature in elution buffer containing 1 mM dithiothreitol (DTT) and 0.5 mM EDTA.

vii. Folding of SIIIA.

Recombinant SIIIA was folded in 0.1 M Tris buffer, pH 7.5 using 1 mM oxidized glutathione (GSSG) and 0.1 mM EDTA. The folding reaction was allowed to proceed overnight at room temperature and was quenched by the addition of formic acid to a final concentration of 8%.

viii. Solid Phase Extraction of SIIIA.

$C_{18}$ Solid phase extraction columns (Supelclean LC-18, Supelco) were used to remove the oxidized peptide from the other components of the folding and cleavage reactions. The isolated peptide was then dried and purified by HPLC on a Waters 600 chromatograph, equipped with a dual-wavelength absorbance detector and a Vydac $C_{18}$ analytical column. The HPLC separation was run with a linear gradient from 4.5% to 31.5% (aq) acetonitrile (0.9% change per minute), maintaining 0.1% TFA throughout. This allowed purification of the correct folding product; mass was validated by matrix-assisted laser desorption/ionization time-of-flight (MALDI-TOF) mass spectrometry.

ix. Electrophysiology of Mammalian $Na_V$ Channels.

The functional activity of recombinant SIIIA was assessed electrophysiologically with *Xenopus* oocytes expressing $Na_V1.2$. Briefly, the oocyte was placed in a 30 μl recording chamber perfused with ND96 and two-electrode voltage clamped. A holding potential of −80 mV was used, and activation of sodium channels was achieved by stepping the potential to −10 mV for 50 ms every 20 seconds. Exposure to toxin was performed in a static bath to conserve peptide, as follows. Prior to toxin application, the perfusion of the bath was halted, and control responses were recorded. Peptide (3 μl at 10-times the final concentration) was then applied to the bath, which was stirred for 5 seconds using a micropipette. Recordings of the onset of block by the peptide were obtained for about 20-min, after which the perfusion with ND96 was resumed to remove unbound peptide while the rate of recovery from block was monitored for about 20 minutes, The time course of the onset of block was fit to a single-exponential function to obtain the observed rate constant of block, $k_{obs}$. The rate of recovery from block during peptide washout was too slow to measure by curve fitting, so $k_{off}$ was estimated from the level of recovery after 20 min of washing and assuming exponential decay of block. All recordings were obtained at room temperature.

x. Immunostaining.

Fluorescent microscopy analysis was performed.

2. Results and Discussion.

Figure 2A:
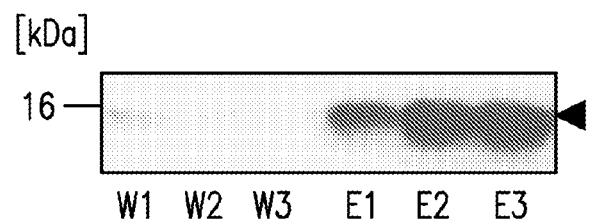
FIG. 2 shows purification and electrophysiology of recombinant conotoxin SIIIA and secretion of toxins from various organisms via the flagellar T3SS. (A) The supernatant of a strain expressing and secreting recombinant SIIIA fused to FlgM (TH15707 fliA* (H14D) ΔaraBAD1036::FlgM-H6-TEV-SIIIA) was filtered and bound to a Ni2+-IDA column as described in Example 1. The matrix was washed after binding (W1-W3) and FlgM-SIIIA was eluted in three steps with imidazole-containing elution buffer (E1-E3). For Western blot detection, samples were TCA precipitated. Due to the increased FlgM-SIIIA concentration in the elution fractions, only 1/10th of the volume was used for TCA precipitation of elution fractions 1-3. (B) Recombinant SIIIA blocks voltage-gated sodium channel NaV1.2. A Xenopus oocyte expressing rat NaV1.2 was exposed to 10 μM rSIIIA while sodium currents were monitored as described in Example 1. Currents recorded before toxin exposure (control, gray trace), and following 20-min exposure to 10 μM rSIIIA (black trace). Each trace represents the average of five responses. The difference of the peak values between the two traces corresponds to the inhibitory effect rSIIIA has on channel Na V1.2. (C) FlgM-H6-TEV was translationally fused to six different toxins from cone snails, and one toxin each from sea anemone, scorpion, spider, and snake, and FlgM-H6 was fused to (D) the Corynebacterium diphtheria (see also Table 3 for detailed list). Toxins were expressed in a Salmonella poly-hook background. Secretion of diphtheria toxin fragment A from *Salmonella* strain TH16229 was tested using three independent biological replicates (labeled 1-3). Secretion of recombinant toxins was performed as described before.
Figure 2B:
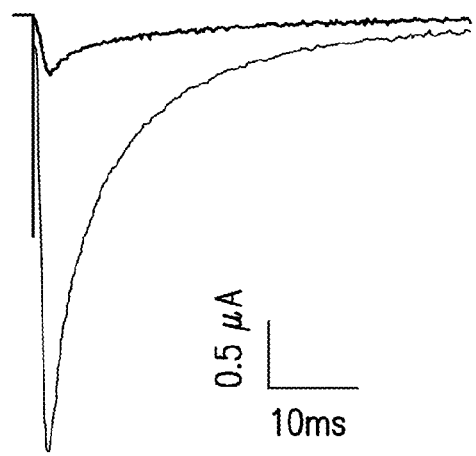
Figure 2C:
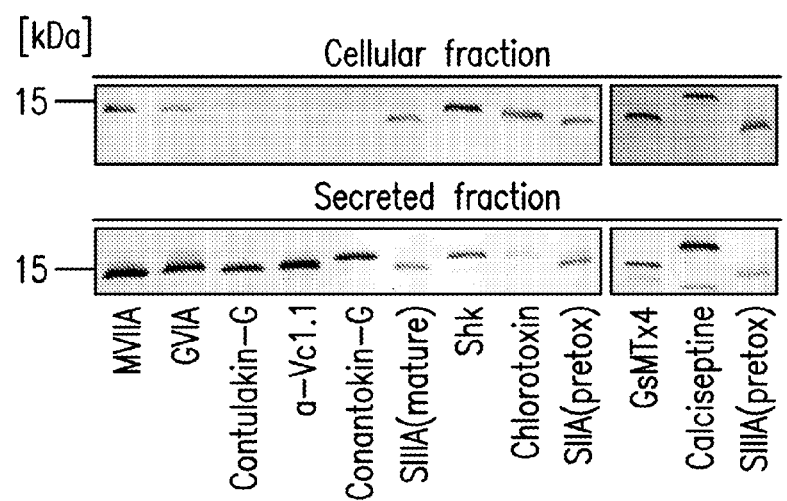
Figure 2D:
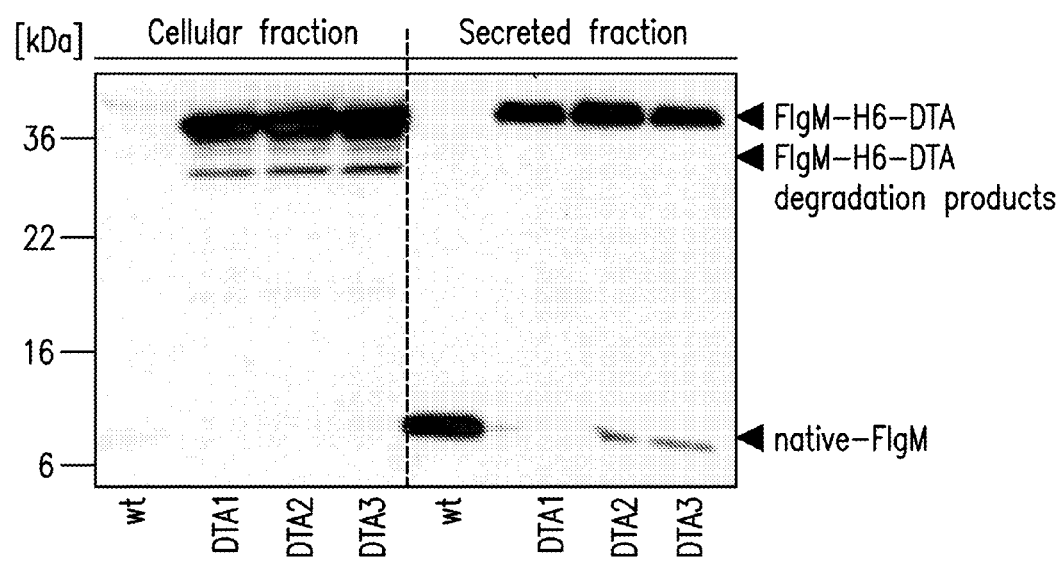
Figure 3A:
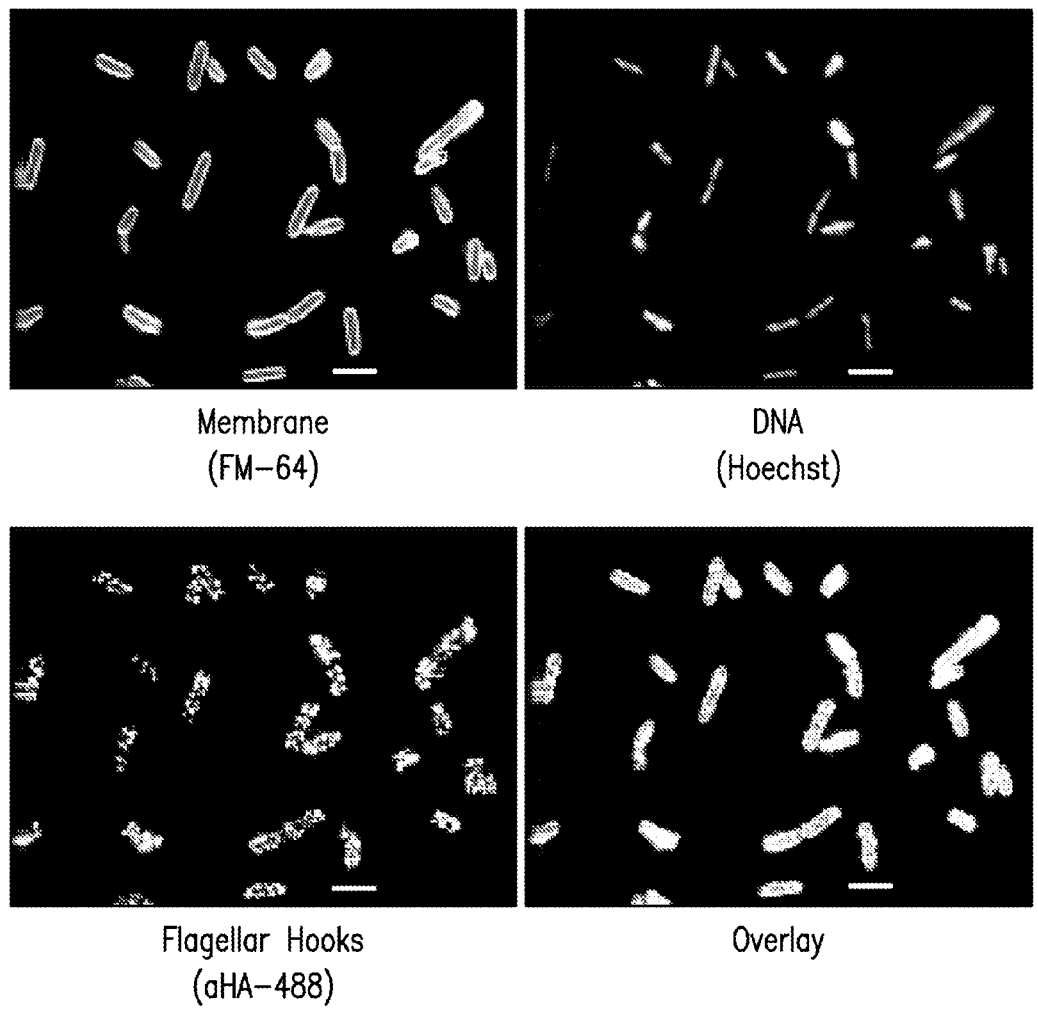
Figure 3B:
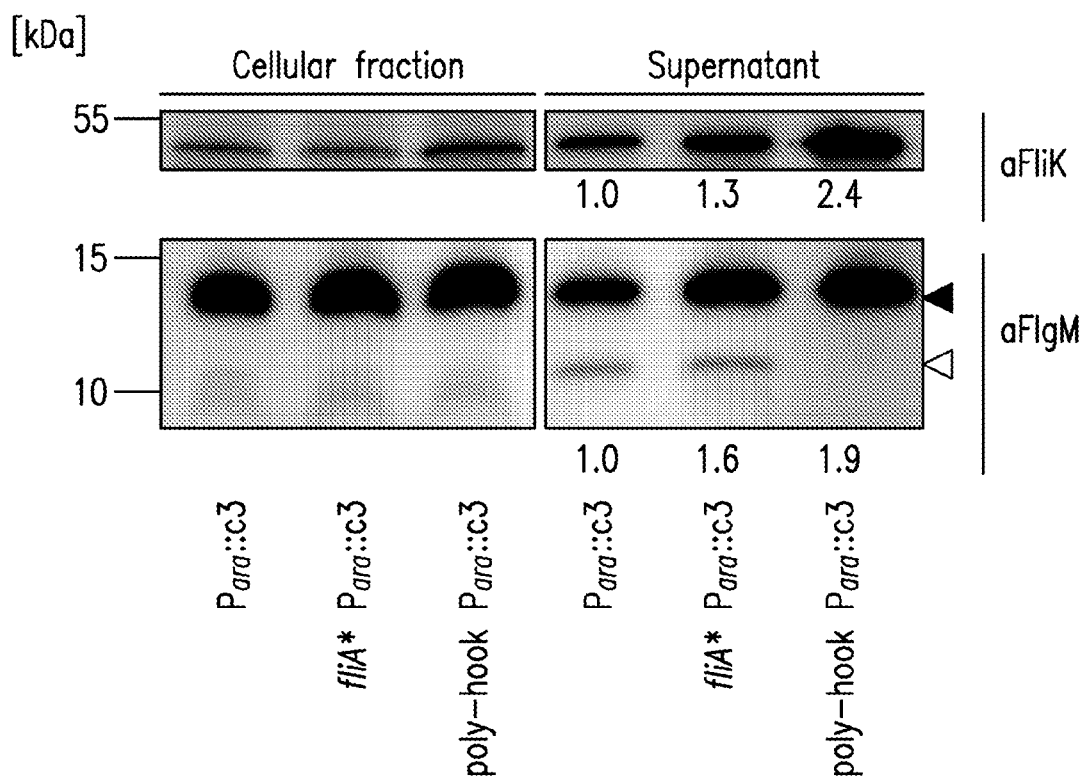

Conotoxins are synthesized in the venom duct of marine cone snails and target ion channels, including voltage-gated sodium channels (VGSCs). SIIIA is a μ-conotoxin from *Conus striatus* that inhibits tetrodotoxin (TTX)-resistant VGSCs in frog and TTX-sensitive VGSCs in rodents. The μ-Conotoxin SIIIA binds to site 1 of the α-subunit of VGSCs and thereby occludes the channel pore and blocks sodium conductance. Under physiological conditions two forms of SIIIA exist: a precursor form and a mature peptide, which has been modified by processing the C-terminal glycine-arginine residues to an amino group and changing the N-terminal glutamine residue to pyroglutamate. Herein, two forms of SIIIA were recombinantly expressed, the precursor peptide and a peptide that most closely resembles the physiological mature form (N-terminal glutamate instead of pyroglutamate). In mammalian preparations, μ-SIIIA effectively blocks neuronal sodium channels such as $Na_V1.2$ and 1.6, and the skeletal muscle subtype $Na_V1.4$. Because SIIIA targets VGSCs and has potent analgesic activity in mice, it can be used for medical research and drug discovery. The fundamental advantage in developing a T3SS bacterial expression system is that after translation the polypeptides translocate through a narrow secretion channel in the flagellar structure and thereby bypass the problem of aggregation in inclusion bodies. Polypeptide secretion prevents intermolecular aggregation in the cytoplasm. Intramolecular disulfide bonds form as the polypeptide chain exits the reductive environment of the bacterial cytoplasm and enters an oxidizing extracellular environment.

The efficiency with which different constructs serve as type III secretion substrates was assessed. The SIIIA pretoxin ("μ-SIIIApre" in Table 3 and henceforth referred to as "rSIIIA") is a small 22 amino acid peptide which was fused to FlgM with an N-terminal TEV cleavage site in front of SIIIA. In order to ensure proper secretion and to diminish the possibility of interference with the structural secretion signal of FlgM, three different constructs were designed with a poly-histidine tag at different positions. All constructs were chromosomally expressed from the arabinose-inducible promoter $P_{araBAD}$ FIG. 1B shows the secretion profile of all three constructs. Construct 3 (FlgM-H6-TEV-SIIIA) displayed the most prominent secretion product; construct 2 (FlgM-TEV-SIIIA-H6) exhibited the lowest secretion level. This secretion ranking was consistent in all backgrounds tested, some of which carried a mutation (fla* or H14D) in the $\sigma^{28}$ structural gene fliA that enhances stability of this FlgM secretion-chaperone protein. FlgM levels were very low in a strain unable to form a flagellar structure (ΔfliF) compared to those in a wild type strain.

The flagellum-specific transcription factor $\sigma^{28}$ acts as a chaperone to facilitate FlgM secretion. As shown in Figure Cc, $\sigma^{28}$ H14D, with its enhanced stability, increased levels of intracellular and secreted FlgM-SIIIA. $\sigma^{28}$ H41D also increases FlgM stability. This is the cause of the increased levels of FlgM-SIIIA in the fliA* background (FIG. 1C, lanes 2 and 3). The effect of removing the late flagellar secretion substrates (and potential secretion competitors) FliC and FliD (ΔfliCD) was also tested. The fliC and fliD genes are divergently transcribed. However, the fliD gene is in an operon with fliT, which encodes the FliT inhibitor of all flagellar gene expression. Thus, the ΔfliCD deletion results in removal of secretion competitors for FlgM in addition to increasing the number of flagellar basal structures. The net effect was increased production and secretion of both FlgM and FlgM-SIIIA from the cell (FIG. 1C, lanes 2 and 4).

As FlgM-H6-TEV-SIIIA showed the highest level of secretion, this construct was used for further purification experiments. The SIIIA fusion was expressed from an arabinose inducible promoter to allow synchronization of the high level of expression with completion of the flagellar secretion systems. Secreted FlgM-H6-TEV-SIIIA was separated from the bacterial cell culture by centrifugation and was obtained from the supernatant under native conditions by nickel-affinity chromatography. As shown in FIG. 2A, FlgM-H6-TEV-SIIIA efficiently bound to the Ni-IDA resins and was eluted with imidazole-containing elution buffer. After concentration of the eluted fraction, rSIIIA was cleaved from the FlgM-H6-TEV secretion signal using TEV protease. Western Blot analysis and Coomassie staining demonstrated that TEV cleavage was complete after 3 hours at room temperature.

As with all cysteine-rich peptides, the formation of the native disulfide bonds is a process involved in generating biologically active SIIIA. However, the optimal buffer conditions of the TEV protease can be 1 mM dithiothreitol (DTT). This redox agent provides reducing power for the TEV protease but at the same time can reduce S—S bonds in the peptide of interest. For this reason, rSIIIA was refolded prior to electrophysiological analysis. Refolding was carried out in a redox buffer of oxidized and reduced glutathione, allowing thiol-disulfide exchange reactions under conditions that are known to favor formation of the native disulfide bonds.

Tests of the rSIIIA precursor form on *Xenopus* oocytes expressing rat $Na_V1.2$ demonstrated that its functional activity was similar to that of chemically synthesized SIIIA. Sodium currents in response to depolarization were recorded. FIG. 2B presents the results from a representative experiment in which rSIIIA blocked $Na_V1.2$ conductance [compare the peak current of the oocyte before (gray trace) and after rSIIIA exposure (black trace)]. The kinetics of the onset of block following exposure to 10 μM rSIIIA and the recovery from block following its washout were assessed. The observed rate constant for the onset of block ($k_{obs}$) and the rate constant for recovery from block ($k_{off}$) were, respectively, $0.17 \pm 0.04$ $min^{-1}$ and $0.0043 \pm 0.0004$ $min^{-1}$ (mean±SD, n=3 oocytes). The $k_{off}$ value is close to that observed with chemically synthesized SIIIA; however, the $k_{obs}$ value is about six-fold lower than that observed with chemically synthesized SIIIA. The difference in $k_{obs}$ is due to the disparity in the sequences of the two peptides (N-terminal glycine carryover after TEV cleavage and lacking post-translational modifications).

In addition to the secretion of SIIIA pretoxin, several other toxins from various organisms, such as spider (GsMTx4), scorpion (Chlorotoxin), snake (Calciseptine), snails (ω-MVIIA, ω-GVIA, Contulakin-G, α-Vc1.1, Conantokin-G, mature SIIIA) and sea anemone (Shk) were tested for recombinant expression and subsequent secretion in a complementary approach (see Table 3 for a detailed list). Although there were differences in cellular levels and secretion efficiencies, the results shown in FIG. 2C demonstrate that all tested toxins were secreted into the culture supernatant. The secretion of the unstable 190 amino acid long catalytic subunit of diphtheria toxin fused to FlgM was also tested (FIG. 2D). The proteolytic degradation that was observed within the cytosolic fraction did not occur once the protein was secreted from the cell.

For further optimization of the Salmonella secretion strain, a non-motile poly-hook mutant was constructed that had the following characteristics: It lacked the flagellum-related SPI-1 (ΔprgH-hilA,) virulence system, as well as all class 3 flagellar genes (ΔflgKL, ΔfljB-T, ΔFlgMN, Δaer-mcpC, PmotA, ΔmotA-cheZ, ΔmcpA, ΔmcpB, Δtsr) that could diminish or interfere with flagellar type III secretion of the toxin fusion of interest. In addition, the strain harbored a mutation in the flhD promoter (P*flhD) and was deleted for negative regulators of the flagellar master regulator FlhD4C2 (ΔlrhA, ΔydiV, ΔecnR). LrhA acts as a negative regulator of flhDC transcription by directly binding to the promoter region of the master regulator. The EAL domain protein YdiV posttranslationally regulates the activity of FlhD4C2 protein by targeting the complex for ClpXP-dependent degradation and thereby negatively influences FlhDC-dependent flagellar class 2 promoter activity. Transposon insertions in those negative regulators of FlhDC increases flagellar gene expression.

As shown by fluorescent labeling of the flagellar hook structures in FIG. 3A, these mutations resulted in a roughly two-fold increase of flagellar secretion structures per cell compared to wild type cells, which in turn led to a substantial increase in secretion rate of flagellar proteins. Secretion rates of FliK and FlgM-SIIIA (construct 3) were roughly two-fold higher in the poly-hook background compared to those in the wildtype and fliA* backgrounds (FIG. 3B).

A major advantage of this system is the workflow. After induction with arabinose, the bacterial cells express recombinant polypeptides and subsequently secrete the toxin into the media. Contrary to the purification of neuropeptide by traditional methods, this makes it unnecessary to lyse cells in order to purify toxins. Instead, recombinant SIIIA was selectively secreted via the flagellar T3 SS and it accumulated in the culture supernatant. After several hours of production, cells were removed by simple centrifugation and filtration. Other aspects of this system are type III secretion chaperones that facilitate secretion or increase the stability of the secretion substrates. Type III secretion substrates are usually secreted in an unfolded or partially folded state, which is often achieved by interaction of the chaperones with the secondary structure of the secreted protein. Since SIIIA was fused to FlgM, a type III secretion substrate, it was protected from premature folding by interaction with FliA ($\sigma^{28}$), the cognate type III secretion chaperone of FlgM. For the disclosed recombinant expression, full-length FlgM was used, which increased secretion efficiency due to the presence of its FliA chaperone binding site.

The disclosed system provides an easy-to-use method for complicated toxin purification a task that goes beyond yield and solubility of peptides, but also allows the peptides and proteins to be accessible in a correctly folded and active state.

B. Example 2

Analysis of Factors that Affect *Salmonella* FlgM Protein Secretion

In this work, a new approach was initiated that uses an expression system that bypasses the inclusion body problem of recombinant small peptide expression. It exploits the flagellar secretion system of *Salmonella enterica* serovar *Typhimurium* (*Salmonella typhimurium*) that has been shown to export non-flagellar proteins if fused to flagellar secretion signals, e.g. hook protein FlgE or flagellin FliC. The flagellar secretion system is a member of a family of bacterial type III secretion systems that selectively secrete proteins from the cytoplasm to the external medium. Almost all type III secretion systems characterized thus far are either required for the secretion of virulence determinants for a number of plant and animal pathogens or for the secretion of proteins required for the structure and function of the bacterial flagellum. The bacterial flagellum is composed of an external helical filament, extending many body lengths from the cell surface, attached to a rotary motor embedded within the cell wall and membranes. For *Salmonella*, a chemosensory system controls the clockwise and counter-clockwise direction of flagellar rotation, which allows the bacterium to migrate towards attractants, such as nutrients, or away from repellents that are harmful to the bacterium.

The specificity for flagellar substrate secretion is primarily determined by an N-terminal peptide secretion signal that has a disordered structure. Many secretion substrates also require a specific secretion chaperone to facilitate secretion. One flagellar secretion substrate, FlgM, is a regulatory protein that couples flagellar assembly to gene expression. $\sigma^{28}$, a transcription factor specific for flagellar promoters, directs transcription of genes specifically needed after completion of the flagellar motor and thereby induces expression of the filament and chemosensory genes. FlgM binds $\sigma^{28}$ and prevents its association with RNA polymerase. Completion of the flagellar motor results in a change in substrate specificity of the flagellar secretion apparatus, switching from secretion of proteins required for motor assembly to late substrate secretion of proteins needed in filament assembly. FlgM itself is a late secretion substrate and its secretion releases $\sigma^{28}$, enabling it to transcribe the filament and chemosensory genes only upon completion of the motor. At the same time, the $\sigma^{28}$ transcription factor acts as the secretion chaperone that facilitates the secretion of its inhibitor, FlgM.

In this work the flagellar FlgM protein was utilized as a vector for the secretion of the small, highly stable pharmacologically-active polypeptides that contain a high density of cysteine residues, which form disulfide crosslinks in the mature product. A bacterial secretion system was created for the recombinant expression of μ-conotoxin SIIIA in *Salmonella typhimurium*. Using the flagellar type III secretion (T3S) apparatus, the recombinant conotoxin was selectively secreted into the culture medium.

1. Materials and Methods i. Bacteria Strains and Growth Conditions.

All strains used in this study are derivatives of LT2, a wild-type strain *Salmonella enterica* serovar *Typhimurium*, and are listed in Table 4. All strains were constructed during the course of this study. Strain construction utilized either P22-mediated generalized transduction or λ Red-mediated targeted mutagenesis. For strains with the flhDC operon expressed from its native promoter, flagellar gene expression was induced by 100-fold dilution from overnight stationary cultures into fresh LB medium (10 g Bacto tryptone, 5 g Bacto Yeast Extract and 5 g NaCl per liter). For strains with the flhDC operon expressed from the tetA promoter of transposon Tn10 ($\Delta P_{flhDC}$8089::tetR-PtetA), flagellar gene expression was induced by addition of the tetracycline analog anhydro-tetracycline (1 μg/ml). For all strains used in this study, the arabinose utilization operon araBAD, was replaced with the FlgM⁺ gene or FlgM gene fusions FlgM-6His-TEV-δ-SVIE or FlgM-6His-ETK-δ-SVIE (ΔaraBAD::FlgM⁺, ΔaraBAD::FlgM-6His-TEV-6-SVIE or ΔaraBAD::FlgM-6His-ETK-δ-SVIEI, respectively). This allowed for the induction of FlgM, FlgM-6His-TEV-δ-SVIE and FlgM-6His-ETK-δ-SVIE production from the $P_{araBAD}$ promoter by the addition of L-arabinose to the growth medium. Arabinose was added to 0.2% final concentration two hours after the induction of the flhDC operon. After another 5 hours, the cultures were centrifuged at 10,000 g for 30 min to pellet the cells. The supernatant was filtered with 0.2 μm low protein binding filter (Acrodisk Syringe Filter, PALL Life Sciences) to remove remaining cells. Secreted proteins in the filtered supernatant were precipitated by addition of TCA (trichloroacetic acid) to 10% final concentration. The cell pellet was re-suspended in cold PBS (phosphate buffered saline) containing 5 mM PMSF (phenylmethylsulfonyl fluoride), followed by sonification to lyse the cell suspension. The cell lysate was either analyzed directly for whole cell protein or separated into soluble and insoluble fractions analysis by 30 min centrifugation (15,000 g) at 4° C. To test the effect of different concentration of NaCl and KCl on FlgM secretion, LB medium was prepared without NaCl and either NaCl or KCl were added to the desired concentrations.

TABLE 4

Strains and derivatives of LT2.

| Strain | Genotype |
|---|---|
| TH17831 | ΔaraBAD1124::FlgM-6His-TEV-δ-SVIE |
| TH18353 | ΔaraBAD1124::FlgM-6His-TEV-δ-SVIE DclpX::tetRA |
| TH18500 | ΔaraBAD1156::FlgM⁺ |
| TH18527 | ΔaraBAD1156::FlgM⁺ ΔclpX::tetRA |
| TH18528 | ΔaraBAD1156::FlgM⁺ ΔflhDC::FKF |
| TH18549 | ΔaraBAD1156::FlgM⁺ ΔflhDC::FKF ΔclpX::tetRA |
| TH18624 | ΔaraBAD1156::FlgM⁺ ΔfliA5805::tetRA |
| TH18636 | ΔaraBAD1156::FlgM⁺ fliA8088(H14D, R91C, L207P) |
| TH18647 | ΔaraBAD1124::FlgM-6His-TEV-δ-SVIE Δ$_{flhDC}$8089::(tetR-P$_{tetA}$) |
| TH18649 | ΔaraBAD1156::FlgM⁺ Δ$_{flhDC}$8089::(tetR-P$_{tetA}$) |
| TH18704 | ΔaraBAD1156::FlgM⁺ ΔinvH-sprB::FKF(ΔSpi-1) |
| TH18729 | ΔaraBAD1156::FlgM⁺ ΔfliC7715::tetRA |
| TH18730 | ΔaraBAD1156::FlgM⁺ ΔompT::Km |
| TH18731 | ΔaraBAD1156::FlgM⁺ ΔclpA74::FKF |
| TH18732 | ΔaraBAD1156::FlgM⁺ ΔsseA-ssaU::FKF(ΔSpi-2) |
| TH18733 | ΔaraBAD1156::FlgM⁺ ΔclpP::mini-Tn5 |
| TH18737 | ΔaraBAD1156::FlgM⁺ ΔfliA5999(R91C, L207P) |
| TH18739 | ΔaraBAD1156::FlgM⁺ fliA5225(H14D) |
| TH18752 | ΔaraBAD1156::FlgM⁺ ΔydiV251::tetRA |
| TH18769 | ΔaraBAD1124::FlgM-6His-TEV-δ-SVIE ΔfliT::Km |
| TH18778 | ΔaraBAD1156::FlgM⁺ fliA5228(V33E) |
| TH18780 | ΔaraBAD1156::FlgM⁺ fliA5223(T138I) |
| TH18782 | ΔaraBAD1156::FlgM⁺ fliA5224(E203D) |
| TH18787 | ΔaraBAD1156::FlgM⁺ ΔFlgM5628::FKF |
| TH18788 | ΔaraBAD1156::FlgM⁺ ΔfliT::FKF |
| TH18790 | ΔaraBAD1156::FlgM⁺ ΔflgK7665 |
| TH18793 | ΔaraBAD1156::FlgM⁺ ΔflgL7666 |
| TH18796 | ΔaraBAD1156::FlgM⁺ ΔfliD5630::FRT |
| TH18798 | ΔaraBAD1156::FlgM⁺ ΔdegP::tetRA |
| TH18822 | ΔaraBAD1156::FlgM⁺ ΔcsrA101::Cm |
| TH18823 | ΔaraBAD1156::FlgM⁺ ΔdksA::FKF |
| TH18824 | ΔaraBAD1156::FlgM⁺ ΔrcsB::tetRA |
| TH18830 | ΔaraBAD1124::FlgM-6His-TEV-δ-SVIE ΔrcsB::tetRA |
| TH18850 | ΔaraBAD1156::FlgM⁺ ΔlrhA |
| TH18880 | ΔaraBAD1124::FlgM-6His-TEV-δ-SVIE P$_{flhDC}$7793 |
| TH18881 | ΔaraBAD1156::FlgM⁺ P$_{flhDC}$7793 |
| TH18897 | ΔaraBAD1156::FlgM⁺ fliA5240(L199R) |
| TH18973 | ΔaraBAD1156::FlgM⁺ ΔecnR5::FCF |
| TH19086 | ΔaraBAD1156::FlgM⁺ ΔflgN5626::FKF |
| TH19087 | ΔaraBAD1156::FlgM⁺ ΔfliST5775::FCF |
| TH19099 | ΔaraBAD1156::FlgM⁺ Δhin-fljA7731::tetRA |
| TH19104 | ΔaraBAD1156::FlgM⁺ ΔflgN5626::FKF ΔfliST5775::FCF |
| TH19106 | ΔaraBAD1156::FlgM⁺ ΔfliS5728::FRT |
| TH19113 | ΔaraBAD1156::FlgM⁺ Δhin-fljA7731::tetRA ΔfliC7861::FCF |

TABLE 4-continued

Strains and derivatives of LT2.

| Strain | Genotype |
|---|---|
| TH19116 | ΔaraBAD1164::FlgM-6His-ETK-δ-SVIE |
| TH19118 | ΔaraBAD1164::FlgM-6His-ETK-δ-SVIE PflhDC7793 |
| TH19120 | ΔaraBAD1164::FlgM-6His-ETK-δ-SVIE ΔlrhA ΔecnR4::FRT ΔfliB-T7771 P$_{flhDC}$7793 ΔydiV252 Δhin-fljA7752 ΔFlgMN7753 ΔflgKL7770 |
| TH19145 | ΔaraBAD1164::FlgM-6His-ETK-δ-SVIE P$_{flhDC}$7793 ΔFlgM5628::FKF ΔclpX80::tetRA |
| TH19149 | ΔaraBAD1156::FlgM⁺ ΔflgKL5636::FKF |
| TH19320 | ΔaraBAD1156::FlgM⁺ fliA5226(H14N) |
| TH19323 | ΔaraBAD1156::FlgM⁺ ΔclpA74::FKF ΔflhDC8040::tetRA |
| TH19324 | ΔaraBAD1156::FlgM⁺ ΔclpP::mini-Tn5 ΔflhDC8040::tetRA |
| TH19325 | ΔaraBAD1156::FlgM⁺ ΔdegP::tetRA ΔflhDC::FKF |
| TH19326 | ΔaraBAD1156::FlgM⁺ Δhin-fljA7731::tetRA ΔfliC7861::FCF ΔflgKL5739::FKF |
| TH19481 | ΔaraBAD1156::FlgM⁺ ΔfliS8156 |
| TH19673 | ΔaraBAD1124::FlgM-6His-TEV-δ-SVIE ΔrcsB::tetRA ΔfliT::Km |
| TH19675 | ΔaraBAD1124::FlgM-6His-TEV-δ-SVIE ΔrcsB::tetRA P$_{flhDC}$7793 |
| TH20042 | ΔaraBAD1156::FlgM⁺ Δhin-5717::FRT |
| TH20043 | ΔaraBAD1156::FlgM⁺ Δhin-5717::FRT ΔfliC7715::tetRA |
| TH20044 | ΔaraBAD1124::FlgM-6His-TEV-δ-SVIE P$_{flhDC}$7793 ΔrcsB::tetRA ΔFlgM5628::FKF |
| TH20047 | ΔaraBAD1156::FlgM⁺ fljB$^{enx}$ vh2 |
| TH20048 | ΔaraBAD1124::FlgM-6His-TEV-δ-SVIE fljB$^{enx}$ vh2 |
| TH20049 | ΔaraBAD1156::FlgM⁺ fljB$^{enx}$ vh2 ΔfliC7715::tetRA |
| TH20050 | ΔaraBAD1124::FlgM-6His-TEV-δ-SVIE fljB$^{enx}$ vh2 ΔfliC7715::tetRA |
| TH20053 | ΔaraBAD1156::FlgM⁺ fljB$^{enx}$ vh2 P$_{flhDC}$7768::tetRA |
| TH20055 | ΔaraBAD1156::FlgM⁺ fliA8176 (−18 to +1G replaced by ataaAGGAGGtaaataA) |
| TH20056 | ΔaraBAD1124::FlgM-6His-TEV-δ-SVIE fliA8176 |
| TH20057 | ΔaraBAD1156::FlgM⁺ Δhin-5718::FRT |
| TH20058 | ΔaraBAD1156::FlgM⁺ fljB$^{enx}$ vh2 ΔPflhDC8089::(tetR-P$_{tetA}$) |
| TH20059 | ΔaraBAD1156::FlgM⁺ Δhin-5718::FRT ΔfliC7715::tetRA |
| TH20060 | ΔaraBAD1156::FlgM⁺ ΔfliC7861::FCF fljB$^{enx}$ vh2 ΔP$_{flhDC}$8089::(tetR-P$_{tetA}$) |
| TH20061 | ΔaraBAD1156::FlgM⁺ fliA8177(H14N, R91C, L207P) |
| TH20062 | ΔaraBAD1156::FlgM⁺ fliA8178(GTG: ATG, H14N) |
| TH20063 | ΔaraBAD1156::FlgM⁺ fljB$^{enx}$ vh2 ΔP$_{flhDC}$8089::(tetR-P$_{tetA}$) ΔclpX::Tn10dCm |
| TH20064 | ΔaraBAD1156::FlgM⁺ fljB$^{enx}$ vh2 ΔclpX::Tn10dCm |
| TH20065 | ΔaraBAD1156::FlgM⁺ fljB$^{enx}$ vh2 ΔydiV251::tetRA |
| TH20066 | ΔaraBAD1156::FlgM⁺ fljB$^{enx}$ vh2 ΔfliA5805::tetRA |
| TH20067 | ΔaraBAD1156::FlgM⁺ fljB$^{enx}$ vh2 ΔfliB-T7727::tetRA |
| TH20068 | ΔaraBAD1156::FlgM⁺ fljB$^{enx}$ vh2 ΔfliC7715::tetRA ΔclpX::Tn10dCm |
| TH20069 | ΔaraBAD1156::FlgM⁺ fliA8179(GTG: ATG) |
| TH20071 | ΔaraBAD1156::FlgM⁺ fljB$^{enx}$ vh2 fliA8176 ΔfliC7861::FCF |
| TH20072 | ΔaraBAD1156::FlgM⁺ fljB$^{enx}$ vh2 ΔP$_{flhDC}$8089::(tetR-P$_{tetA}$) ΔfliA5805::tetRA |
| TH20073 | ΔaraBAD1156::FlgM⁺ fljB$^{enx}$ vh2 fliA8176 ΔfliC7861::FCF ΔclpX72::FKF |
| TH20074 | ΔaraBAD1156::FlgM⁺ ΔFlgMN7753 ΔflgKL7770 Δtrg-7774 ΔycgR7775 ΔfliB-T7771 Δhin-fljA7752 fliA8176 |
| TH20075 | ΔaraBAD1124::FlgM-6His-TEV-δ-SVIE fljB$^{enx}$ vh2 ΔfliB-T7727::tetRA |
| TH20077 | ΔaraBAD1124::FlgM-6His-TEV-δ-SVIE fljB$^{enx}$ vh2 ΔclpX80::tetRA |
| TH20078 | ΔaraBAD1156::FlgM⁺ fliA8176 ΔFlgM5794::FCF |
| TH20079 | ΔaraBAD1156::FlgM⁺ fljB$^{enx}$ vh2 ΔP$_{flhDC}$8089::(tetR-P$_{tetA}$) ΔfliA5805::tetRA motA5461::MudJ |
| TH20080 | ΔaraBAD1156::FlgM⁺ fljB$^{enx}$ vh2 ΔP$_{flhDC}$8089::(tetR-P$_{tetA}$) motA5461::MudJ fliA8176 ΔfliC7861::FCF |
| TH20081 | ΔaraBAD1156::FlgM⁺ fliA5226H14N ΔfliC7861::FCF |
| TH20082 | ΔaraBAD1156::FlgM⁺ fljB$^{enx}$ vh2 ΔP$_{flhDC}$8089::(tetR-P$_{tetA}$) motA5461::MudJ fliA5226 ΔfliC7861::FCF |
| TH20083 | ΔaraBAD1124::FlgM-6His-TEV-δ-SVIE fljB$^{enx}$ vh2 ΔP$_{flhDC}$8089::(tetR-P$_{tetA}$) ΔclpX::Tn10dCm | ii. Western Blotting Assays.

Levels of secreted, soluble, insoluble or whole cell proteins were analyzed by Western blot. Expressed DnaK, FlgM and $\sigma^{28}$ levels in the whole-cell lysates and cultural supernatants were determined by SDS-PAGE using 14% gradient gels (BIO-RAD). Analysis of strains containing ΔaraBAD:: FlgM⁺ construct, equivalents of 50 and 100 OD units were loaded for the cellular and supernatant fractions, respectively. In order to analyze strains for FlgM-6His-TEV-δ-SVIE and FlgM-6H-ETK-δ-SVIE secretion, 50 and 300 OD units were loaded for the cellular and supernatant fractions, respectively. Anti-DnaK (mouse), anti-$\sigma^{28}$ and anti-FlgM antibodies (rabbit) were used for detection. DnaK was used as a protein standard control for loading concentration and for the presence of protein in the supernatant due to cell lysis. To visualize antigen-antibody complexes, secondary anti-rabbit-IRDye690 and anti-mouse-IRDye800 antibodies (LI-COR) were used. Densitometric measurements of FlgM, $\sigma^{28}$ and DnaK bands were performed using the LI-COR Odyssey Infrared Imaging System software. All assays were performed in triplicate on culture samples.

iii. Motility Assay.

Motility assays utilized soft agar tryptone plates (per liter: 10 g Bacto tryptone, 5 g NaCl, 3 g Bacto agar). A bacterial colony was picked by toothpick and poked through the soft agar followed by incubation at 37° C. for about 5 hours. If necessary either arabinose (0.2%) or anhydro-tetracycline (1 μg/ml) was added for $P_{araBAD}$ or flhDC operon induction, respectively.

2. Results i. FlgM Produced from $P_{araBAD}$::FlgM is Secreted.

Figure 4:
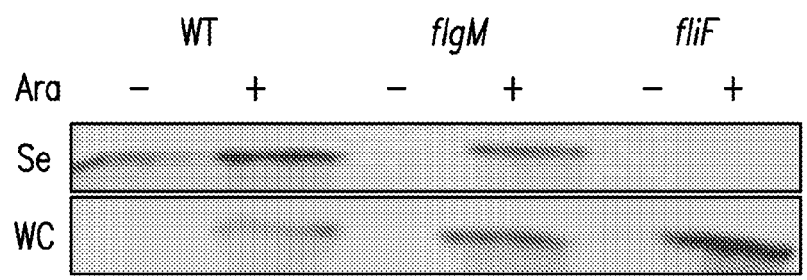

FlgM is secreted through a completed HBB into the external spent growth medium. It has been shown that fusion of foreign proteins to the C-terminus of FlgM can be used for protein purification purposes without the need to lyse cells prior to purification. In order to develop the flagellar T3S system for protein purification using FlgM as a secretion signal, the known aspects of FlgM production and secretion were characterized to maximize protein production using this system. The FlgM gene is transcribed from a class 2 flagellar promoter in the flgAMN operon. This results in FlgM production during initial HBB assembly. Class 2 produced FlgM binds $\sigma^{28}$ protein, the product of the fliA gene, which is also produced via class 2 transcription in one of two fliAZ transcripts. Upon HBB completion a change in the secretion substrate specificity of the flagellar T3 S system results in FlgM secretion and initiation of $\sigma^{28}$-dependent class 3 transcription. FlgM and $\sigma^{28}$ continue to be produced from $\sigma^{28}$-dependent FlgMN and fliAZ transcripts, respectively. About 80% of steady-state FlgM transcription is from its class 3 promoter. Since FlgM is an anti-$\sigma^{28}$ factor, its production via the class 3 promoter is under auto-inhibition. In this example, FlgM gene transcription was removed from FlgM auto-inhibition by using a construct with the FlgM gene transcribed from the arabinose-inducible chromosomal araBAD promoter ($P_{araBAD}$). This was accomplished by a targeted deletion of the chromosomal araBAD operon followed by insertion of the FlgM⁺ gene in its place. This resulted in the arabinose-dependent induction of FlgM production in strains where the arabinose inducer is not degraded due to deletion of the araBAD structural genes. FlgM transcribed from $P_{araBAD}$ was produced in the presence of arabinose and secreted at levels higher than FlgM produced and secreted from its native promoters (FIG. 4). A fliF deletion strain, which does not form flagellar structures, was unable to secrete $P_{araBAD}$-induced FlgM (FIG. 4). These results indicate that FlgM intrinsic-peptide secretion signals are sufficient for high level FlgM secretion and the flagellar-dependent T3 S system can be used for FlgM secretion.

ii. Mutations Affecting FlhD4C2 Activity Also Affect FlgM Secretion.

The flhDC operon is at the top of the flagellar transcriptional hierarchy. The regulation of flhDC is complex and there are six known transcription initiation sites within the flhDC promoter region. Changes in the −10 sequences for the P1 and P4 transcription initiation sites within the flhDC promoter region to the canonical TATAAT sequence (the $P_{flhDC}$7793 allele) resulted in the doubling of the number of HBB structures per cell and increased production and secretion of the flagellar hook protein. Other mutations resulting in increased hook protein secretion and increased HBB structures per cell resulted in reduced expression or removal of known inhibitors of flhDC operon transcriptional or post-transcriptional control. The effects of flhDC regulatory mutations on the secretion of FlgM transcribed from $P_{araBAD}$ were tested. The known transcriptional and post-transcriptional inhibitors of flhDC expression included in this example were EcnR, RscB, LrhA, FliT, DskA and YdiV. EcnR is responsible for FlhDC-mediated auto-repression. The FlhD4C2 complex directs transcription of ecnR, which in turn results in repression of flhDC transcription in concert with the RcsB protein. RcsB, which regulates capsular polysaccharide synthesis and a number of genes in response to membrane and cell wall damage, is a repressor of flhDC transcription. LrhA is also a regulator of flhDC that has been shown to bind within the flhDC promoter region to inhibit flhDC operon transcription. FliT is transcribed from both class 2 and class 3 flagellar promoters. FliT binds to the FlhD4C2 complex and prevents activation of flagellar class 2 transcription. FliT is also the secretion chaperone for the flagellar filament capping protein FliD. Secretion of FliD after HBB completion couples inhibition of further class 2 transcription by FlhD4C2 to HBB completion. The DskA protein acts with ppGpp to inhibit flhDC's transcription. DskA can also stimulate rpoS translation, which can inhibit flhDC transcription through an RpoS-mediated mechanism. YdiV is a post-transcriptional regulator that targets FlhD4C2 to the ClpXP protease for degradation in response to changes in nutrient growth conditions. As a control, CsrA, which is a positive regulator of flhDC mRNA stability, was used. The $P_{flhDC}$8089 allele was constructed by replacing the flhDC promoter control region with a tetR-$P_{tetA}$ cassette from transposon Tn10. This resulted in the placement of the flhDC operon under control of the tetA promoter, which can be induced by the addition of the tetracycline analog anhydro-tetracycline. The flhDC P1 and P4 canonical promoter up changes that increase hook production and secretion (the $P_{flhDC}$7793 allele) were also tested. The effects of the flhDC regulatory mutations on levels of secreted FlgM protein expressed from $P_{araBAD}$ are shown in FIG. 5.

Figure 5A:
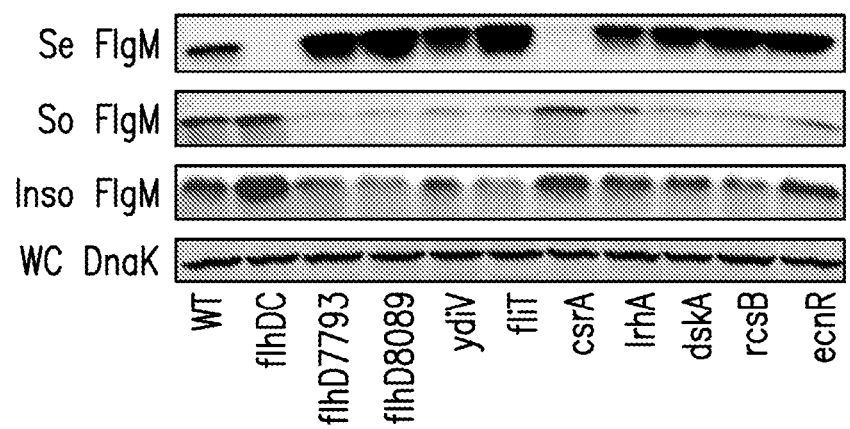
Figure 5B:
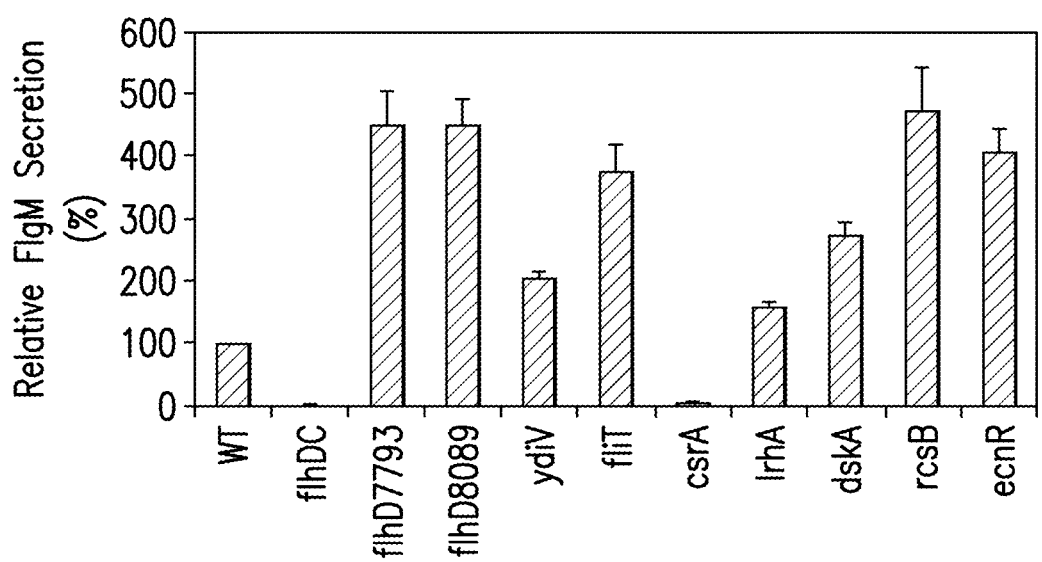
Figure 5C:
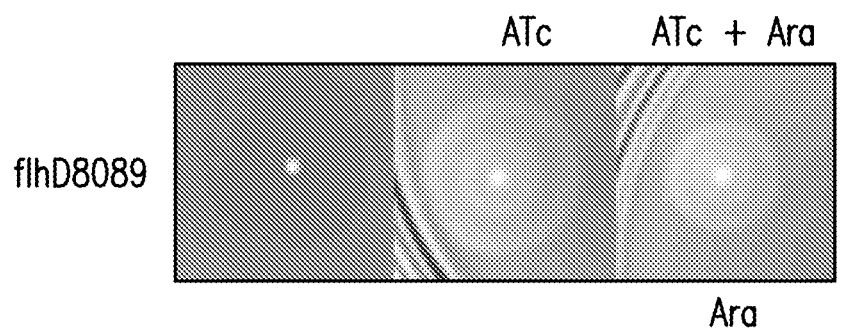

Deletion of the flhDC structural operon or deletion of the csrA gene, which is required for flhDC mRNA stability, had no detectable FlgM in the secreted fraction and FlgM accumulated in the cytoplasm. Mutations defective in known transcriptional and post-transcriptional inhibitors of flhDC expression resulted in increased levels of secreted FlgM as did the presence of $P_{flhDC}$7793 promoter-up allele. Secreted levels of FlgM in $P_{flhDC}$7793, $P_{flhDC}$80899 (tetR-$P_{tetA}$-flhDC), fliT, rcsB and ecnR mutant strains were 4.5-, 4.5-, 3.8-, 4.7- and 4-fold higher than that of wild type, respectively. Secreted levels of FlgM were less in ydiV, lrhA and dskA mutants strains at 2-, 1.5- and 2.7-fold compared to wild type, respectively (FIG. 5B). For each strain tested, the accumulated cellular levels of FlgM were inversely proportional to secreted FlgM levels. Significantly, replacement of the flhDC promoter region with tetA promoter and regulatory region from transposon Tn10 allowed for the production of secreted FlgM at levels meeting or exceeding FlgM secreted levels observed in loss-of-function mutants for the negative regulators of flhDC expression that were tested. Induction of flhDC in the $P_{flhDC}$8089 (tetR-$P_{tetA}$-flhDC) also conferred motility on swim plates (FIG. 5C).

Figure 5D:
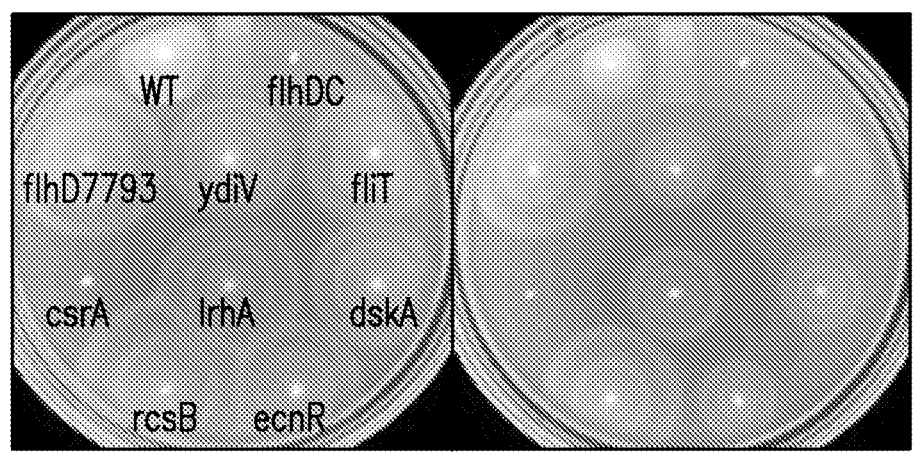

In strains missing negative regulators of flhDC, the swimming phenotypes on soft agar plates indicated increased motility compared to wild type LT2 (FIG. 5D). Substantial levels of motility in the same strains with FlgM overexpressed from $P_{araBAD}$ were noted (FIG. 5D). FlgM inhibits $\sigma^{28}$ at a stoichiometry of 1:1. Induction of FlgM from $P_{araBAD}$ can prevent all $\sigma^{28}$-dependent flagellar class 3 promoter transcription especially in the wild-type LT2 background. This observation led the conclusion that overexpressed cellular FlgM aggregated into an inactive form. Thus, the cellular component of FlgM was analyzed from both soluble and insoluble fractions from the cell pellet in the Western blot analysis of secreted and cellular FlgM levels. Although FlgM is a soluble protein most cellular FlgM produced under overexpression conditions was insoluble (FIG. 5A) indicating that excess cellular FlgM went into inclusion bodies and the observed motility under FlgM inducing conditions indicated that the insoluble form of FlgM was not active.

iii. The Effect of the FlgM T3S-Chaperone, $\alpha^{28}$, on FlgM Secretion.

Completion of the HBB coincides with a flagellar T3S substrate-specificity switch from rod-hook type secretion substrates to late or filament-type secretion substrates. The late secretion substrates include hook-filament junction proteins (FlgK and FlgL), filament cap protein (FliD), the alternately expressed filament proteins (FliC or FljB) and the anti-$\sigma^{28}$ factor FlgM. Efficient secretion of each late secretion substrates requires the aid of a cognate T3S chaperone. These include FlgN (for FlgK and FlgL), FliT (for FliD), FliS (for FliC and FljB) and $\sigma^{28}$ (for FlgM). T3S chaperones fall into three classes: i) those that bind and protect substrates from proteolysis in the system prior to secretion, ii) those that facilitate substrate secretion and iii) those that both stabilize and facilitate secretion. The $\sigma^{28}$ protein falls into the latter category; it protects FlgM from proteolysis in the cytoplasm and facilities the secretion of FlgM presumably by helping to localize FlgM to the base of the flagellum. A mutant of $\sigma^{28}$ with two amino acid substitutions that render it defective in recognition of the −10 and −35 promoter sequences (R91C and L207P) retains its T3S chaperone activity for FlgM secretion. This indicated that the T3S chaperone function of $\sigma^{28}$ was a separate process from its transcription activity.

The $\sigma^{28}$ protein contains 3 of the 4 regions conserved in all $\sigma^{70}$-type housekeeping sigma factors: regions 2, 3 and 4, which are further divided into sub-regions 2.1, 2.2, 2.3, 2.4, 3.1, 3.2, 4.1 and 4.2. Region 2.1, 3.1, 3.2 and 4.1 are involved in binding to the core RNA polymerase while regions 2.4 and 4.2 are required for recognition of the −10 and −35 regions of promoter sequences, respectively. FlgM was shown to interact with all three regions of $\sigma^{28}$ in a FlgM:$\sigma^{28}$ co-crystal structure. In addition, single amino acid substitution mutations that were defective in FlgM inhibition of $\sigma^{28}$-dependent flagellar transcription were located in regions 2.1, 3.1, 4.1 and 4.2. These were designated FlgM-bypass mutants because in strains defective for HBB formation they resulted in class 3 flagellar promoter transcription, which is normally inhibited by FlgM in the fliA⁺ background. The $\sigma^{28}$ FlgM bypass mutants were of two classes. The majority was defective in binding to FlgM, but two alleles, H14D and H14N each resulted in a $\sigma^{28}$ protein with increased stability, which was enough to overcome FlgM inhibition.

Figure 6A:
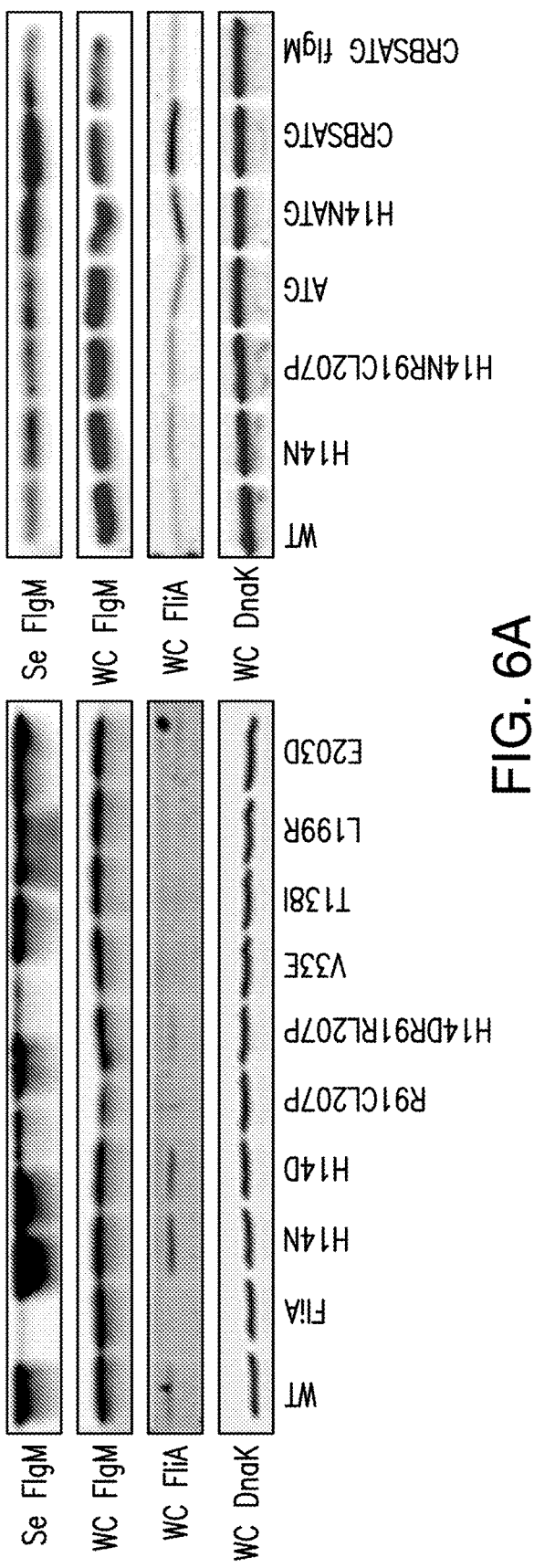
Figure 6B:
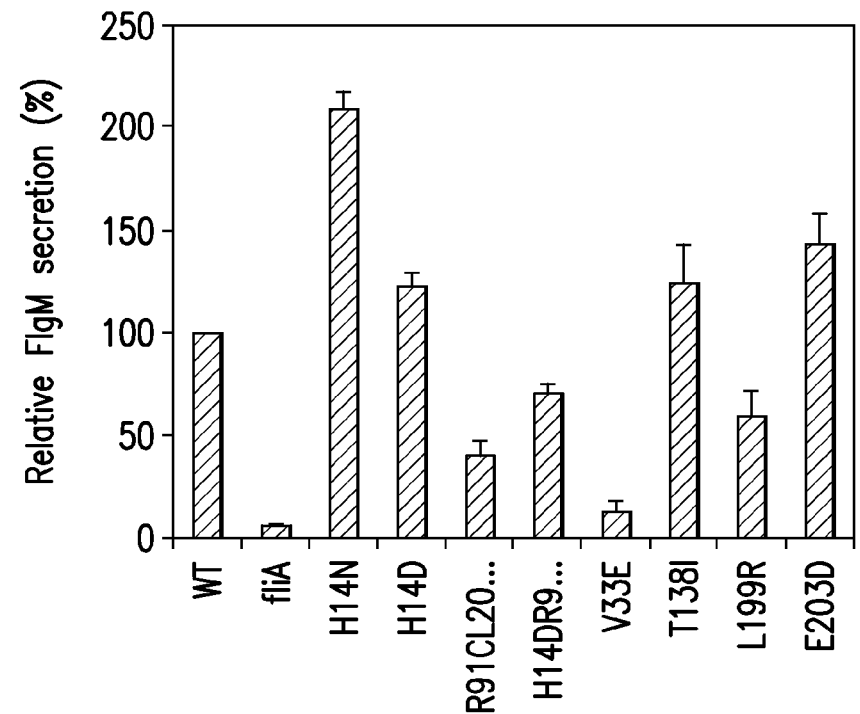
Figure 6B:
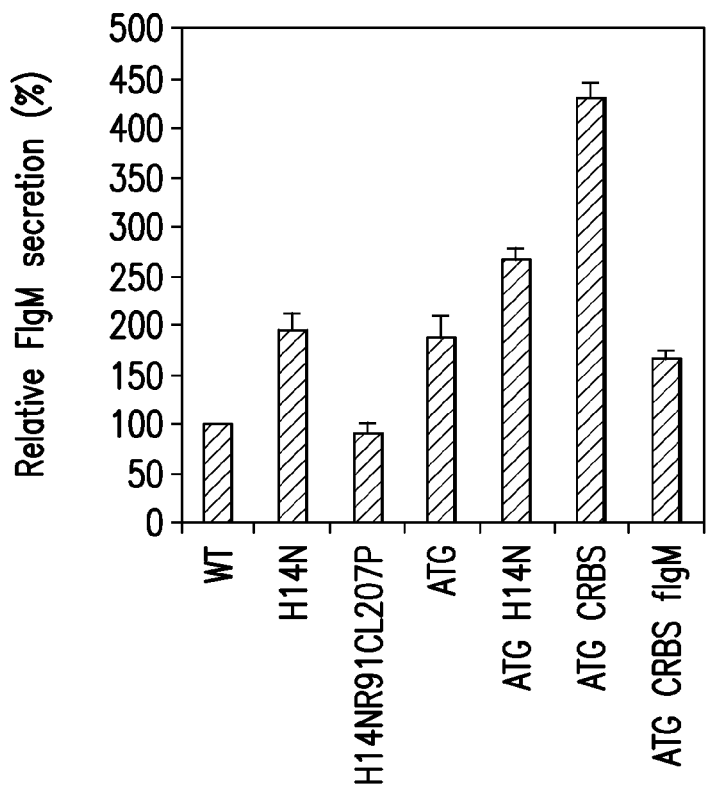

The effects of FlgM bypass mutants in $\sigma^{28}$ regions 2, 3 and 4 on secretion of FlgM expressed from $P_{araBAD}$ were tested (FIGS. 6A and 6B). The region 2.1 mutants included the H14D and H14N, which result in increased protein stability and the V33E allele, which is defective in binding FlgM. The other FlgM-bypass mutants tested included the T138I allele from region 3.1 and L199R from region 4.1 and E203D at the initiation point of region 4.2.

The fliA null allele showed a strong reduction in FlgM secretion to a level that was 5% of the fliA⁺ strain. The V33E and L199R allele resulted in FlgM secretion level that was 12% and 59% of wild type, respectively. The H14D and H14N alleles exhibited secreted FlgM levels that were 2.1 and 1.5-fold of that seen for wild type. The T138I and E203D alleles, that are defective in binding FlgM, resulted in increased secreted FlgM levels 1.2 and 1.4-fold of wild type, respectively. The promoter binding-defective double mutant of fliA (R91C L207P) was also tested and compared to wild-type showed a 39% level of secreted FlgM. The promoter binding-defective R91C L207P substitutions were also combined with the H14D increased stability substitution and observed secreted FlgM levels in between those observed with the either just the R91C L207P double-mutant or the H14D single mutant.

For wild type FliA, H14N, H14D, R91C L207P, and H14D R91C L207P, the FliA level in the cell was consistent with the FlgM secreted level (FIG. 6A). The FlgM secreted level was related to FliA concentration within the cell. Therefore, other mutants were introduced, which would potentially increase the intracellular FliA concentration, to see whether they could affect FlgM secretion. These mutants included a fliA start codon change from GTG to ATG that was combined with either H14N stabilization substitution or with a change of the fliA ribosome binding sequence (RBS) to a canonical sequence (CRBS). All of these changes resulted in increased FliA intracellular levels and secreted FlgM levels from 2- to 4-fold that of wild type (FIGS. 6A and 6B). Deletion of the chromosomal FlgM gene in the fliA CRBS ATG double mutant, background resulted in a reduction of both of intracellular FliA and secreted FlgM. Thus, the excess $\sigma^{28}$ produced in the fliA CRBS ATG double mutant background can involve chromosomal FlgM expression in addition to $P_{araBAD}$-expressed FlgM to contribute to $\sigma^{28}$ stability, which improves FlgM secretion. This is consistent with the results showing that FlgM not only acts as an anti-sigma factor but also protects FliA from being degraded.

Figure 6C:
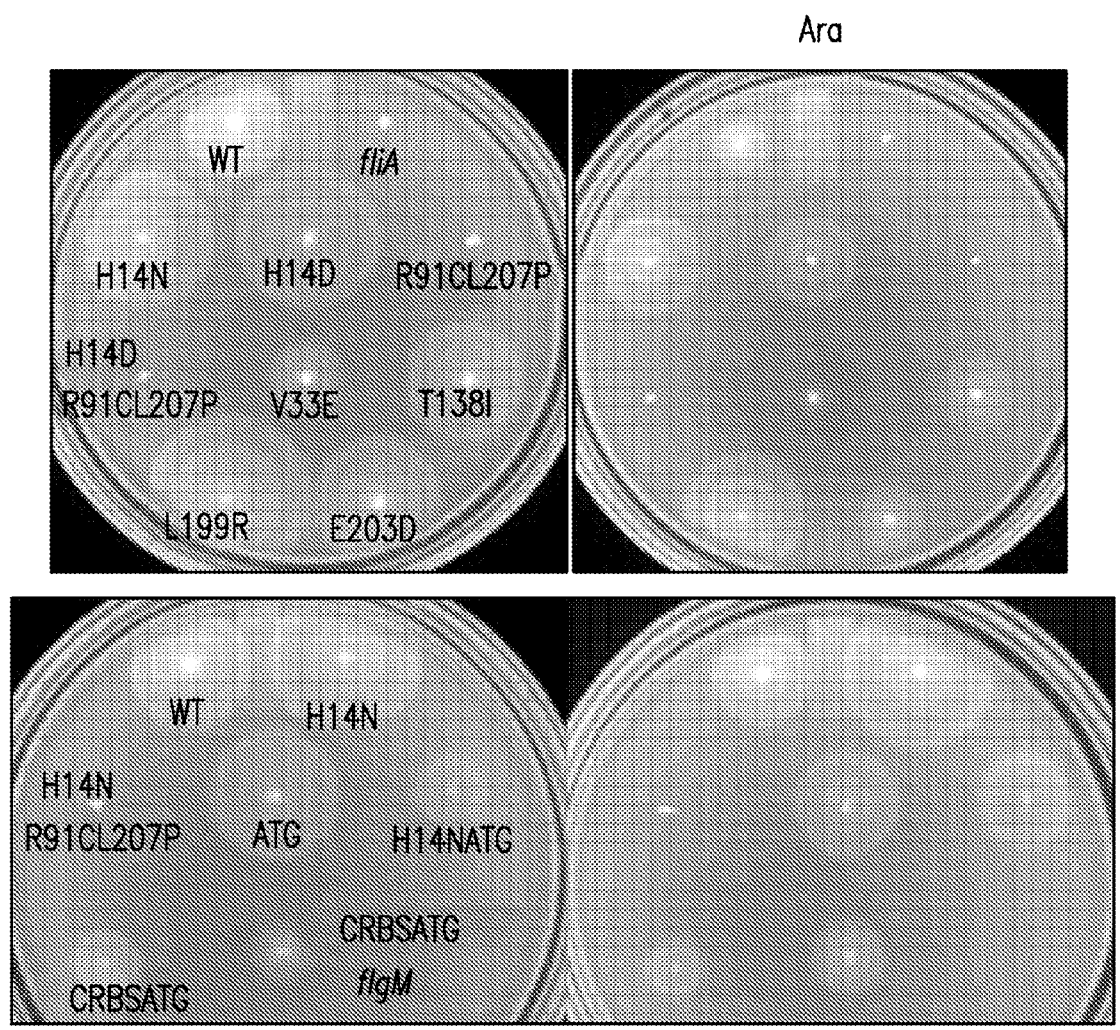

Motility assays of the fliA mutants under FlgM induced conditions are showed in FIG. 6C. The fliA null allele and mutants containing the R91C L207P alleles, which are unable to transcribe flagellar class 3 promoters and therefore unable to produce flagellin, are non-motile under any condition. The H14N, H14D, ATG substitution mutants showed increased swarm sizes on motility plates compared to wild type. V33E, T138I, L199R and E203D are reported to have flagellar transcriptional activities in the presence of FlgM that are 8.0, 31, 45 and 7-fold higher than wild-type, respectively and their motility phenotypes on swim plates under FlgM inducing conditions correlate with these levels. The H14N ATG and CRBS ATG double mutants showed decreased motility on swim plates, although they have higher cellular levels of $\sigma^{28}$ than the wild type strain.

iv. The Effect of the Flagellar Late T3S Secretion-Substrate Competitors on FlgM Secretion.

Figure 7A:
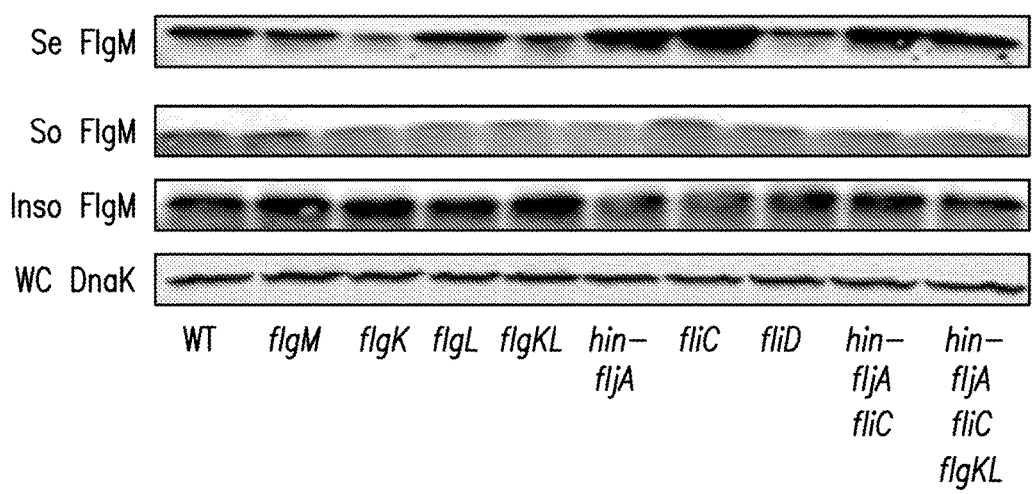
Figure 7A:
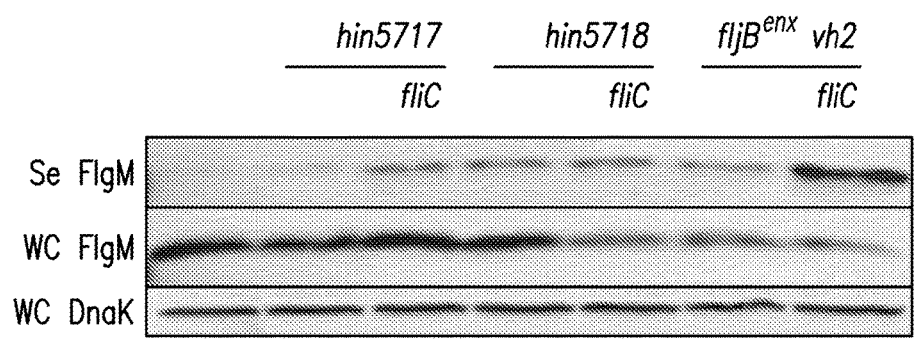
Figure 7B:
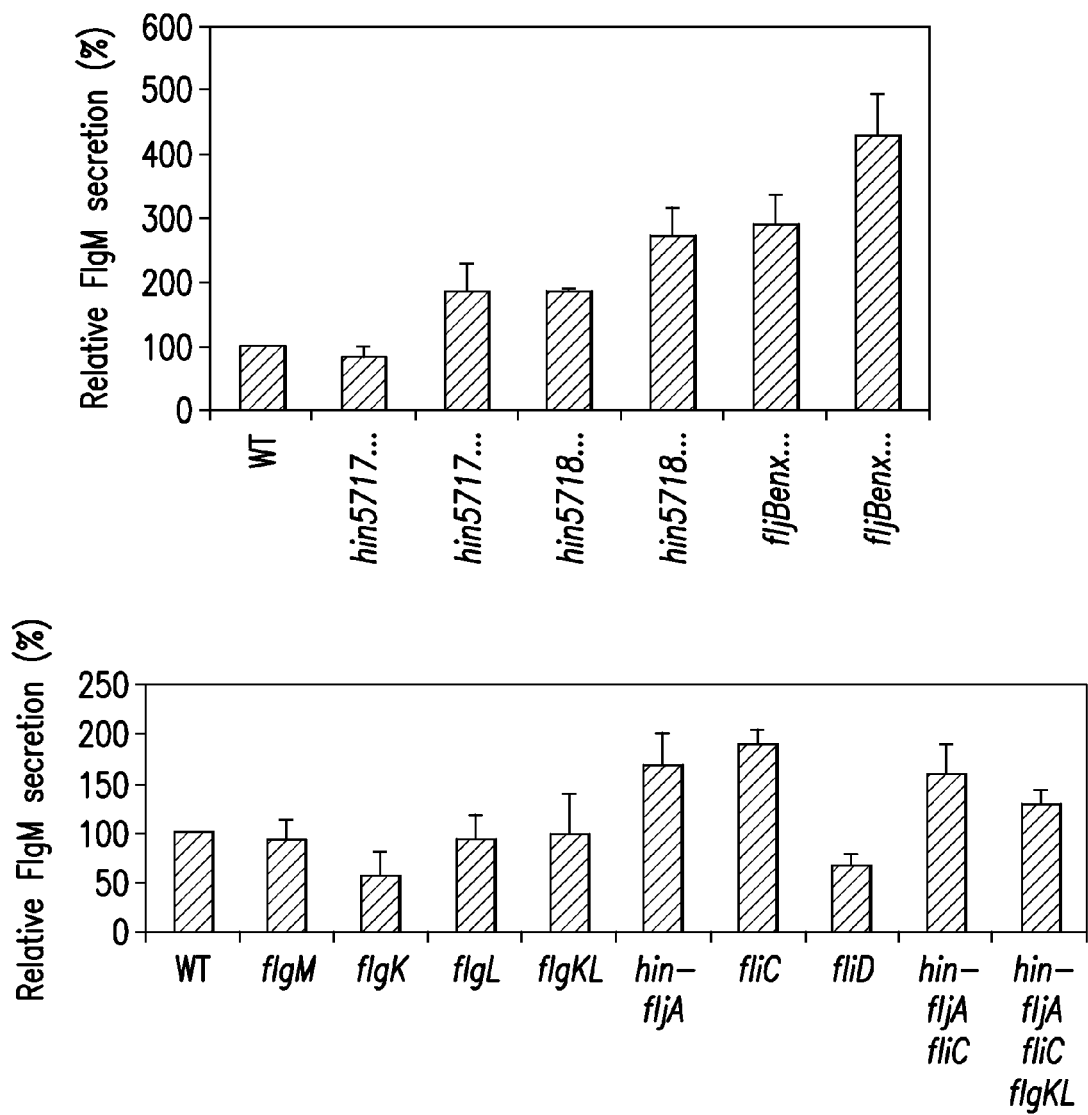

The initial report of FlgM secretion upon HBB completion presented qualitative data showing that secreted FlgM levels were higher in strains missing filament protein, a potential secretion competitor for FlgM. The effects of removing potential late secretion-substrate competitors on secreted FlgM levels were tested, to determine if their removal would improve the yield of secreted FlgM. The number of late substrate subunits in the assembled flagellum are about 11 each for hook-filament junction proteins FlgK and FlgL, 5 for the filament capping protein FliD, and, depending on filament length, up to 20,000 for FliC or FljB. The results presented in FIGS. 7A and 7B show that removal of FlgK, FlgL or FliD had little or no effect on secreted FlgM levels, while removal of the filament substrates resulted in increased levels of secreted FlgM up to 1.9-fold higher than wild-type. This result shows that late T3S substrate levels are not a significant limiting factor in the secretion of FlgM through the flagella.

The effects of flagellar phase variation on FlgM secretion was also tested (FIGS. 7A and 7B). *Salmonella enterica* alternately expresses one of two flagellin subunit genes, fliC or fljB. Strains carrying the hin-5717 allele are locked in the $FliC^{ON}$ $FljB^{OFF}$ flagellin expression mode while strains carrying the hin-5718 allele are $FliC^{OFF}$ $FljB^{ON}$. The $fljB^{enx}$ vh2 is a historical relic that is also $FliC^{ON}$ $FljB^{OFF}$, and resulted from replacement the hin-fljBA region from *S. enterica* strain LT2 with the same region from *Salmonella abortus*-equi locked in the $FliC^{ON}$ $FljB^{OFF}$ mode. The FlgM secretion level in a strain carrying the hin-5717 allele was similar to that of wild type strain. Deletion of the fliC gene in the hin-5717 background resulted in a 1.9-fold increase in secreted FlgM compared to wild type. The presence of the hin-5718 allele alone increased secreted FlgM levels by 1.9-fold and the additional removal of the fliC gene in this background further increased the secreted FlgM level 2.7-fold that of wild type even though FliC flagellin is not produced in the hin-5718 background. However, fliC mRNA is produced, but not translated, in the hin-5718 background, showing that fliC mRNA has a negative effect on FlgM protein secretion. Secreted levels of FlgM in the $fljB^{enx}$ vh2 background were 2.9-fold higher than in the wild type strain and further removal of the fliC gene in this background increased secreted FlgM levels to 4.3-fold of wild type.

v. The Effect of the Flagellar Late T3S Chaperones on FlgM Secretion.

The effects of removing the late secretion chaperones FlgN, FliS and FliT on secreted levels of FlgM expressed from $P_{araBAD}$ was also tested to determine if they compete with $\sigma^{28}$ for delivery of FlgM to the flagellar secretion system for export. Also, T3S chaperones are associated with regulatory functions in the absence of their cognate secretion substrates. FlgN, the T3 S chaperone for FlgK and FlgL, inhibits FlgM mRNA translation. $\sigma^{28}$ is a transcription factor for flagellar class 3 promoters, and FliT acts as an anti-FlhD4C2 factor. Only FliS is not reported to have a regulatory function in the absence of its cognate secretion substrates FliC and FljB.

Figure 8A:
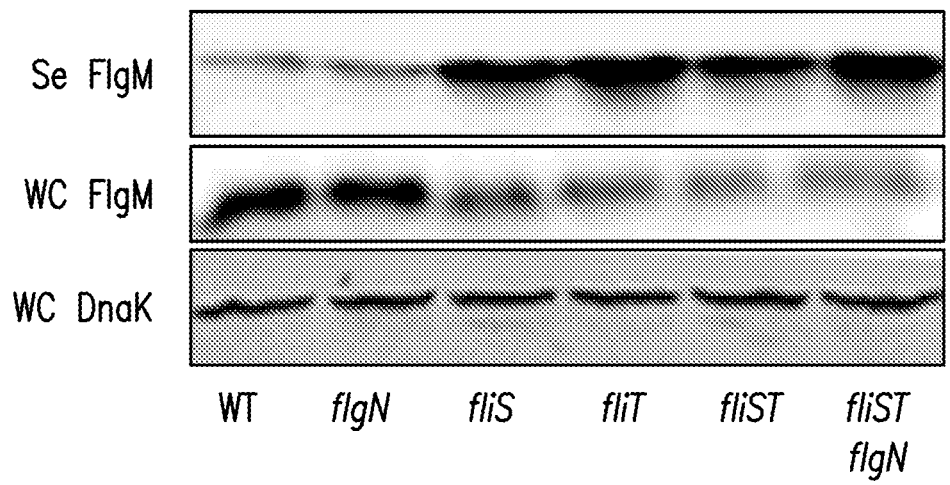
Figure 8B:
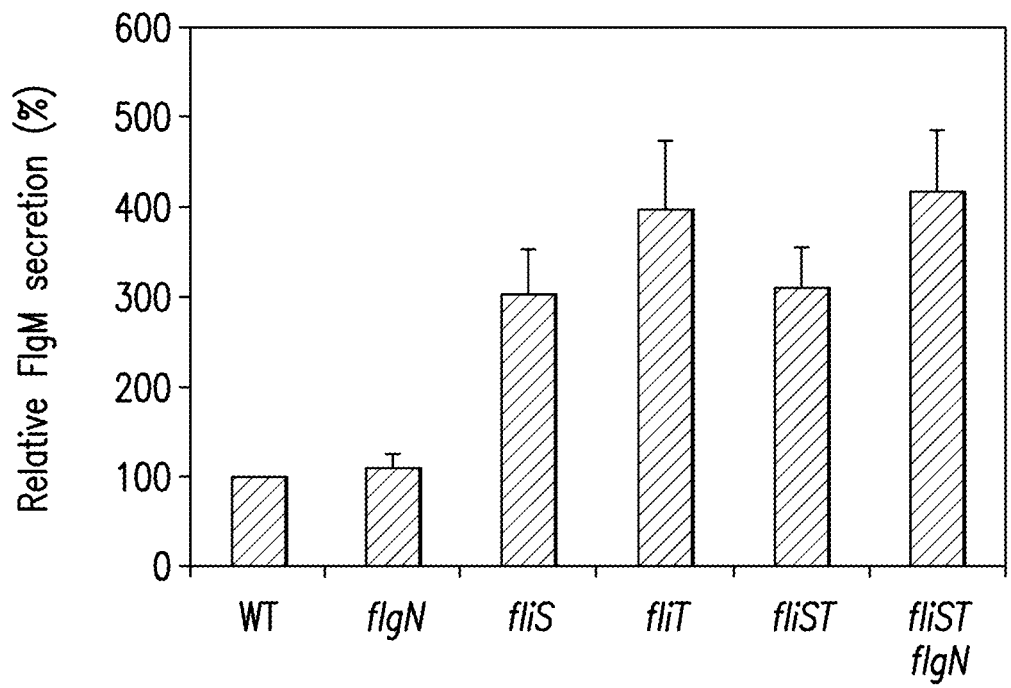

Removal of FlgN had little effect on FlgM secretion (FIGS. 8A and 8B). FlgK and FlgL did not have a significant effect on secreted FlgM levels either (see FIGS. 7A and 7B). Removal of FliT, which is also reported in FIG. 4, resulted in a 4-fold increase in secreted FlgM levels. Alleles of fliT that separate its anti-FlhD4C2 activity from its chaperone activity were not used. Thus, the increase in secreted FlgM levels is due to enhanced FlhD4C2 activity in the absence of FliT. A 3-fold increase in secreted FlgM levels in the absence of FliS was observed. However, fliS is transcribed in an operon upstream of the fliT gene. Thus, any polar effect of the fliS alleles on fliT results in increased FlgM secreted levels due to deceased fliT gene expression.

vi. Deletion of *Salmonella* Pathogenicity Island 1 (Spi1) Results in Increased Levels of Secreted FlgM.

Figure 9A:
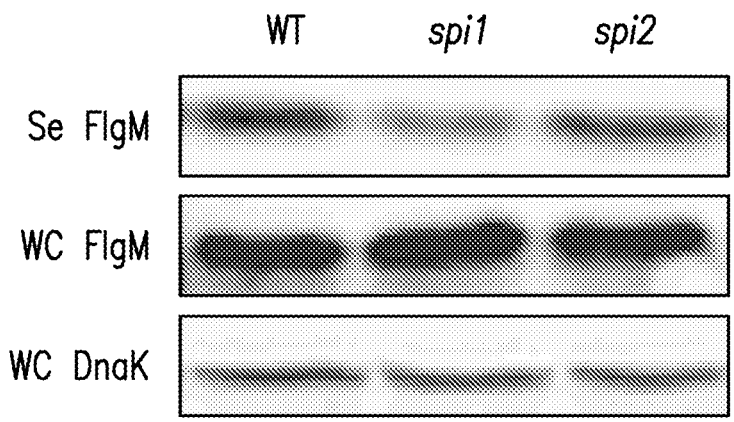
Figure 9B:
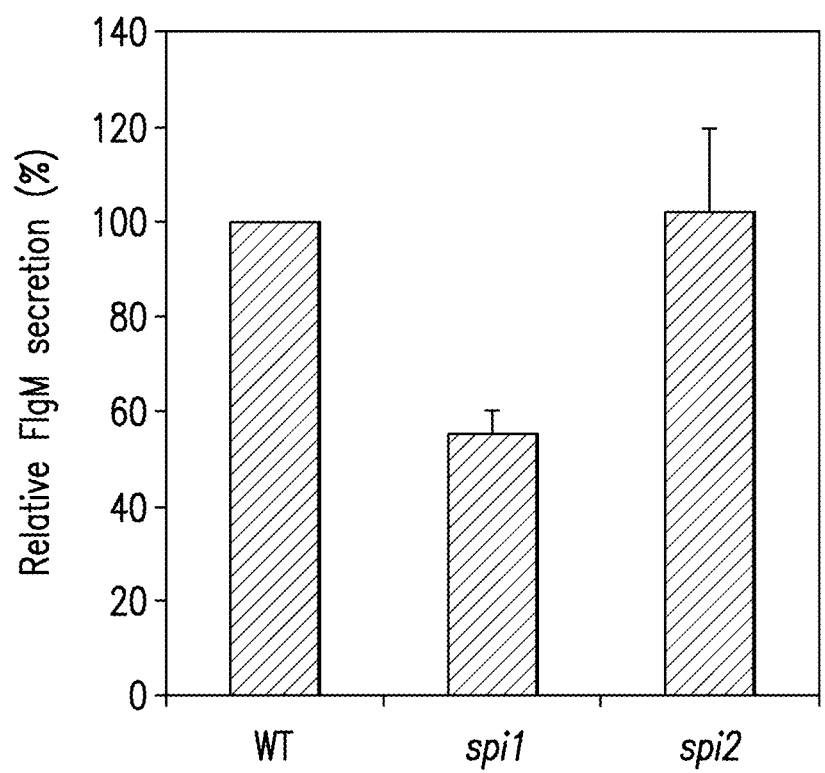

The flhDC operon is the master operon of both the flagellar regulon and the genes of Spi1. The Spi1 regulon encodes genes needed for the structure and assembly of the Spi1 injectisome T3 S system. The fliZ gene is transcribed in the fliAZ operon and FliZ activates transcription of hilD, whose product in turn activates Spi1 transcription. One HilD activated gene product, RtsB, acts to repress flhDC transcription providing a feedback loop for the entire flagellar-Spi1 regulon. The effects of deletions of both the Spi1 and Spi2 *Salmonella* virulence systems on the secreted levels of overexpressed FlgM (from $P_{araBAD}$) were tested. Loss of Spi1 resulted in decreased FlgM secreted levels to 55% that of wild type even though the cells were not grown under Spi1 inducing conditions, whereas loss of Spi2 had no significant effect on secreted levels of FlgM (FIGS. 9A and 9B).

vii. Effect of Protease Removal on FlgM Secreted Levels.

A common technique used to improve protein yield from the cytoplasm is by removing cellular proteases. In addition, proteases present in the outer membrane, such as OmpT can decrease protein yield by degradation after cell lysis. The ClpA and ClpX proteins interact with different substrates for delivery to the ClpP serine protease for degradation. DegP is a periplasmic protease that exhibits broad substrate specificity. DegP is exclusively directed against unfolded, mislocalized, hybrid and recombinant proteins that are improperly folded from over-expression in the periplasm.

The results of protease removal on FlgM secreted levels are shown in FIG. 10. Removal of OmpT resulted in a slight increase the yield of secreted FlgM while loss of DegP had little effect. Removal of ClpA, ClpX and ClpP increased the FlgM secretion yield by 1.7-, 5.4- and 6.1-fold compared to wild type, respectively (FIGS. 10A and 10B). This is consistent with the observations that FlhD4C2 is a substrate for YdiV-directed degradation by the ClpXP protease system. As a control for cell lysis, deletion of flhDC in the protease mutant backgrounds showed no detectable FlgM in the secreted fraction. In this background, the cellular level of FlgM remained unaffected by loss of DegP mutation, while null alleles of clpA, clpX and clpP mutation on the flhDC background increased intracellular FlgM accumulation by 1.3-, 1.5- and 2.1-fold, respectively (FIG. 10B). The results indicate that ClpA, ClpX and ClpP are involved in FlgM degradation independent of FlhDC; the increased FlgM secretion in the clpA null strain was due to increased cellular level FlgM alone. The effects of the ClpXP protease in the presence of flhD⁺flhC⁺ were due to both FlgM stability and FlhD4C2 stability. This is consistent with increased motility observed in the clpP and clpX mutant strains (FIG. 10C).

viii. Effect of Ionic Strength on Secreted FlgM Levels.

Figure 11A:
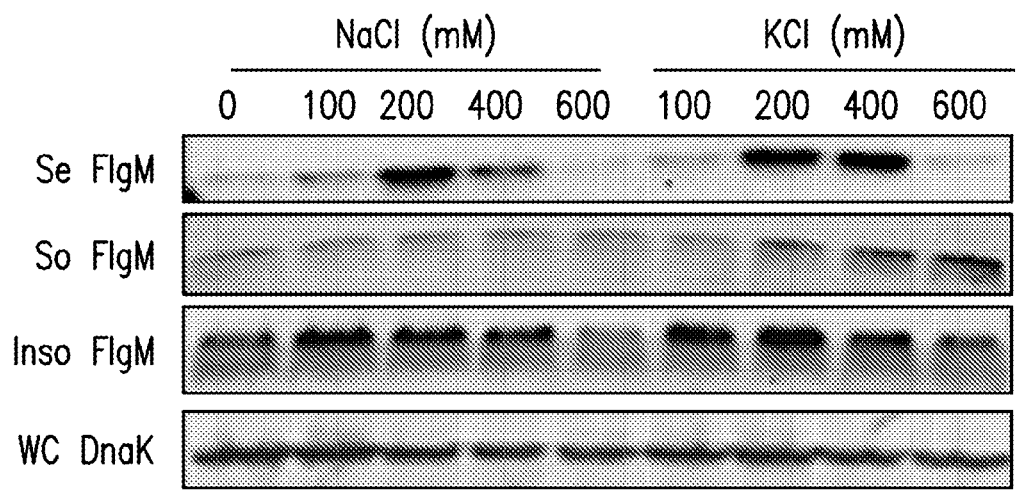
Figure 11B:
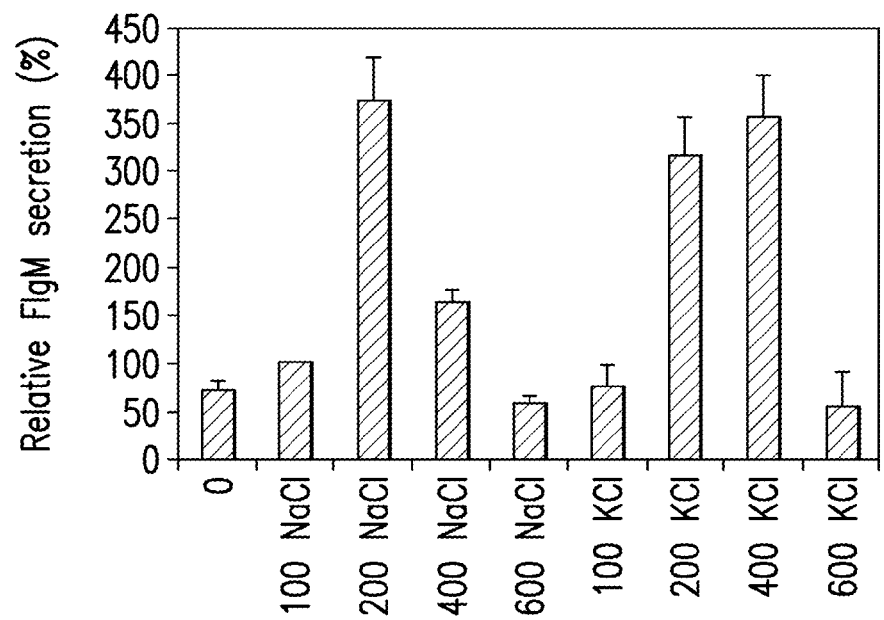
Figure 11C:
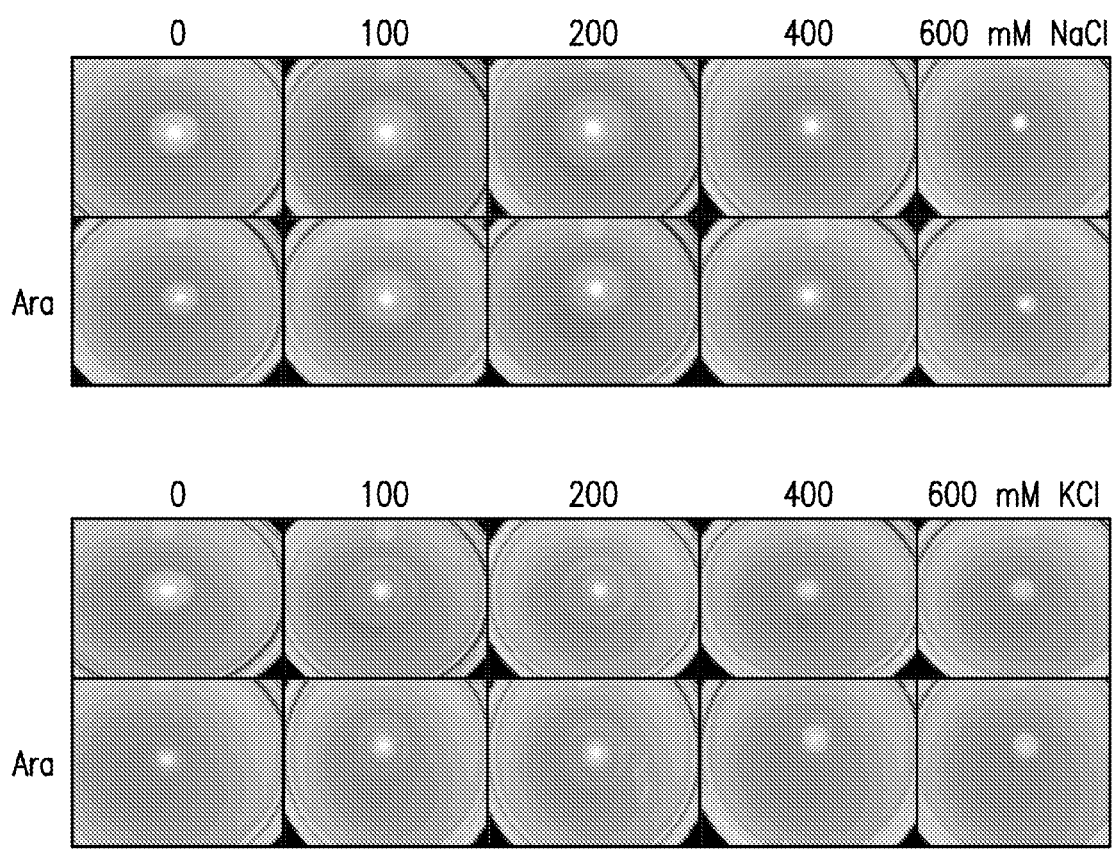

High osmolarity increased Spi1 invA gene transcription in *S. enterica*, and Spi1-dependent type III secretion occurred only in bacteria grown under high salt conditions. The effects of either increased NaCl or KCl on secreted levels of FlgM produced by $P_{araBAD}$-FlgM⁺ were tested. FlgM secreted levels increased when NaCl concentration was raised to 200 mM and then dropped at concentrations of 400 and 600 mM. At 200 mM NaCl, the FlgM secreted level was 3.7-fold higher than the level at 100 mM NaCl (FIGS. 11A and 11B), which is close to the NaCl concentration in a standard LB medium (86 mM). Thus, the NaCl concentration in LB medium is not optimal for FlgM secretion. KCl had a similar effect on secreted FlgM levels, 200 and 400 mM KCl produced the highest levels of secreted FlgM at 3.2- and 3.6-fold compared to the secreted FlgM level at 100 mM NaCl. This is due to effects on the solubility of FlgM in the cytoplasm. Increased ionic strength also had a positive effect on motility in soft agar although this was suppressed under FlgM induction conditions due to inhibition of $\sigma^{28}$-dependent flagellar class 3 transcription (FIG. 11C).

ix. Effect of Multiple Conditions on FlgM Secretion.

Figure 12A:
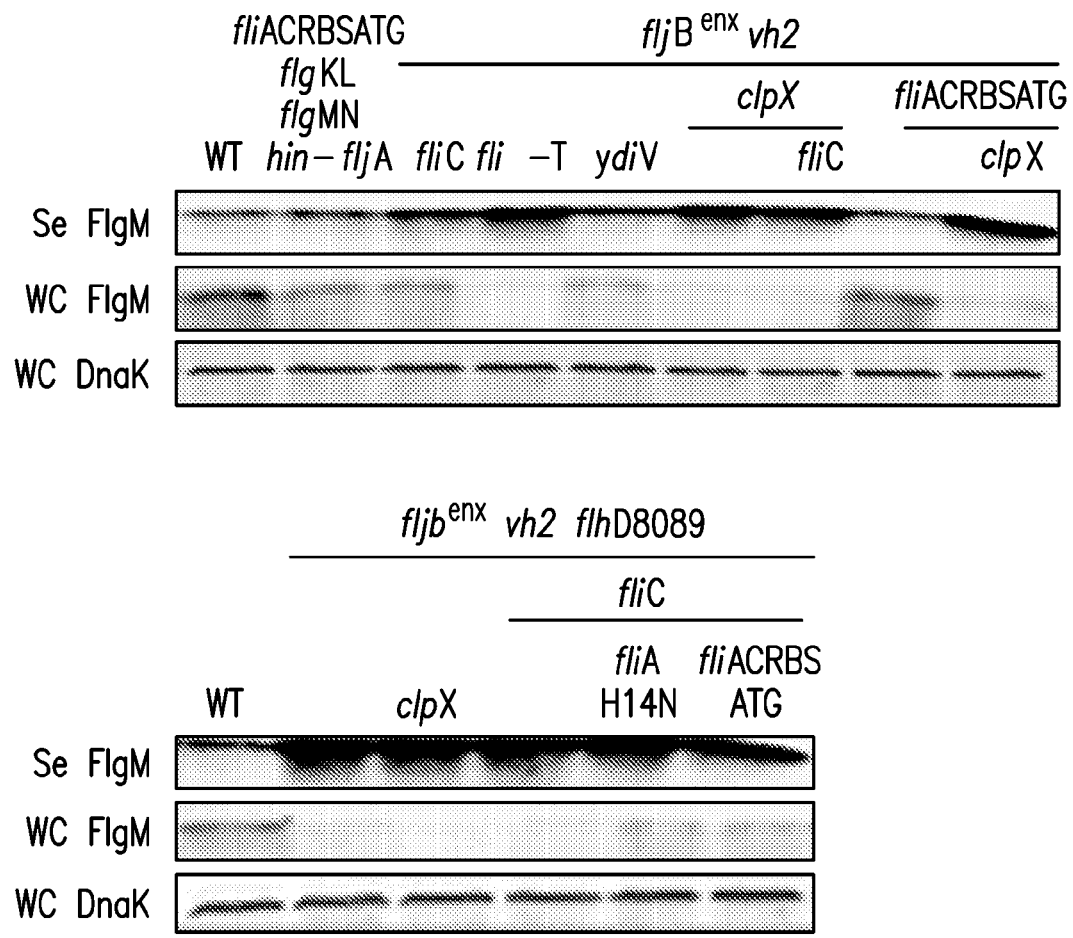
Figure 12B:
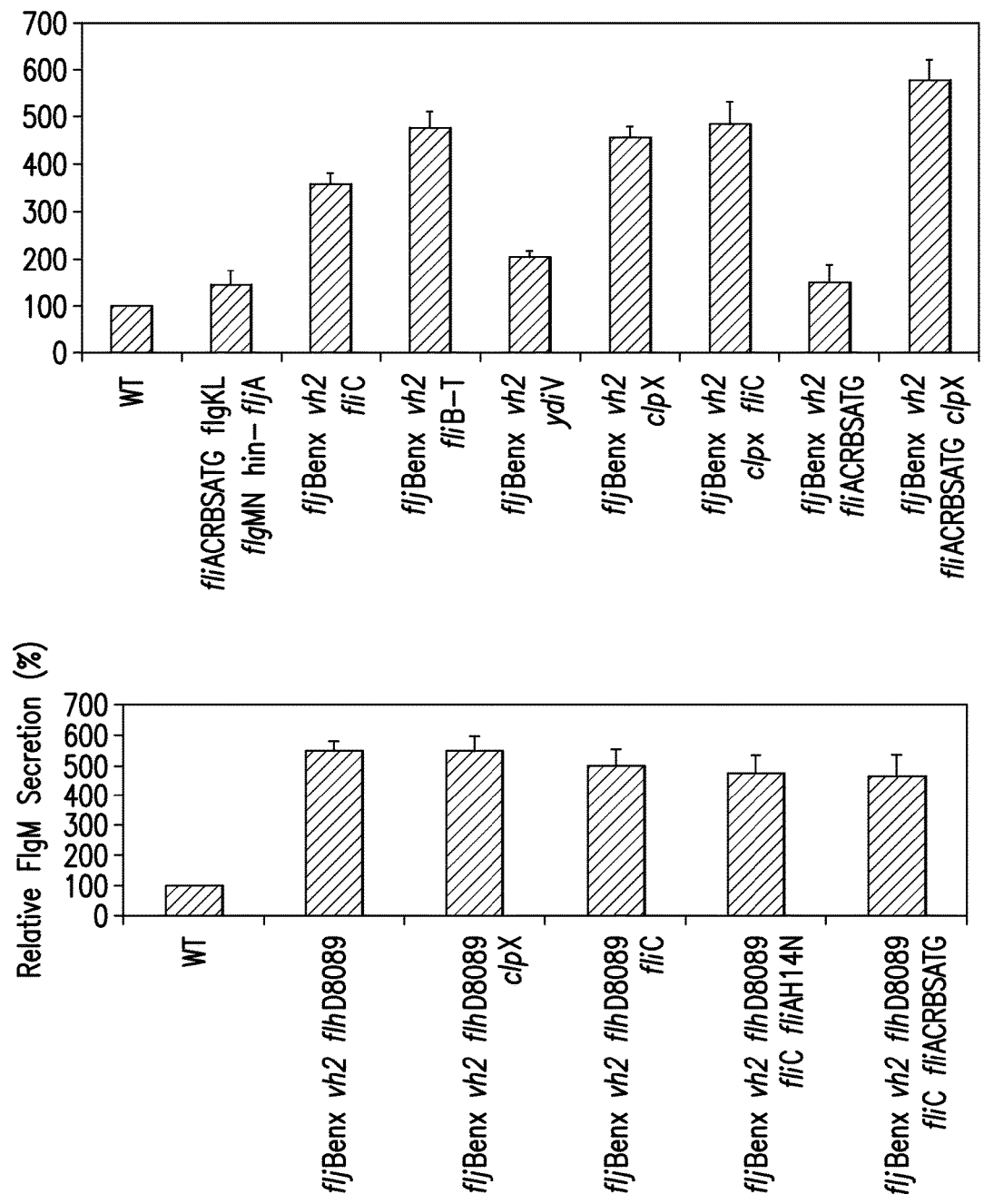
Figure 13A:
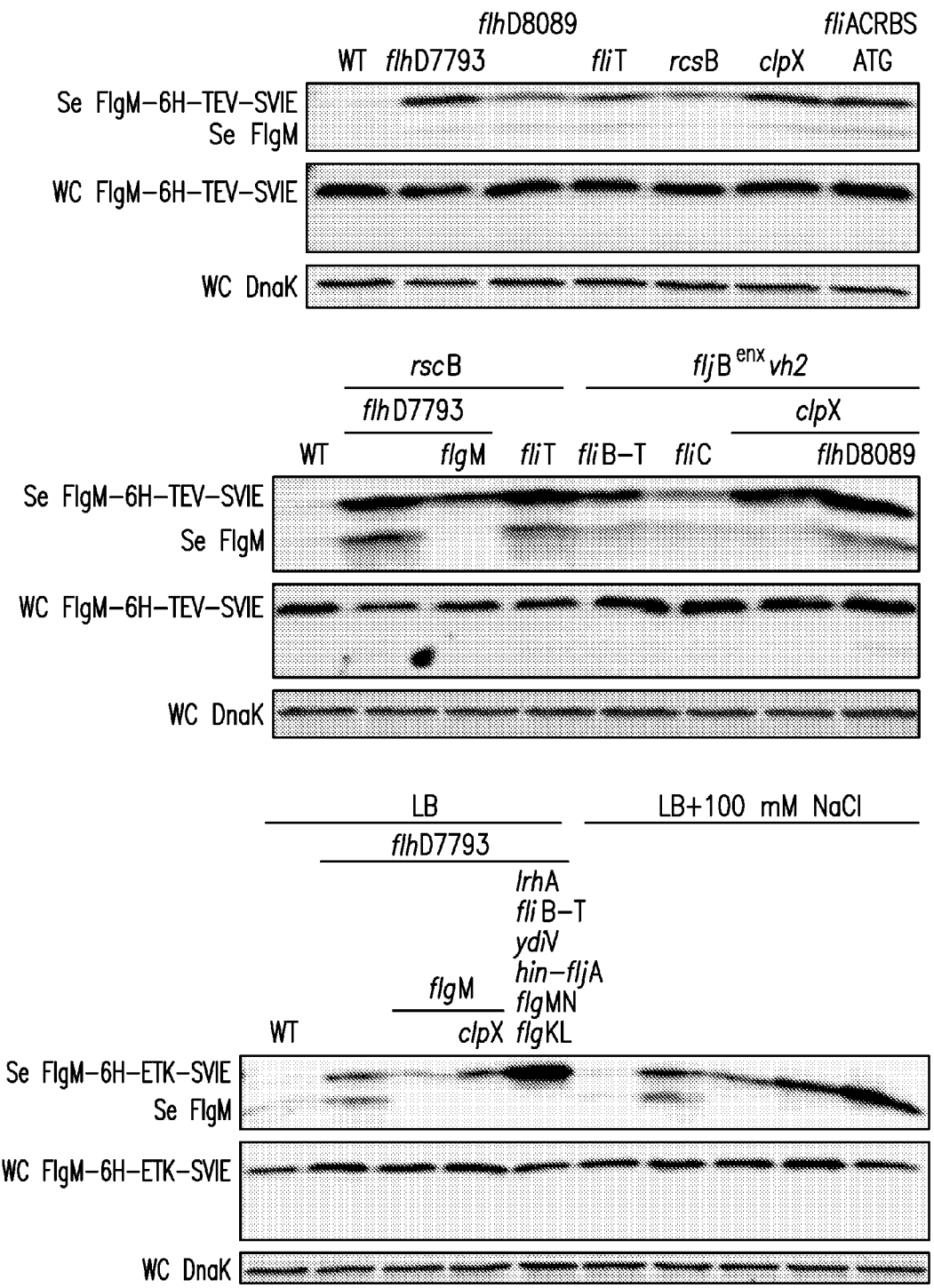
Figure 13B:
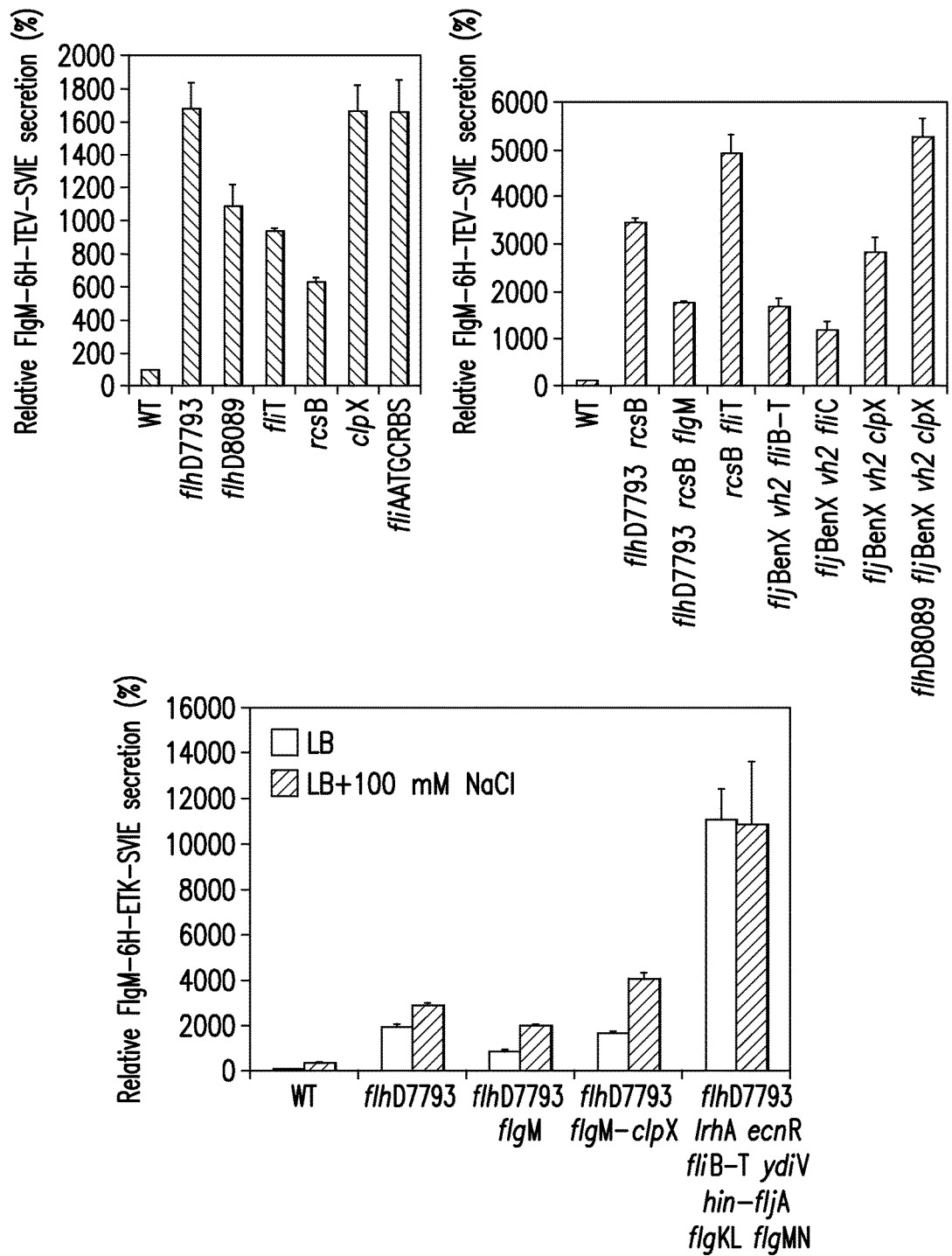

Individual results described above that improved the yield of secreted FlgM were combined in order to obtain a strain and conditions that maximized this yield under FlgM overexpression condition by $P_{araBAD}$::FlgM$^+$ (FIGS. 12A and 12B). Some of these strains, such as fljB$^{enx}$ vh2 and strains containing clpX, strains containing flhD8089, provide the highest FlgM secretion levels. All of them produce secreted FlgM levels about 5-fold that of wild type. In these strains only a trace amount of FlgM accumulated within the cell, showing that expression and stability of cellular FlgM was limiting.

x. Use FlgM as a TTS Signal to Secret δ-SVIE.

The δ-SVIE protein is a small peptide produced by a venomous marine cone snail and inhibits sodium channels in vertebrate neuromuscular systems. This 31 amino acid peptide (DGCSSGGTFCGIHPGLCCSEFCFLWCITFID; SEQ ID NO:74) is hydrophobic and contains 6 cysteine residues that form 3 pairs of intramolecular disulfide bonds. The hydrophobic nature of the peptide and requirement for multiple disulfide bond formation to produce an active conformation of δ-SVIE are an impediment to proper folding when this peptide is overexpressed in *E. coli*. Thus, production of δ-SVIE in an active form via FlgM-mediated secretion was tested. Because secretion from the cell initiates with the N-terminus of FlgM, the δ-SVIE sequence of the FlgM-b-SVIE fusion would exit the cell as it exits the ribosome: from N-terminus to C-terminus This can facilitate proper folding and disulfide formation of δ-SVIE into an active conformation. C-terminal fusions of δ-SVIE to hexa-His-tagged (6His) FlgM with either TEV or ETK protease cleavage sites engineered between the two proteins were expressed from the chromosomal $P_{araBAD}$ expression locus. The 6His facilitates purification using a Ni-agarose affinity column and the TEV and ETK cleavage sites are recognized by TEV protease and enterokinase, respectively, allowing the secreted δ-SVIE to be separated from its FlgM secretion signal.

All of the selected single mutants increased FlgM-6H-TEV-δ-SVIE secretion (see FIGS. 13A and 13B). The secreted levels of $P_{araBAD}$-expressed fusion protein levels were enhanced in mutant backgrounds that produced enhanced secreted FlgM levels. Secreted levels of FlgM-6H-TEV-δ-SVIE in the flhD7793 (TH18880), flhD8089 (TH18647), fliT (TH18769), rcsB (TH18830), clpX (TH18353) and fliA (CRBS ATG) (TH20056) strains were 16.8-, 10.9-, 9.4-, 6.3-, 16.7-, and 16.6-fold compared to wild type (TH17831). Different mutations were combined together, to test FlgM-6H-TEV-δ-SVIE secretion levels. In the multiple mutant background strains flhD7793 rcsB (TH19675), flhD7793 rcsB FlgM (TH20044), rcsB FliT (TH19673), fljB$^{enx}$ vh2 fliB-T (TH20075), fljB$^{enx}$ vh2 fliC (TH20050), fljB$^{enx}$ vh2 clpX (TH20077) and flhD8089 fljB$^{enx}$ vh2 clpX (TH20044) were 34-, 17-, 49-, 16.7-, 11.7-, 28.2-, and 52.7-fold of that of wild type. When 6His-ETK was inserted between FlgM and SVIE, the flhD7793 (TH19118), flhD7793 FlgM (TH19122), flhD7793 FlgM clpX (TH19145), and flhD7793 lrhA fliB-T ydiV hin-fljA FlgMN flgKL (TH19120) strains increased FlgM-6H-ETK-δ-SVIE secretion levels up to 19-, 8.5-, 17-, and 110-fold of that of wild type. Except for the flhD7793 lrhA fliB-T ydiV hin-fljA FlgMN flgKL strain (TH19120), addition of 100 mM NaCl resulted in increased secretion levels of the fusion protein with strains TH19118 (flhD7793), TH19122 (flhD7793 FlgM), and TH19145 (flhD7793 FlgM clpX) were 3.3-, 1.5-, 2.2- and 2.4-fold of wild type.

3. Discussion

The type III secretion (T3S) systems of the flagellum and injectisome provide a conduit for the production and purification of recombinant proteins that are fused to T3S signal. There can be a N-terminal disordered peptide signal and a coupling to the proton motive force as the secretion fuel. Many, but not all T3S substrates can utilize cognate T3S chaperones for their stability in the cytoplasm and/or as secretion pilots for targeting the T3S substrate to the secretion apparatus in the cytoplasmic membrane. Another feature of T3S systems is the ability to undergo a secretion-specificity switch from early to late secretion substrate specificity. In the flagellar system this occurs upon completion of extracellular hook growth that is more than 40 nm in length resulting in the transition to filament-type substrate secretion and assembly. The FlgM protein is an integral part of the transition from hook completion to filament assembly. FlgM is a late, filament-type flagellar secretion substrate and an anti-$\sigma^{28}$ factor. FlgM is a small, 97 amino acid protein. The N-terminal half of FlgM includes the T3S signal while the C-terminal half includes the anti-$\sigma^{28}$ interaction domain. It has been shown that fusion of recombinant proteins to the C-terminus of FlgM would allow for their secretion and purification without a requirement to lyse cells prior to purification. Conditions that facilitate FlgM production and secretion were examined. These conditions were then applied to produce the recombination proteins FlgM-6His-TEV-δ-SVIE and FlgM-6His-ETK-δ-SVIE to produce and purify these proteins without cell lysis using FlgM as a vector to direct the secretion of the –δ-SVIE proteins from the cell via the flagellar T3S system.

FlgM and FlgM-δ-SVIE fusion constructs were over-expressed from the chromosomal $P_{araBAD}$ promoter by replacing the araBAD coding region with the FlgM or FlgM-δ-SVIE fusion coding regions. By removing araBAD it was ensured that arabinose inducer would not be consumed as a carbon source. This inducing system proved sufficient to produce FlgM in quantities in excess of what the cell could secrete (FIG. 5). The cells were then manipulated by introducing mutations that increase FlgM stability and secretion in order to increase production of secreted FlgM.

The effect of mutations that increase the number of flagellar T3 S systems per cell on secreted FlgM levels were examined. These included null mutations in negative regulators of flhDC transcription (ecnR, rcsB, lrhA, dskA) and flhDC promoter-up alleles $P_{flhDC}$7793 and $P_{flhDC}$8089. Null alleles of fliT and ydiV that inhibit FlhD4C2 function at a post-transcriptional level were also tested. Such mutations had been previously shown to increase the production and secretion of the flagellar hook protein into the periplasm. All mutant backgrounds tested resulted in increased levels of secreted FlgM. The $P_{flhDC}$8089 allele is a replacement of the flhDC promoter region with an inducible tetA promoter region, which removes the site of action of all known negative regulators of flhDC transcription. The $P_{flhDC}$8089 allele also places flhDC transcription under induction by tetracycline and its analogs. Without the inducer, the cells were not motile on swimming plate, indicating that flhDC was not transcribed. FlgM was not secreted in the csrA null mutant strain, as CsrA can stabilize flhDC mRNA.

The effects of various alleles of the FlgM T3S chaperone $\sigma^{28}$ encoded by the fliA gene were explored. These included FlgM bypass alleles of fliA that allow class 3 transcription in the presence of FlgM, the promoter binding-defective double-mutant R91C L207P, the ATG start codon mutant (from GTG), and a canonical ribosome binding sequence mutant (labeled CRBS). The FlgM bypass alleles H14D, H14N, V33E, T138I, L199R and E203D all have similar affinities for RNAP with a measured $K_d$ for core RNAP of 2.0, 1.9, 0.7, 0.8, 1.2 and 1.4 nM, respectively compared to 0.9 for wild-type $\sigma^{28}$. The relative affinities for FlgM of the H14D and H14N are the same as wild-type, while the V33E, T138I, L199R and E203D alleles have 10-, 20-, 600- and 10-fold reduced affinities, respectively. The V33E allele showed the lowest levels of secreted FlgM while L199R had about half the secreted level of FlgM as wild-type. However, the low cellular level of V33E $\sigma^{28}$ allele shows that it is a limiting $\sigma^{28}$ that is responsible for the reduced secreted FlgM levels observed. The reduced affinity of T138I and V203E for FlgM is not a limiting factor under FlgM over-expressing conditions (from $P_{araBAD}$). The R91C L207P promoter binding-defective double-mutation resulted in reduced $\sigma^{28}$ cellular levels that corresponded to a reduced level of secreted FlgM while the H14D and H14N alleles had the opposite effect. The H14D and H14N alleles resulted in elevated cellular $\sigma^{28}$ levels and corresponded to increased levels of secreted FlgM. Addition of H14D or H14N to the R91C L207P double-mutant resulted in increase $\sigma^{28}$ levels and secreted levels of FlgM. The ATG with or without the additional H14N substitution or the canonical ribosome binding sequence mutant (ATG CRBS) all resulted in elevated cellular $\sigma^{28}$ and secreted FlgM levels. These results show that increasing cellular levels of $\sigma^{28}$ results in a corresponding increase in FlgM secretion under FlgM over-expression conditions.

Removal of late secretion competitors of FlgM secretion or their cognate chaperones had mixed results. Of the 4 secretion competitors FlgK, FlgL, FliD and FliC/FljB only removal of the filament late secretion substrates FliC/FljB had a significant effect of FlgM secretion. The amount of filament subunits in the flagellum is about 1000 times that of the other three components. Removal of the FliD secretion chaperone FliT also increased FlgM secretion independent of its role on increasing the stability of FliD. FliT is a regulator of FlhD4C2 promoter activation and its removal results in increased HBB secretion conduits per cell. Removal of filament T3S chaperone protein, FliS, resulted in a 3-fold increase in secreted FlgM levels while removal of the FlgK and FlgL T3 S chaperone had no effect. As fliS and fliT are cotranscribed in the same operon (fliS is upstream of fliT), any deletion mutation of fliS may affect fliT gene expression. A flagellar phase variation mutant allele, fljB$^{enx}$ vh2, showed a significant increase in secreted FlgM levels compared to the hin-5717 allele. Increased secreted FlgM levels were also observed in the Spi1, even when the cells were grown under Spi1 non-inducing conditions.

Removal of cellular proteases also produced mixed results on FlgM secretion. The ClpXP protease regulates the number of flagella per cell by degradation of the FlhD4C2 complex, which is directed by the YdiV protein. YdiV is produced during poor nutrient growth conditions. YdiV binds the FlhD component of the FlhD4C2, which prevents further interaction between FlhD4C2 and DNA. YdiV then targets FlhD4C2 to ClpXP protease for degradation. Removal of either ClpX or ClpP resulted increased FlgM secreted levels. Removal of DegP or OmpT proteases were also tested for effects on FlgM secretion and no effect was observed.

The last variable tested on secreted levels of over-expressed FlgM was ionic strength. Type III secretion is induced by high osmolarity. The effect of NaCl and KCl concentration on FlgM secretion was tested and it was observed that addition of NaCl to 200 mM or KCl to 200-400 mM resulted in a about 4-fold increase in secreted FlgM levels compared to 100 mM NaCl, which is close to the concentration of NaCl in LB (0.5% or 86 mM). The NaCl effect was due to increased potential of the proton motive force. However, the same effect was observed with the addition of KCl showing that it is simply ionic strength that controls FlgM secreted levels. Ionic strength can result in increased stability of FlhD4C2.

After determining the effects of different mutations on secreted levels of FlgM the observations were combined to construct some strains that maximize the amount of FlgM secreted from the cell. All of the strains containing fliB-T, clpX, or flhD8089 increased the FlgM secretion about 5-fold of that of wild type strain, and the combination did not increase FlgM secretion further more. This is because nearly all of the FlgM was secreted, and only trace amount of FlgM accumulated in the cell. So when different mutations were combined together, the expression level of the FlgM became limiting factor of FlgM secretion level.

Finally, a disulfide-rich small peptide δ-SVIE contoxin was fused to FlgM, to test whether the peptide can be secreted and how the mutations and ion concentration affect its secretion. Both FlgM-6His-TEV-δ-SVIE and FlgM-6His-ETK-δ-SVIE can be secreted to the medium, and the mutations which stimulated FlgM' secretion also increased these fusion proteins secretion. Some combined mutants such as rcsB fliT strain and flhD8089 fljB$^{enx}$ vh2 clpX strain increased FlgM-6H-TEV-δ-SVIE secretion about 50-fold compare to wild type. Another combined strain flhD7793 lrhA ecnR fliB-T ydiV hin-fljA flgKL FlgMN increased the secretion of FlgM-6H-ETK-δ-SVIE over 100-fold compare to wild type strain. The addition of 100 mM NaCl to LB medium can increase the secretion of FlgM-6H-ETK-δ-SVIE in flhD7793 strain, flhD7793 FlgM strain, and flhD7793 FlgM clpX strain. These results indicated that FlgM can be used as a T3S signal to express and purify proteins which are difficult or impossible to do via E coil overexpression system.

C. Example 3

Large-Scale, Type III-Dependent Protein Production Via Direct Secretion into the Growth Medium The use of FlgM as a secretion signal to facilitate secretion of previously difficult to produce proteins, such as conopeptides with numerous disulfide bonds and the A subunit of diphtheria toxin, which is not detectable in the cytoplasm due to its instability, demonstrates the utility of this system for protein production and purification of proteins that otherwise are not produced.

Using lambda RED technology for chromosomal targeting, this system can revolutionize bacterial genetic strain construction. In the desired genetic background the araBAD operon can be replaced by a tetRA element. The tetRA element can be the tetR and tetA genes from transposon Tn10 that code for a tetracycline efflux pump (TetA), which confers resistance to tetracycline, and the TetR repressor. This can be accomplished by PCR-amplification of the tetRA element using 48-mer oligonucleotides. One ologo has 40 bases of homology to the 5' side of the beginning of the araB gene followed by 18 bases that can amplify from the 5'-tetR end of tetRA. The second has 40 bases of homology to the 3' side of the end of the araD gene followed by 18 bases that can amplify from the 3'-tetA end of tetRA. PCR amplification of tetRA-containing DNA produces the tetRA element flanked by 40 bases of homology to the target. Introduction of the amplified fragment into a strain that expresses the lambda recombination genes (RED) results in recombination using the 40 bases of flanking homology resulting in deletion of the araBAD genes that are replaced by tetRA (ΔaraBAD::tetRA where Δ is genetic nomenclature for deletion and :: is genetic nomenclature for insertion). The advantage of the tetRA element is that it can be selected for and against. The presence of the tetRA element in the chromosome confers tetracycline resistance, but also confers sensitivity of fusaric acid. Thus, when the FlgM coding sequence is PCR amplified with the same 40 bases of homology 5' to araB and 3' to araD in the presence of lambda RED and plated on fusaric acid medium, this selects for recombination that replaces the tetRA of ΔaraBAD::tetRA with FlgM$^+$ sequence resulting in ΔaraBAD::FlgM$^+$ where the FlgM$^+$ gene is now transcribed from the arabinose-inducible araBAD promoter. Next, by the same method tetRA is placed downstream of FlgM$^+$ at araBAD resulting in ΔaraBAD::FlgM$^+$-tetRA followed by replacement that tetRA with protein X resulting in a FlgM-X fusion that is expressed by addition of arabinose to the growth medium. Using this system any fusion of any protein to FlgM under arabinose induction can be constructed with intervening protease cleavage sequences to facilitate final purification of a protein of interest.

1. Strain & Conditions Optimizations.

Figure 10A:
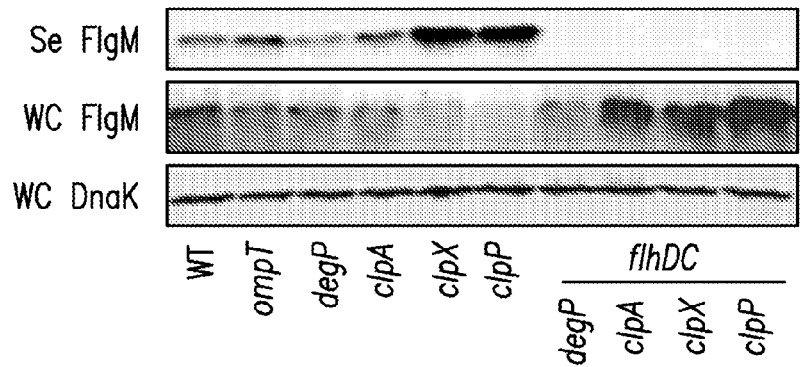
Figure 10B:
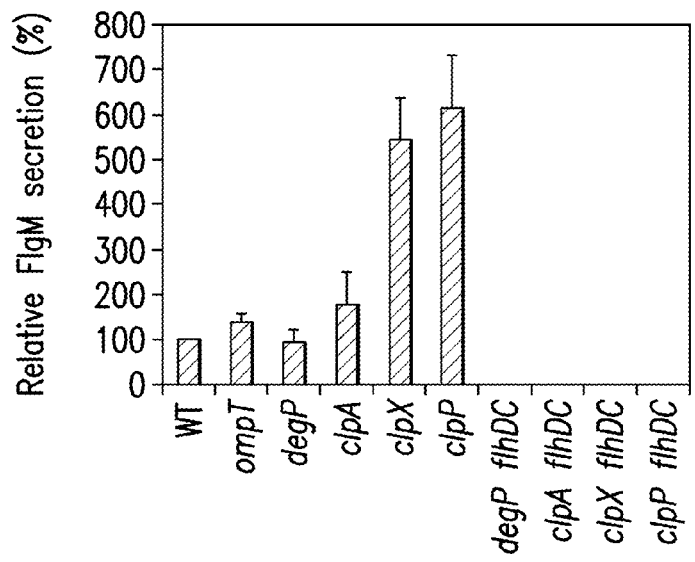
Figure 10B:
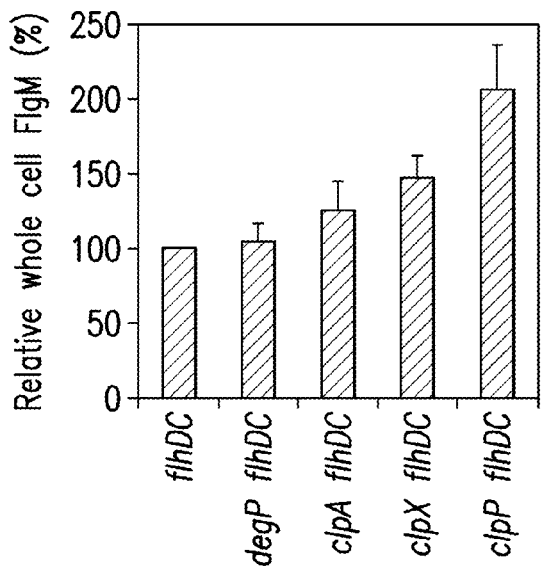
Figure 10C:
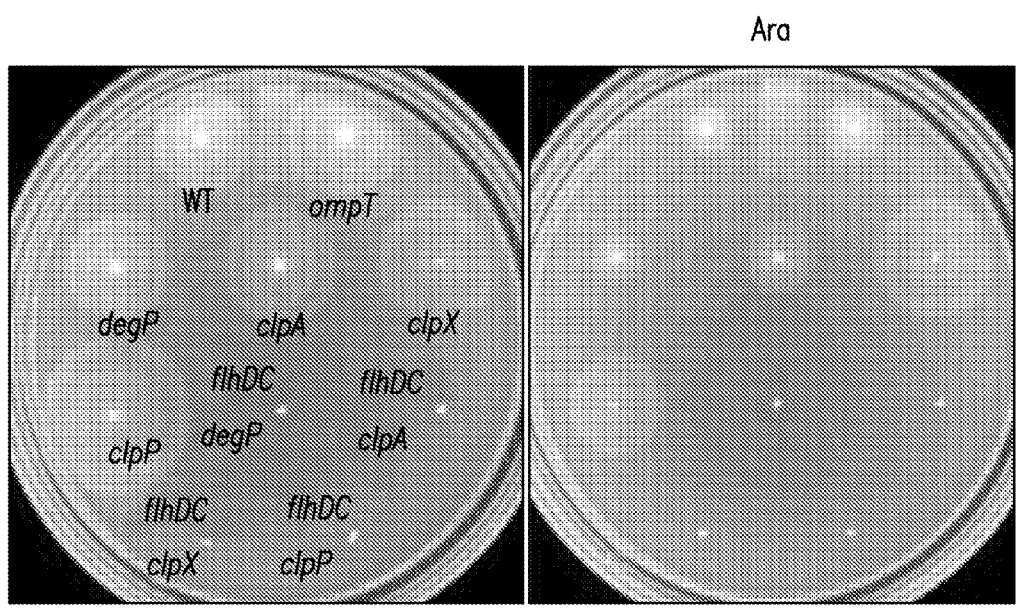

Optimum secretion strains can be identified. The promoter up allele of the flhDC promoter, flhD7793, and the allele resulting from the replacement of the flhDC promoter with the anhydrotetracycline (AnTc) inducible tetA promoter, flhD8089, each results in substantial increase in FlgM secretion that is greater than that observed by removal of inhibitors of flhDC transcription: FliT, LrhA, DskA, RcsB or EcnR (FIG. 5A). The AnTc-inducible flhDC operon (the flhD8089 allele) is of note because it is deleted for the binding sites of all known inhibitor proteins and dependent only on AnTc for expression. The flhD8089 allele can be combined with the fliA(σ$^{28}$) H14N allele of the secretion chaperone of FlgM, which showed to greatest positive effect on FlgM secretion (FIG. 6A). Further combination with a clpX protease mutant allele can increase secretion (FIG. 10A). Using this genetic background in a strain that also expresses a protein of interest fused to the FlgM flagellar type III secretion signal can increase production of the protein of interest, especially if grown in the presence of 200 mM NaCl or KCl (FIG. 11A).

2. The σ$^{28}$ Purification Column.

The σ$^{28}$ protein is the product of the fliA gene and the type III secretion chaperone for FlgM. Increased σ$^{28}$ levels result in increased levels of secreted FlgM-fused protein substrate (FIG. 6A). The σ$^{28}$ protein can also be used for a protein purification system. The apparent K$_d$ of the FlgM-σ$^{28}$ complex is 2×10$^{-10}$ M. This remarkably high affinity means that purification of FlgM can result in co-purification of σ$^{28}$ and vice versa. FlgM fused to a chitin-binding domain (CBD) sandwiched by an intein self-cleavage site has been constructed. When extracts from cells expressing this fusion chimera were poured over a chitin column the FlgM-intein-CBD chimera in complex with σ$^{28}$ bound the column. Addition of a reducing agent catalyzed intein self-cleavage releasing purified FlgM-σ$^{28}$ complex. Making a chitin column bound by σ$^{28}$-CBD can use this aspect. The spent growth medium of FlgM-intein-X chimera produced from our flagellar secretion strain, where X is the protein of interest, can be poured over such a column. Induction of intein self-cleavage can release protein X in pure form. This can provide a low-cost high-yield protein production system.

Proteins that must remain in oxidative conditions to maintain an active conformation can have a protease cleavage sequence, such as enterokinase, which cleaves under oxidative conditions, in place of the intein.

The disclosed system and methods can also be developed into E. coli to obtain the protein secretion and production with the E. coli flagellar T3 S system that was achieved in Salmonella. This can be expanded to include other strains such as thermo-tolerant strains. Proteins from thermo tolerant strains are often used in crystallographic and NMR studies because of increased protein stabilities at high temperatures that facilitate structural analysis.

A SPI1 injectisome T3S system for protein production can be developed. The SipA, SipB and SipC proteins are secreted at high levels by the SPI1 injectisome T3S system (FIG. 14). These proteins can be tested to determine if they can be used to facilitate protein secretion in fusion constructs and develop a protein production system similar to the flagellar system. Spi1 production is under the control of HilD and it has been determined that controlled expression of hilD$^+$ from the arabinose-inducible P$_{araBAD}$ promoter results in high levels of Spi1 mRNA production.

Figure 15A:
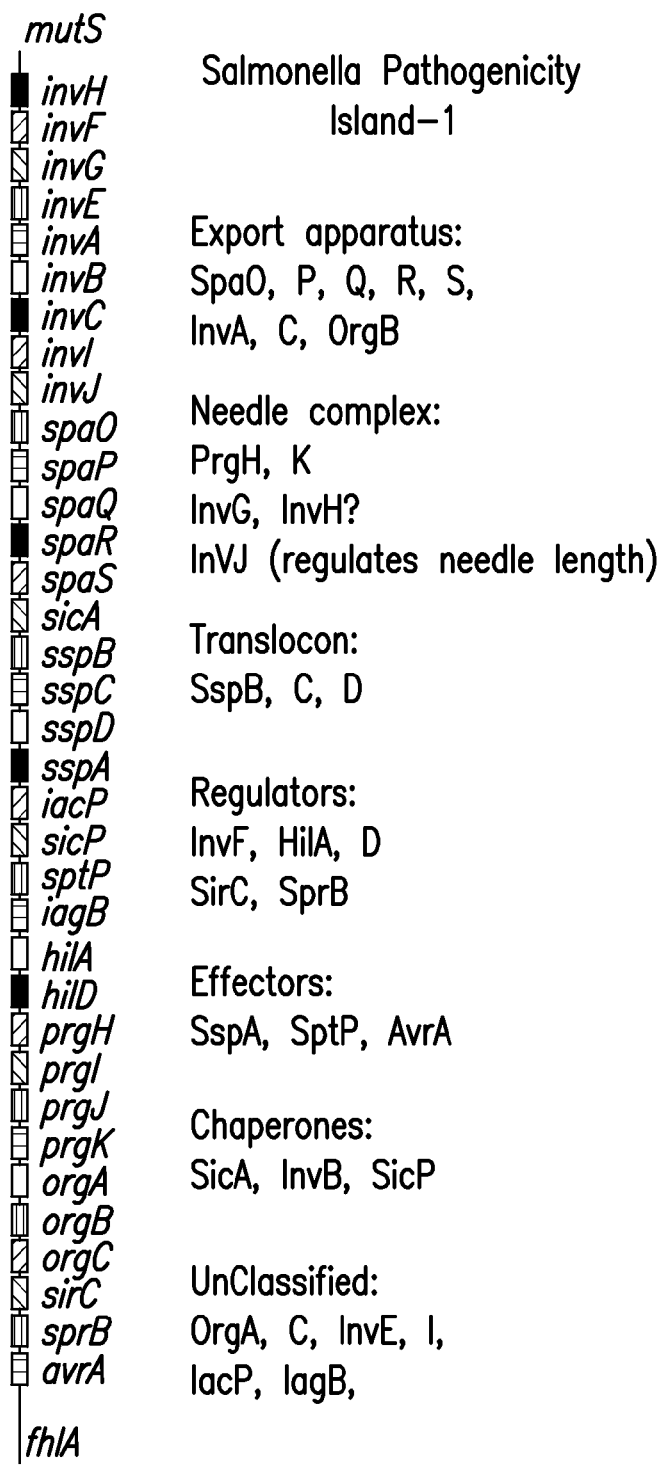

E. coli has essentially the identical flagellar T3S as Salmonella, making it straightforward to reconstruct the optimal secretion strain in E. coli. However, E. coli lacks the SPI1 system and thus the entire SPI1 set of genes can be inserted into the E. coli chromosome. As shown in FIG. 15A, the SPI1 genes are organized into a single "pathogenicity island" which can be amplified and inserted into the E. coli chromosome using the lambda RED technology. The export apparatus and needle complex genes can be used, while the hilA+ gene will be inserted into the araBAD locus to allow for arabinose induction of SPI1.

The SPI1 system can also be used to develop a membrane-protein purification system. Such as system can revolutionize membrane protein production and characterization. The SPI1 system works by inserting into the cytoplasmic membrane of host cells through its translocon tip (see FIG. 16). Modifying injectisome needle-length can be done in order to develop a minimal functional needle that is as short as possible yet still allows for normal translocon formation and insertion into the membrane of host cells. Minimizing the needle length through which a membrane protein must traverse can be beneficial. This can be coupled to translocation of secretion of membrane proteins using the SPI1 system into artificial membrane vesicles.

REFERENCES

1. Abramoff, M. D., P. J. Magelhaes, and S. J. Ram. 2004. Image Processing with ImageJ. Biophotonics International 11:36-42.
2. Aldridge, P. D., J. E. Karlinsey, C. Aldridge, C. Birchall, D. Thompson, J. Yagasaki, and K. T. Hughes. 2006. The flagellar-specific transcription factor, sigma28, is the Type III secretion chaperone for the flagellar-specific anti-sigma28 factor FlgM. Genes Dev. 20:2315-2326.

3. Bulaj, G., P. J. West, J. E. Garrett, M. Watkins, M. Marsh, M.-M. Zhang, R. S. Norton, B. J. Smith, D. Yoshikami, and B. M. Olivera. 2005. Novel conotoxins from *Conus striatus* and *Conus kinoshitai* selectively block TTX-resistant sodium channels. Biochemistry 44:7259-7265.
4. Chadsey, M. S., and K. T. Hughes. 2001. A multipartite interaction between *Salmonella* transcription factor sigma28 and its anti-sigma factor FlgM: implications for sigma28 holoenzyme destabilization through stepwise binding. Journal of Molecular Biology 306:915-929.
5. Chadsey, M. S., J. E. Karlinsey, and K. T. Hughes. 1998. The flagellar anti-sigma factor FlgM actively dissociates *Salmonella typhimurium* sigma28 RNA polymerase holoenzyme. Genes Dev 12:3123-3136.
6. Chahine, M., L. Q. Chen, N. Fotouhi, R. Walsky, D. Fry, V. Santarelli, R. Horn, and R. G. Kallen. 1995. Characterizing the mu-conotoxin binding site on voltage-sensitive sodium channels with toxin analogs and channel mutations. Recept Channels 3:161-174.
7. Chahine, M., J. Sirois, P. Marcotte, L. Chen, and R. G. Kallen. 1998. Extrapore residues of the S5-S6 loop of domain 2 of the voltage-gated skeletal muscle sodium channel (rSkM1) contribute to the mu-conotoxin GIIIA binding site. Biophys J 75:236-246.
8. Chang, N. S., R. J. French, G. M. Lipkind, H. A. Fozzard, and S. Dudley, Jr. 1998. Predominant interactions between mu-conotoxin Arg-13 and the skeletal muscle Na+ channel localized by mutant cycle analysis. Biochemistry 37:4407-4419.
9. Che, N., L. Wang, Y. Gao, and C. An. 2009. Soluble expression and one-step purification of a neurotoxin Huwentoxin-I in *Escherichia coli*. Protein Expression and Purification 65:154-159.
10. Chevance, F. F. V., and K. T. Hughes. 2008. Coordinating assembly of a bacterial macromolecular machine. Nat Rev Microbiol 6:455-465.
11. Dobo, J., J. Varga, R. Sajo, B. M. Vegh, P. Gal, P. Zavodszky, and F. Vonderviszt. 2010. Application of a short, disordered N-terminal flagellin segment, a fully functional flagellar type III export signal, to expression of secreted proteins. Applied and Environmental Microbiology 76:891-899.
12. Dudley, S. C., H. Todt, G. Lipkind, and H. A. Fozzard. 1995. A mu-conotoxin-insensitive Na+ channel mutant: possible localization of a binding site at the outer vestibule. Biophys J 69:1657-1665.
13. Erhardt, M., and K. T. Hughes. 2010. C-ring requirement in flagellar type III secretion is bypassed by FlhDC upregulation. Mol Microbiol 75:376-393.
14. Erhardt, M., K. Namba, and K. T. Hughes. 2010. Bacterial nanomachines: the flagellum and type III injectisome. Cold Spring Harb Perspect Biol 2:a000299.
15. Fiedler, B., M.-M. Zhang, O. Buczek, L. Azam, G. Bulaj, R. S. Norton, B. M. Olivera, and D. Yoshikami. 2008. Specificity, affinity and efficacy of iota-conotoxin RXIA, an agonist of voltage-gated sodium channels Na(V)1.2, 1.6 and 1.7. Biochem Pharmacol 75:2334-2344.
16. Frye, J., J. E. Karlinsey, H. R. Felise, B. Marzolf, N. Dowidar, M. McClelland, and K. T. Hughes. 2006. Identification of new flagellar genes of *Salmonella enterica* serovar *Typhimurium*. J Bacteriol 188:2233-2243.
17. Green, B. R., P. Catlin, M.-M. Zhang, B. Fiedler, W. Bayudan, A. Morrison, R. S. Norton, B. J. Smith, D. Yoshikami, B. M. Olivera, and G. Bulaj. 2007. Conotoxins containing nonnatural backbone spacers: cladistic-based design, chemical synthesis, and improved analgesic activity. Chemistry & Biology 14:399-407.
18. Hughes, K. T., K. L. Gillen, M. J. Semon, and J. E. Karlinsey. 1993. Sensing structural intermediates in bacterial flagellar assembly by export of a negative regulator. Science 262:1277-1280.
19. Hui, K., G. Lipkind, H. A. Fozzard, and R. J. French. 2002. Electrostatic and steric contributions to block of the skeletal muscle sodium channel by mu-conotoxin. J Gen Physiol 119:45-54.
20. Jones, R. M., and G. Bulaj. 2000. Conotoxins—new vistas for peptide therapeutics. Curr Pharm Des 6:1249-1285.
21. Karlinsey, J. E. 2007. lambda-Red genetic engineering in *Salmonella enterica* serovar *Typhimurium*. Meth Enzymol 421:199-209.
22. Karlinsey, J. E., S. Tanaka, V. Bettenworth, S. Yamaguchi, W. Boos, S. I. Aizawa, and K. T. Hughes. 2000. Completion of the hook-basal body complex of the *Salmonella typhimurium* flagellum is coupled to FlgM secretion and fliC transcription. Mol. Microbiol. 37:1220-1231.
23. Kutsukake, K. 1994. Excretion of the anti-sigma factor through a flagellar substructure couples flagellar gene expression with flagellar assembly in *Salmonella typhimurium*. Mol Gen Genet 243:605-612.
24. Lee, H. J., and K. T. Hughes. 2006. Posttranscriptional control of the *Salmonella enterica* flagellar hook protein FlgE. J Bacteriol 188:3308-3316.
25. Lehnen, D., C. Blumer, T. Polen, B. Wackwitz, V. F. Wendisch, and G. Unden. 2002. LrhA as a new transcriptional key regulator of flagella, motility and chemotaxis genes in *Escherichia coli*. Mol Microbiol 45:521-532.
26. Miljanich, G. 1997. Venom peptides as human pharmaceuticals. Sci Med 4:6.
27. Miljanich, G. P. 2004. Ziconotide: neuronal calcium channel blocker for treating severe chronic pain. Curr Med Chem 11:3029-3040.
28. Nakamura, M., Y. Niwa, Y. Ishida, T. Kohno, K. Sato, Y. Oba, and H. Nakamura. 2001. Modification of Arg-13 of mu-conotoxin GIIIA with piperidinyl-Arg analogs and their relation to the inhibition of sodium channels. FEBS Left 503:107-110.
29. Ohnishi, K., K. Kutsukake, H. Suzuki, and T. Lino. 1992. A novel transcriptional regulation mechanism in the flagellar regulon of *Salmonella typhimurium*: an antisigma factor inhibits the activity of the flagellum-specific sigma factor, sigma F. Mol Microbiol 6:3149-3157.
30. Olivera, B. 2000. ω-Conotoxin MVIIA: From Marine Snail Venom to Analgesic Drug. Drugs from the Sea (Fusetani, N., ed): pp. 77-85.
31. Sanderson, K. E., and J. R. Roth. 1983. Linkage map of *Salmonella typhimurium*, Edition VI. Microbiol. Rev. 47:410-453.
32. Takaya, A., M. Erhardt, K. Karata, K. Winterberg, T. Yamamoto, and K. T. Hughes. 2012. YdiV: a dual function protein that targets FlhDC for ClpXP-dependent degradation by promoting release of DNA-bound FlhDC complex. Molecular microbiology 83:1268-1284.
33. Terlau, H., and B. M. Olivera. 2004. Conus venoms: a rich source of novel ion channel-targeted peptides. Physiol Rev 84:41-68.
34. Wozniak, C., C. Lee, and K. Hughes. 2008. T-POP array identifies EcnR and PefI-SrgD as novel regulators of flagellar gene expression. J Bacteriol.
35. Yao, S., M.-M. Zhang, D. Yoshikami, L. Azam, B. M. Olivera, G. Bulaj, and R. S. Norton. 2008. Structure, dynamics, and selectivity of the sodium channel blocker mu-conotoxin SIIIA. Biochemistry 47:10940-10949.

36. Frye, J., J. E. Karlinsey, H. R. Felise, B. Marzolf, N. Dowidar, M. McClelland, and K. T. Hughes. 2006. Identification of new flagellar genes of *Salmonella enterica* serovar *Typhimurium*. J Bacteriol 188:2233-2243.
1. Aldridge, C., K. Poonchareon, S. Saini, T. Ewen, A. Soloyva, C. V. Rao, K. Imada, T. Minamino, and P. D. Aldridge. 2010. The interaction dynamics of a negative feedback loop regulates flagellar number in *Salmonella enterica* serovar *Typhimurium*. Mol. Microbiol. 78:1416-1430.
2. Aldridge, P. D., J. E. Karlinsey, C. Aldridge, C. Birchall, D. Thompson, J. Yagasaki, and K. T. Hughes. 2006. The flagellar-specific transcription factor, sigma28, is the Type III secretion chaperone for the flagellar-specific anti-sigma28 factor FlgM. Genes Dev. 20:2315-2326.
3. Auvray, F., J. Thomas, G. M. Fraser, and C. Hughes. 2001. Flagellin polymerisation control by a cytosolic export chaperone. J. Mol. Biol. 308:221-229.
4. Baneyx, F., and G. Georgiuo. 1990. In vivo degradation of secreted fusion proteins by the *Escherichia coli* outer membrane protease OmpT. J. Bacteriol. 172:491-494.
5. Barembruch, C., and R. Hengge. 2007. Cellular levels and activity of the flagellar sigma factor FliA of *Escherichia coli* are controlled by FlgM-modulated proteolysis. Mol. Microbiol. 65:76-89.
6. Berg, H. C., and R. A. Anderson. 1973. Bacteria swim by rotating their flagellar filaments. Nature 245:380-382.
7. Bonifield, H. R., and K. T. Hughes. 2003. Flagellar phase variation in *Salmonella enterica* serovar *Typhimurium* is mediated by a posttranscriptional control mechanism. J. Bacteriol. 185:3567-3574.
8. Chadsey, M. S., and K. T. Hughes. 2001. A multipartite interaction between *Salmonella* transcription factor sigma28 and its anti-sigma factor FlgM: implications for sigma28 holoenzyme destabilization through stepwise binding. J. Mol. Biol. 306:915-929.
9. Chevance, F. F., and K. T. Hughes. 2008. Coordinating assembly of a bacterial macromolecular machine. Nat. Rev. Microbiol. 6:455-465.
10. Chubiz, J. E., Y. A. Golubeva, D. Lin, L. D. Miller, and J. M. Slauch. 2010. FliZ regulates expression of the *Salmonella* pathogenicity island 1 invasion locus by controlling HilD protein activity in *Salmonella enterica* serovar *typhimurium*. J. Bacteriol. 192:6261-6270.
11. Datsenko, K. A., and B. L. Wanner. 2000. One-step inactivation of chromosomal genes in *Escherichia coli* K-12 using PCR products. Proc. Natl. Acad. Sci. USA 97:6640-6645.
12. Daughdrill, G. W., M. S. Chadsey, J. E. Karlinsey, K. T. Hughes, and F. W. Dahlquist. 1997. The C-terminal half of the anti-sigma factor, FlgM, becomes structured when bound to its target, sigma 28. Nat. Struct. Biol. 4:285-291.
13. Davis, R. W., D. Botstein, and J. R. Roth. 1980. Advanced Bacterial Genetics. Cold Spring Harbor Laboratory, Cold Spring Harbor, N.Y.
14. Dorel, C., P. Lejeune, and A. Rodrigue. 2006. The Cpx system of *Escherichia coli*, a strategic signaling pathway for confronting adverse conditions and for settling biofilm communities? Res. Microbiol. 157:306-314.
15. Ellermeier, C. D., and J. M. Slauch. 2003. RtsA and RtsB coordinately regulate expression of the invasion and flagellar genes in *Salmonella enterica* serovar *Typhimurium*. J. Bacteriol. 185:5096-5108.
16. Enomoto, M., and B. A. Stocker. 1975. Integration, at hag or elsewhere, of H2 (phase-2 flagellin) genes transduced from *Salmonella* to *Escherichia coli*. Genetics 81:595-614.
17. Erhardt, M., and K. T. Hughes. 2010. C-ring requirement in flagellar type III secretion is bypassed by FlhDC upregulation. Mol. Microbiol. 75:376-393.
18. Fattori, J., A. Prando, A. M. Martins, F. H. Rodrigues, and L. Tasic. 2011. Bacterial secretion chaperones. Protein Pept. Lett. 18:158-166.
19. Flynn, J. M., S. B. Neher, Y. I. Kim, R. T. Sauer, and T. A. Baker. 2003. Proteomic discovery of cellular substrates of the ClpXP protease reveals five classes of ClpX-recognition signals. Mol. Cell 11:671-683.
20. Francez-Charlot, A., B. Laugel, A. Van Gemert, N. Dubarry, F. Wiorowski, M. P. Castanie-Cornet, C. Gutierrez, and K. Cam. 2003. RcsCDB His-Asp phosphorelay system negatively regulates the flhDC operon in *Escherichia coli*. Mol. Microbiol. 49:823-832.
21. Fraser, G. M., J. C. Bennett, and C. Hughes. 1999. Substrate-specific binding of hook-associated proteins by FlgN and FliT, putative chaperones for flagellum assembly. Mol. Microbiol. 32:569-580.
22. Galán, J. E., and R. r. Curtiss. 1990. Expression of *Salmonella typhimurium* genes required for invasion is regulated by changes in DNA supercoiling. Infect. Immun 58:1879-1885.
23. Gillen, K. L., and K. T. Hughes. 1991. Molecular characterization of FlgM, a gene encoding a negative regulator of flagellin synthesis in *Salmonella typhimurium*. J. Bacteriol. 173:6453-6459.
24. Gillen, K. L., and K. T. Hughes. 1993. Transcription from two promoters and autoregulation contribute to the control of expression of the *Salmonella typhimurium* flagellar regulatory gene FlgM. J. Bacteriol. 175:7006-7015.
25. Hughes, K. T., A. Dessen, J. P. Gray, and C. Grubmeyer. 1993. The *Salmonella typhimurium* nadC gene: sequence determination by use of Mud-P22 and purification of quinolinate phosphoribosyltransferase. J. Bacteriol. 175: 479-486.
26. Hughes, K. T., K. L. Gillen, M. J. Semon, and J. E. Karlinsey. 1993. Sensing structural intermediates in bacterial flagellar assembly by export of a negative regulator. Science 262:1277-1280.
27. Ikebe, T., S. Iyoda, and K. Kutsukake. 1999. Structure and expression of the fliA operon of *Salmonella typhimurium*. Microbiol. 145:1389-1396.
28. Iyoda, S., T. Kamidoi, K. Hirose, K. Kutsukake, and H. Watanabe. 2001. A flagellar gene fliZ regulates the expression of invasion genes and virulence phenotype in *Salmonella enterica* serovar *Typhimurium*. Microb. Pathog. 30:81-90.
29. Karlinsey, J. E. 2007. lambda-Red genetic engineering in *Salmonella enterica* serovar *Typhimurium*. Meth. Enzymol. 421:199-209.
30. Karlinsey, J. E., J. Lonner, K. L. Brown, and K. T. Hughes. 2000. Translation/secretion coupling by type III secretion systems. Cell 102:487-497.
31. Kutsukake, K. 1994. Excretion of the anti-sigma factor through a flagellar substructure couples flagellar gene expression with flagellar assembly in *Salmonella typhimurium*. Mol. Gen. Genet. 243:605-612.
32. Lehnen, D., C. Blumer, T. Polen, B. Wackwitz, V. F. Wendisch, and G. Unden. 2002. LrhA as a new transcriptional key regulator of flagella, motility and chemotaxis genes in *Escherichia coli*. Mol. Microbiol. 45:521-532.
33. Lemke, J. J., T. Durfee, and R. L. Gourse. 2009. DksA and ppGpp directly regulate transcription of the *Escherichia coli* flagellar cascade. Mol. Microbiol. 74:1368-1379.

34. Lucas, R. L., C. P. Lostroh, C. C. DiRusso, M. P. Spector, B. L. Wanner, and C. A. Lee. 2000. Multiple factors independently regulate hilA and invasion gene expression in *Salmonella enterica* serovar *typhimurium*. J. Bacteriol. 182:1872-1882.
35. Macnab, R. M. 2003. How bacteria assemble flagella. Annu. Rev. Microbiol. 57:77-100.
36. Macnab, R. M. 2004. Type III flagellar protein export and flagellar assembly. Biochim. Biophys. Acta 1694:207-217.
37. Merdanovic, M., T. Clausen, M. Kaiser, R. Huber, and M. Ehrmann. 2011. Protein quality control in the bacterial periplasm. Annu. Rev. Microbiol. 65:149-168.
38. Minamino, T., and K. Namba. 2008. Distinct roles of the ATPase and proton motive force in bacterial flagellar protein export. Nature 451:485-488.
39. Namba, K. 2001. Roles of partly unfolded conformations in macromolecular self-assembly. Genes Cells 6:1-12.
40. Ohnishi, K., K. Kutsukake, H. Suzuki, and T. Iino. 1990. Gene fliA encodes an alternative sigma factor specific for flagellar operons in *Salmonella typhimurium*. Mol. Gen. Genet. 221:139-147.
41. Ohnishi, K., K. Kutsukake, H. Suzuki, and T. Lino. 1992. A novel transcriptional regulation mechanism in the flagellar regulon of *Salmonella typhimurium*: an antisigma factor inhibits the activity of the flagellum-specific sigma factor, sigma F. Mol. Microbiol. 6:3149-3157.
42. Osterberg, S., T. del Peso-Santos, and V. Shingler. 2011. Regulation of alternative sigma factor use. Annu. Rev. Microbiol. 65:37-55.
43. Paul, K., M. Erhardt, T. Hirano, D. F. Blair, and K. T. Hughes. 2008. Energy source of flagellar type III secretion. Nature 451:489-492.
44. Singer, H. M., M. Erhardt, A. M. Steiner, M. M. Zhang, D. Yoshikami, G. Bulaj, B. M. Olivera, and K. T. Hughes. 2012. Selective purification of recombinant neuroactive peptides using the flagellar type III secretion system. MBio 3.
45. Sorenson, M. K., S. S. Ray, and S. A. Darst. 2004. Crystal structure of the flagellar sigma/anti-sigma complex sigma(28)/FlgM reveals an intact sigma factor in an inactive conformation. Mol. Cell 14:127-138.
46. Sourjik, V., and N. S. Wingreen. 2012. Responding to chemical gradients: bacterial chemotaxis. Curr. Opin. Cell Biol. 24:262-268.
47. Takaya, A., M. Erhardt, K. Karata, K. Winterberg, T. Yamamoto, and K. T. Hughes. 2012. YdiV: a dual function protein that targets FlhDC for ClpXP-dependent degradation by promoting release of DNA-bound FlhDC complex. Mol. Microbiol. 83:1268-1284.
48. Tomoyasu, T., T. Ohkishi, Y. Ukyo, A. Tokumitsu, A. Takaya, M. Suzuki, K. Sekiya, H. Matsui, K. Kutsukake, and T. Yamamoto. 2002. The ClpXP ATP-dependent protease regulates flagellum synthesis in *Salmonella enterica* serovar *Typhimurium*. J. Bacteriol. 184:645-653.
49. Wada, T., T. Morizane, T. Abo, A. Tominaga, K. Inoue-Tanaka, and K. Kutsukake. 2011. EAL domain protein YdiV acts as an anti-FlhD4C2 factor responsible for nutritional control of the flagellar regulon in *Salmonella enterica* Serovar *Typhimurium*. J. Bacteriol. 193:1600-1611.
50. Wang, Q., Y. Zhao, M. McClelland, and R. M. Harshey. 2007. The RcsCDB signaling system and swarming motility in *Salmonella enterica* serovar *Typhimurium*: dual regulation of flagellar and SPI-2 virulence genes. J. Bacteriol. 189:8447-8457.
51. Wang, S., R. T. Fleming, E. M. Westbrook, P. Matsumura, and D. B. McKay. 2006. Structure of the *Escherichia coli* FlhDC complex, a prokaryotic heteromeric regulator of transcription. J. Mol. Biol. 355:798-808.
52. Wei, B. L., A. M. Brun-Zinkernagel, J. W. Simecka, B. M. Pruss, P. Babitzke, and T. Romeo. 2001. Positive regulation of motility and flhDC expression by the RNA-binding protein CsrA of *Escherichia coli*. Molecular microbiology Mol. Microbiol. 40:245-256.
53. Wozniak, C. E., C. Lee, and K. T. Hughes. 2009. T-POP array identifies EcnR and PefI-SrgD as novel regulators of flagellar gene expression. J. Bacteriol. 191:1498-1508.
54. Yamamoto, S., and K. Kutsukake. 2006. FliT acts as an anti-FlhD2C2 factor in the transcriptional control of the flagellar regulon in *Salmonella enterica* serovar *Typhimurium*. J. Bacteriol. 188:6703-6708.
55. Yanagihara, S., S. Iyoda, K. Ohnishi, T. Iino, and K. Kutsukake. 1999. Structure and transcriptional control of the flagellar master operon of *Salmonella typhimurium*. Genes Genet. Syst. 74:105-111.
56. Yokoseki, T., K. Kutsukake, K. Ohnishi, and T. Iino. 1995. Functional analysis of the flagellar genes in the fliD operon of *Salmonella typhimurium*. Microbiol. 141:1715-1722.

We claim:

1. A vector comprising a FlgM nucleic acid sequence operably linked to a nucleic acid sequence encoding a purification tag, a cleavage site, a nucleic acid sequence of interest, and a transcription control element (TCE), wherein the TCE is heterologous to the FlgM nucleic acid sequence and wherein the 5' to 3' order of: the sequences is the FlgM nucleic acid sequence, the nucleic acid sequence encoding a purification tag, the cleavage site, and the nucleic acid sequence of interest.

2. The vector of claim 1, wherein the purification tag comprises poly-histidine, glutathione S-transferase (GST), Myc, HA, FLAG, or maltose binding protein (MBP).

3. The vector of claim 2, wherein the purification tag is poly-histidine.

4. The vector of claim 1, wherein the FlgM nucleic acid sequence is wild type FlgM.

5. The vector of claim 1, wherein the cleavage site comprises a Tobacco Etch Virus (TEV) protease cleavage site or an Enterokinase (ETK) cleavage site.

6. The vector of claim 1, wherein the nucleic acid sequence of interest encodes a cysteine-rich peptide.

7. The vector of claim 6, wherein the cysteine-rich peptide comprises a neuroactive toxin.

8. The vector of claim 1, wherein the TCE is a constitutive TCE or a regulatable TCE.

9. The vector of claim 8, wherein the regulatable TCE comprises an inducible promoter.

10. The vector of claim 9, wherein the inducible promoter comprises a $P_{araBAD}$ promoter.

11. A bacterial host cell comprising the vector of claim 1.

12. The bacterial host cell of claim 11, wherein the FlgM nucleic acid sequence, the purification tag nucleic acid sequence, the cleavage site, the nucleic acid sequence of interest, and the TCE have inserted into the bacterial host cell in the 5' to 3' order of: the FlgM nucleic acid sequence, the nucleic acid sequence encoding a purification tag, the cleavage site, and the nucleic acid sequence of interest.

13. The bacterial host cell of claim 11, that is a *Salmonella enterica* or an *Escherichia coli* cell.

14. A polypeptide comprising a FlgM peptide operably fused to a cleavage site, a protein of interest, and a purification tag in the N- to C-terminus order of the FlgM peptide, the purification tag, the cleavage site, and the protein of interest.

15. The polypeptide of claim 14, wherein the purification tag comprises poly-histidine.

16. A method of producing a peptide of interest comprising:
(a) culturing a bacterial host cell in culture media, wherein the bacterial host cell comprises a FlgM nucleic acid sequence operably linked to a nucleic acid sequence encoding a purification tag, a cleavage site, a nucleic acid sequence of interest, and a transcription control element (TCE), wherein the TCE is heterologous to the FlgM nucleic acid sequence and wherein the 5' to 3' order of the sequences in the genome is the FlgM nucleic acid sequence, the nucleic acid sequence encoding a purification tag, the cleavage site, and the nucleic acid sequence of interest.

17. The method of claim 16, wherein the purification tag comprises poly-histidine, glutathione S-transferase (GST), Myc, HA, FLAG, or maltose binding protein (MBP).

18. The method of claim 17, wherein the purification tag is poly-histidine.

19. The method of claim 16, wherein the FlgM nucleic acid sequence is wild type FlgM.

20. The method of claim 16, wherein the cleavage site comprises a Tobacco Etch Virus (TEV) protease cleavage site or an Enterokinase (ETK) cleavage site.

21. The method of claim 16, wherein the nucleic acid sequence of interest encodes a cysteine-rich peptide.

22. The method of claim 21, wherein the cysteine-rich peptide is a neuroactive toxin.

23. The method of claim 16, wherein the TCE is a constitutive TCE or a regulatable TCE.

24. The method of claim 16, wherein the regulatable TCE comprises an inducible promoter.

25. The method of claim 24, wherein the inducible promoter comprises a $P_{araBAD}$ promoter.

26. The method of claim 16, wherein the bacterial host cell is a *Salmonella enterica* or an *Escherichia coli* cell.

27. The method of claim 16, further comprising: (b) purifying the peptide of interest from the culture media.

28. The method of claim 27, wherein step (b) comprises use of an affinity column.

29. The method of claim 28, wherein the affinity column is a $\sigma^{28}$ affinity column.

30. The method of claim 16, wherein the bacterial host cell is cultured in media comprising about 200 mM to about 400 mM NaCl or KCl and wherein more of the peptide of interest is produced as compared to bacterial host cells cultured in media comprising 100 mM NaCl or KCl, respectively.

* * * * *

SEQUENCE LISTING

```
<160> NUMBER OF SEQ ID NOS: 74

<210> SEQ ID NO 1
<211> LENGTH: 66
<212> TYPE: DNA
<213> ORGANISM: Artificial Sequence
<220> FEATURE:
<223> OTHER INFORMATION: synthetic construct; SIIIA primer

<400> SEQUENCE: 1
cagaactgct gcaacggcgg ctgcagcagc aaatggtgcc gcgatcatgc gcgctgctgc     60
ggccgc                                                               66

<210> SEQ ID NO 2
<211> LENGTH: 22
<212> TYPE: PRT
<213> ORGANISM: Artificial Sequence
<220> FEATURE:
```

<223> OTHER INFORMATION: synthetic construct; SIIIA peptide

<400> SEQUENCE: 2

Gln Asn Cys Cys Asn Gly Gly Cys Ser Ser Lys Trp Cys Arg Asp His
1               5                   10                  15

Ala Arg Cys Cys Gly Arg
            20

<210> SEQ ID NO 3
<211> LENGTH: 21
<212> TYPE: DNA
<213> ORGANISM: Artificial Sequence
<220> FEATURE:
<223> OTHER INFORMATION: synthetic construct; SIIIA primer

<400> SEQUENCE: 3
gcggccgcag cagcgcgcat g                                         21

<210> SEQ ID NO 4
<211> LENGTH: 7
<212> TYPE: PRT
<213> ORGANISM: Artificial Sequence
<220> FEATURE:
<223> OTHER INFORMATION: synthetic construct; TEV protease cleavage site

<400> SEQUENCE: 4

Glu Asn Leu Tyr Phe Gln Gly
1               5

<210> SEQ ID NO 5
<211> LENGTH: 18
<212> TYPE: DNA
<213> ORGANISM: Artificial Sequence
<220> FEATURE:
<223> OTHER INFORMATION: synthetic construct; histidine tag

<400> SEQUENCE: 5
catcaccatc accatcac                                             18

<210> SEQ ID NO 6
<211> LENGTH: 51
<212> TYPE: DNA
<213> ORGANISM: Artificial Sequence
<220> FEATURE:
<223> OTHER INFORMATION: synthetic construct; FlgM primer

<400> SEQUENCE: 6
cgggatcccg atgcatcacc atcaccatca catgagcatt gaccgtacct c         51

<210> SEQ ID NO 7
<211> LENGTH: 59
<212> TYPE: DNA
<213> ORGANISM: Artificial Sequence
<220> FEATURE:
<223> OTHER INFORMATION: synthetic construct; FlgM primer

<400> SEQUENCE: 7
ccgttgcagc agttctggcc ctgaaaatac aggttttctt tactctgtaa gtagctctg   59

<210> SEQ ID NO 8
<211> LENGTH: 30
<212> TYPE: DNA
<213> ORGANISM: Artificial Sequence
<220> FEATURE:
<223> OTHER INFORMATION: synthetic construct; SIIIA primer

<400> SEQUENCE: 8
ttttcagggc cagaactgct gcaacggcgg                                30

<210> SEQ ID NO 9
<211> LENGTH: 28
<212> TYPE: DNA
<213> ORGANISM: Artificial Sequence
<220> FEATURE:
<223> OTHER INFORMATION: synthetic construct; SIIIA primer

<400> SEQUENCE: 9
ggaattcctt agcggccgca gcagcgcg                                  28

<210> SEQ ID NO 10
<211> LENGTH: 60
<212> TYPE: DNA
<213> ORGANISM: Artificial Sequence
<220> FEATURE:
<223> OTHER INFORMATION: synthetic construct; FlgM primer

<400> SEQUENCE: 10
actcgctcat tcgcgaggcg cagagctact tacagagtaa aggcagctct caccaccacc   60

<210> SEQ ID NO 11
<211> LENGTH: 60
<212> TYPE: DNA
<213> ORGANISM: Artificial Sequence
<220> FEATURE:
<223> OTHER INFORMATION: synthetic construct; FlgM primer

<400> SEQUENCE: 11
ttcatcaacg cgccccccat gggacgcgtt tttagaggca ttaacggtta cctgcacaag   60

<210> SEQ ID NO 12
<211> LENGTH: 30
<212> TYPE: DNA
<213> ORGANISM: Artificial Sequence
<220> FEATURE:
<223> OTHER INFORMATION: synthetic construct; FlgM primer

<400> SEQUENCE: 12
cgggatcccg atgagcattg accgtacctc                                30

<210> SEQ ID NO 13
<211> LENGTH: 60
<212> TYPE: DNA
<213> ORGANISM: Artificial Sequence
<220> FEATURE:
<223> OTHER INFORMATION: synthetic construct; FlgM primer

<400> SEQUENCE: 13
ccgttgcagc agttctggcc ctgaaaatac aggttttctt tactctgtaa gtagctctgc   60

<210> SEQ ID NO 14
<211> LENGTH: 26
<212> TYPE: DNA
<213> ORGANISM: Artificial Sequence
<220> FEATURE:
<223> OTHER INFORMATION: synthetic construct; SIIIA primer

<400> SEQUENCE: 14
ttcagggcca gaactgctgc aacggc                                    26

<210> SEQ ID NO 15
<211> LENGTH: 49

<210> SEQ ID NO 15
<211> LENGTH: 49
<212> TYPE: DNA
<213> ORGANISM: Artificial Sequence
<220> FEATURE:
<223> OTHER INFORMATION: synthetic construct; SIIIA primer

<400> SEQUENCE: 15
ggaattcctt agtgatggtg atggtgatgg cggccgcagc agcgcgcat                49

<210> SEQ ID NO 16
<211> LENGTH: 60
<212> TYPE: DNA
<213> ORGANISM: Artificial Sequence
<220> FEATURE:
<223> OTHER INFORMATION: synthetic construct; FlgM primer

<400> SEQUENCE: 16
gccctgaaaa tacaggtttt cgtgatggtg atggtgatgt ttactctgta agtagctctg    60

<210> SEQ ID NO 17
<211> LENGTH: 46
<212> TYPE: DNA
<213> ORGANISM: Artificial Sequence
<220> FEATURE:
<223> OTHER INFORMATION: synthetic construct; SIIIA primer

<400> SEQUENCE: 17
tcacgaaaac ctgtattttc agggccagaa ctgctgcaac ggcggc                   46

<210> SEQ ID NO 18
<211> LENGTH: 28
<212> TYPE: DNA
<213> ORGANISM: Artificial Sequence
<220> FEATURE:
<223> OTHER INFORMATION: synthetic construct; SIIIA primer

<400> SEQUENCE: 18
ggaattcctt agcggccgca gcagcgcg                                       28

<210> SEQ ID NO 19
<211> LENGTH: 60
<212> TYPE: DNA
<213> ORGANISM: Artificial Sequence
<220> FEATURE:
<223> OTHER INFORMATION: synthetic construct; MVIIA primer

<400> SEQUENCE: 19
tgcaaaggta aagtgcaaaa atgtagccgt ctgatgtatg attgttgtac cggtagctgt    60

<210> SEQ ID NO 20
<211> LENGTH: 38
<212> TYPE: DNA
<213> ORGANISM: Artificial Sequence
<220> FEATURE:
<223> OTHER INFORMATION: synthetic construct; MVIIA primer

<400> SEQUENCE: 20
ttaacattta ccgctacgac agctaccggt acaacaat                            38

<210> SEQ ID NO 21
<211> LENGTH: 60
<212> TYPE: DNA
<213> ORGANISM: Artificial Sequence
<220> FEATURE:
<223> OTHER INFORMATION: synthetic construct; MVIIA primer

<400> SEQUENCE: 21
acatcaccat caccatcacg aaaacctgta ttttcagggc tgcaaaggta aaggtgcaaa    60

<210> SEQ ID NO 22
<211> LENGTH: 60
<212> TYPE: DNA
<213> ORGANISM: Artificial Sequence
<220> FEATURE:
<223> OTHER INFORMATION: synthetic construct; MVIIA primer

<400> SEQUENCE: 22
ttcatcaacg cgcccccat gggacgcgtt tttagaggca ttaacattta ccgctacgac    60

<210> SEQ ID NO 23
<211> LENGTH: 60
<212> TYPE: DNA
<213> ORGANISM: Artificial Sequence
<220> FEATURE:
<223> OTHER INFORMATION: synthetic construct; GVIA primer

<400> SEQUENCE: 23
tgtaaaagtc cgggtagcag ctgtagcccg accagctata attgttgtcg tagctgtaat    60

<210> SEQ ID NO 24
<211> LENGTH: 44
<212> TYPE: DNA
<213> ORGANISM: Artificial Sequence
<220> FEATURE:
<223> OTHER INFORMATION: synthetic construct; GVIA primer

<400> SEQUENCE: 24
ttaatagcaa cgtttggtat acggattaca gctacgacaa caat    44

<210> SEQ ID NO 25
<211> LENGTH: 60
<212> TYPE: DNA
<213> ORGANISM: Artificial Sequence
<220> FEATURE:
<223> OTHER INFORMATION: synthetic construct; GVIA primer

<400> SEQUENCE: 25
acatcaccat caccatcacg aaaacctgta ttttcagggc tgtaaaagtc cgggtagcag    60

<210> SEQ ID NO 26
<211> LENGTH: 60
<212> TYPE: DNA
<213> ORGANISM: Artificial Sequence
<220> FEATURE:
<223> OTHER INFORMATION: synthetic construct; GVIA primer

<400> SEQUENCE: 26
ttcatcaacg cgcccccat gggacgcgtt tttagaggca ttaatagcaa cgtttggtat    60

<210> SEQ ID NO 27
<211> LENGTH: 51
<212> TYPE: DNA
<213> ORGANISM: Artificial Sequence
<220> FEATURE:
<223> OTHER INFORMATION: synthetic construct; contulakin primer

<400> SEQUENCE: 27
gaaagcgaag aaggtggtag caacgcaacc aaaaaaccgt atattctgta a    51

<210> SEQ ID NO 28
<211> LENGTH: 51
<212> TYPE: DNA
<213> ORGANISM: Artificial Sequence
<220> FEATURE:
<223> OTHER INFORMATION: synthetic construct; contulakin primer

<400> SEQUENCE: 28
ttacagaata tacggttttt tggttgcgtt gctaccacct tcttcgcttt c 51

<210> SEQ ID NO 29
<211> LENGTH: 60
<212> TYPE: DNA
<213> ORGANISM: Artificial Sequence
<220> FEATURE:
<223> OTHER INFORMATION: synthetic construct; contulakin primer

<400> SEQUENCE: 29
acatcaccat caccatcacg aaaacctgta ttttcagggc gaaagcgaag aaggtggtag 60

<210> SEQ ID NO 30
<211> LENGTH: 60
<212> TYPE: DNA
<213> ORGANISM: Artificial Sequence
<220> FEATURE:
<223> OTHER INFORMATION: synthetic construct; contulakin primer

<400> SEQUENCE: 30
ttcatcaacg cgccccccat gggacgcgtt tttagaggca ttacagaata tacggttttt 60

<210> SEQ ID NO 31
<211> LENGTH: 48
<212> TYPE: DNA
<213> ORGANISM: Artificial Sequence
<220> FEATURE:
<223> OTHER INFORMATION: synthetic construct; alpha Vc1.1 primer

<400> SEQUENCE: 31
tgttgtagcg atccgcgttg taattatgat catccggaaa tttgctaa 48

<210> SEQ ID NO 32
<211> LENGTH: 48
<212> TYPE: DNA
<213> ORGANISM: Artificial Sequence
<220> FEATURE:
<223> OTHER INFORMATION: synthetic construct; alpha Vc1.1 primer

<400> SEQUENCE: 32
ttagcaaatt tccggatgat cataattaca acgcggatcg ctacaaca 48

<210> SEQ ID NO 33
<211> LENGTH: 60
<212> TYPE: DNA
<213> ORGANISM: Artificial Sequence
<220> FEATURE:
<223> OTHER INFORMATION: synthetic construct; alpha Vc1.1 primer

<400> SEQUENCE: 33
acatcaccat caccatcacg aaaacctgta ttttcagggc tgttgtagcg atccgcgttg 60

<210> SEQ ID NO 34
<211> LENGTH: 60
<212> TYPE: DNA
<213> ORGANISM: Artificial Sequence
<220> FEATURE:
<223> OTHER INFORMATION: synthetic construct; alpha Vc1.1 primer

<400> SEQUENCE: 34
ttcatcaacg cgccccccat gggacgcgtt tttagaggca ttagcaaatt tccggatgat 60

<210> SEQ ID NO 35
<211> LENGTH: 60
<212> TYPE: DNA
<213> ORGANISM: Artificial Sequence
<220> FEATURE:
<223> OTHER INFORMATION: synthetic construct; GsMTx4 primer

<400> SEQUENCE: 35
tgtctggaat tttggtggaa atgcaatccg aacgatgata aatgttgtcg tccgaaactg    60

<210> SEQ ID NO 36
<211> LENGTH: 60
<212> TYPE: DNA
<213> ORGANISM: Artificial Sequence
<220> FEATURE:
<223> OTHER INFORMATION: synthetic construct; GsMTx4 primer

<400> SEQUENCE: 36
accgctgcta aaattgcaca gtttaaacag tttgctgcat tcagtttcg gacgacaaca    60

<210> SEQ ID NO 37
<211> LENGTH: 60
<212> TYPE: DNA
<213> ORGANISM: Artificial Sequence
<220> FEATURE:
<223> OTHER INFORMATION: synthetic construct; GsMTx4 primer

<400> SEQUENCE: 37
acatcaccat caccatcacg aaaacctgta ttttcagggc tgtctggaat tttggtggaa    60

<210> SEQ ID NO 38
<211> LENGTH: 60
<212> TYPE: DNA
<213> ORGANISM: Artificial Sequence
<220> FEATURE:
<223> OTHER INFORMATION: synthetic construct; GsMTx4 primer

<400> SEQUENCE: 38
atcaacgcgc cccccatggg acgcgttttt agaggcatta accgctgcta aaattgcaca    60

<210> SEQ ID NO 39
<211> LENGTH: 60
<212> TYPE: DNA
<213> ORGANISM: Artificial Sequence
<220> FEATURE:
<223> OTHER INFORMATION: synthetic construct; Calciseptine primer

<400> SEQUENCE: 39
cgcatctgct atattcataa agcaagcctg cctcgtgcaa ccaaaacctg tgttgaaaat    60

<210> SEQ ID NO 40
<211> LENGTH: 60
<212> TYPE: DNA
<213> ORGANISM: Artificial Sequence
<220> FEATURE:
<223> OTHER INFORMATION: synthetic construct; Calciseptine primer

<400> SEQUENCE: 40
tatattcgcg ctgggtacga ataaacattt tatagcaggt attttcaaca caggttttgg    60

<210> SEQ ID NO 41
<211> LENGTH: 60
<212> TYPE: DNA
<213> ORGANISM: Artificial Sequence
<220> FEATURE:
<223> OTHER INFORMATION: synthetic construct; Calciseptine primer

<400> SEQUENCE: 41
tcgtacccag cgcgaatata tcagcgaacg tggttgtggt tgtccgaccg caatgtggcc        60

<210> SEQ ID NO 42
<211> LENGTH: 60
<212> TYPE: DNA
<213> ORGANISM: Artificial Sequence
<220> FEATURE:
<223> OTHER INFORMATION: synthetic construct; Calciseptine primer

<400> SEQUENCE: 42
tttgttgcaa cgatcacctt tacaacattc ggtctgatac ggccacattg cggtcggaca        60

<210> SEQ ID NO 43
<211> LENGTH: 60
<212> TYPE: DNA
<213> ORGANISM: Artificial Sequence
<220> FEATURE:
<223> OTHER INFORMATION: synthetic construct; Calciseptine primer

<400> SEQUENCE: 43
acatcaccat caccatcacg aaaacctgta ttttcagggc cgcatctgct atattcataa        60

<210> SEQ ID NO 44
<211> LENGTH: 60
<212> TYPE: DNA
<213> ORGANISM: Artificial Sequence
<220> FEATURE:
<223> OTHER INFORMATION: synthetic construct; Calciseptine primer

<400> SEQUENCE: 44
atcaacgcgc cccccatggg acgcgttttt agaggcatta tttgttgcaa cgatcacctt        60

<210> SEQ ID NO 45
<211> LENGTH: 54
<212> TYPE: DNA
<213> ORGANISM: Artificial Sequence
<220> FEATURE:
<223> OTHER INFORMATION: synthetic construct; Conantokin primer

<400> SEQUENCE: 45
ggtgaagaag aactgcaaga aaaccaagaa ctgattcgcg aaaaaagcaa ttaa              54

<210> SEQ ID NO 46
<211> LENGTH: 54
<212> TYPE: DNA
<213> ORGANISM: Artificial Sequence
<220> FEATURE:
<223> OTHER INFORMATION: synthetic construct; Conantokin primer

<400> SEQUENCE: 46
ttaattgctt ttttcgcgaa tcagttcttg gttttcttgc agttcttctt cacc              54

<210> SEQ ID NO 47
<211> LENGTH: 60
<212> TYPE: DNA
<213> ORGANISM: Artificial Sequence
<220> FEATURE:
<223> OTHER INFORMATION: synthetic construct; Conantokin primer

<400> SEQUENCE: 47
acatcaccat caccatcacg aaaacctgta ttttcagggc ggtgaagaag aactgcaaga        60

<210> SEQ ID NO 48

<211> LENGTH: 60
<212> TYPE: DNA
<213> ORGANISM: Artificial Sequence
<220> FEATURE:
<223> OTHER INFORMATION: synthetic construct; Conantokin primer

<400> SEQUENCE: 48
ttcatcaacg cgccccccat gggacgcgtt tttagaggca ttaattgctt ttttcgcgaa 60

<210> SEQ ID NO 49
<211> LENGTH: 60
<212> TYPE: DNA
<213> ORGANISM: Artificial Sequence
<220> FEATURE:
<223> OTHER INFORMATION: synthetic construct; SIIIA primer

<400> SEQUENCE: 49
gaaaattgct gtaatggtgg ttgtagcagc aaatggtgtc gtgatcatgc acgttgttgt 60

<210> SEQ ID NO 50
<211> LENGTH: 60
<212> TYPE: DNA
<213> ORGANISM: Artificial Sequence
<220> FEATURE:
<223> OTHER INFORMATION: synthetic construct; SIIIA primer

<400> SEQUENCE: 50
ttaacaacaa cgtgcatgat cacgacacca tttgctgcta caaccaccat tacagcaatt 60

<210> SEQ ID NO 51
<211> LENGTH: 60
<212> TYPE: DNA
<213> ORGANISM: Artificial Sequence
<220> FEATURE:
<223> OTHER INFORMATION: synthetic construct; SIIIA primer

<400> SEQUENCE: 51
acatcaccat caccatcacg aaaacctgta ttttcagggc gaaaattgct gtaatggtgg 60

<210> SEQ ID NO 52
<211> LENGTH: 60
<212> TYPE: DNA
<213> ORGANISM: Artificial Sequence
<220> FEATURE:
<223> OTHER INFORMATION: synthetic construct; SIIIA primer

<400> SEQUENCE: 52
ttcatcaacg cgccccccat gggacgcgtt tttagaggca ttaacaacaa cgtgcatgat 60

<210> SEQ ID NO 53
<211> LENGTH: 60
<212> TYPE: DNA
<213> ORGANISM: Artificial Sequence
<220> FEATURE:
<223> OTHER INFORMATION: synthetic construct; Shk primer

<400> SEQUENCE: 53
agctgcattg ataccattcc gaaaagccgt tgtaccgcat ttcagtgtaa acacagcatg 60

<210> SEQ ID NO 54
<211> LENGTH: 60
<212> TYPE: DNA
<213> ORGANISM: Artificial Sequence
<220> FEATURE:
<223> OTHER INFORMATION: synthetic construct; Shk primer

<400> SEQUENCE: 54

-continued acaggtgcca caggttttac gacaaaagct cagacgatat tcatgctgt gtttacactg    60

<210> SEQ ID NO 55
<211> LENGTH: 60
<212> TYPE: DNA
<213> ORGANISM: Artificial Sequence
<220> FEATURE:
<223> OTHER INFORMATION: synthetic construct; Shk primer

<400> SEQUENCE: 55
atcaccatca ccatcacgaa aacctgtatt ttcagggccg tagctgcatt gataccattc    60

<210> SEQ ID NO 56
<211> LENGTH: 60
<212> TYPE: DNA
<213> ORGANISM: Artificial Sequence
<220> FEATURE:
<223> OTHER INFORMATION: synthetic construct; Shk primer

<400> SEQUENCE: 56
catcaacgcg cccccatgg gacgcgtttt tagaggcatt aacaggtgcc acaggtttta    60

<210> SEQ ID NO 57
<211> LENGTH: 60
<212> TYPE: DNA
<213> ORGANISM: Artificial Sequence
<220> FEATURE:
<223> OTHER INFORMATION: synthetic construct; Chlorotoxin primer

<400> SEQUENCE: 57
atgtgtatgc cgtgttttac caccgatcat cagatggcac gtaaatgtga tgattgttgt    60

<210> SEQ ID NO 58
<211> LENGTH: 60
<212> TYPE: DNA
<213> ORGANISM: Artificial Sequence
<220> FEATURE:
<223> OTHER INFORMATION: synthetic construct; Chlorotoxin primer

<400> SEQUENCE: 58
gacactgcgg accataacat ttaccgcgac ctttaccacc acaacaatca tcacatttac    60

<210> SEQ ID NO 59
<211> LENGTH: 31
<212> TYPE: DNA
<213> ORGANISM: Artificial Sequence
<220> FEATURE:
<223> OTHER INFORMATION: synthetic construct; Chlorotoxin primer

<400> SEQUENCE: 59
ttaacgacac agacactgcg gaccataaca t    31

<210> SEQ ID NO 60
<211> LENGTH: 60
<212> TYPE: DNA
<213> ORGANISM: Artificial Sequence
<220> FEATURE:
<223> OTHER INFORMATION: synthetic construct; Chlorotoxin primer

<400> SEQUENCE: 60
acatcaccat caccatcacg aaaacctgta ttttcagggc atgtgtatgc cgtgttttac    60

<210> SEQ ID NO 61
<211> LENGTH: 60
<212> TYPE: DNA

```
<213> ORGANISM: Artificial Sequence
<220> FEATURE:
<223> OTHER INFORMATION: synthetic construct; Chlorotoxin primer

<400> SEQUENCE: 61
ttcatcaacg cgccccccat gggacgcgtt tttagaggca ttaacgacac agacactgcg        60

<210> SEQ ID NO 62
<211> LENGTH: 25
<212> TYPE: PRT
<213> ORGANISM: Conus magus

<400> SEQUENCE: 62

Cys Lys Gly Lys Gly Ala Lys Cys Ser Arg Leu Met Tyr Asp Cys Cys
1               5                   10                  15

Thr Gly Ser Cys Arg Ser Gly Lys Cys
            20                  25

<210> SEQ ID NO 63
<211> LENGTH: 27
<212> TYPE: PRT
<213> ORGANISM: Conus geographus

<400> SEQUENCE: 63

Cys Lys Ser Pro Gly Ser Ser Cys Ser Pro Thr Ser Tyr Asn Cys Cys
1               5                   10                  15

Arg Ser Cys Asn Pro Tyr Thr Lys Arg Cys Tyr
            20                  25

<210> SEQ ID NO 64
<211> LENGTH: 16
<212> TYPE: PRT
<213> ORGANISM: Conus geographus

<400> SEQUENCE: 64

Glu Ser Glu Glu Gly Gly Ser Asn Ala Thr Lys Lys Pro Tyr Ile Leu
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: synthetic construct; conus victoriae alpha
      Vc1.1

<400> SEQUENCE: 65

Gly Cys Cys Ser Asp Pro Arg Cys Asn Tyr Asp His Pro Glu Ile Cys
1               5                   10                  15

<210> SEQ ID NO 66
<211> LENGTH: 17
<212> TYPE: PRT
<213> ORGANISM: Conus geographus

<400> SEQUENCE: 66

Gly Glu Glu Glu Leu Gln Glu Asn Gln Glu Leu Ile Arg Glu Lys Ser
1               5                   10                  15

Asn

<210> SEQ ID NO 67
<211> LENGTH: 20
<212> TYPE: PRT
<213> ORGANISM: Conus striatus
```

<400> SEQUENCE: 67

Glu Asn Cys Cys Asn Gly Gly Cys Ser Ser Lys Trp Cys Arg Asp His
1               5                   10                  15

Ala Arg Cys Cys
            20

<210> SEQ ID NO 68
<211> LENGTH: 22
<212> TYPE: PRT
<213> ORGANISM: Conus striatus

<400> SEQUENCE: 68

Gln Asn Cys Cys Asn Gly Gly Cys Ser Ser Lys Trp Cys Arg Asp His
1               5                   10                  15

Ala Arg Cys Cys Gly Arg
            20

<210> SEQ ID NO 69
<211> LENGTH: 35
<212> TYPE: PRT
<213> ORGANISM: Stichodactyla helianthus

<400> SEQUENCE: 69

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 70
<211> LENGTH: 36
<212> TYPE: PRT
<213> ORGANISM: Leiurus quinquestriatus

<400> SEQUENCE: 70

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 71
<211> LENGTH: 35
<212> TYPE: PRT
<213> ORGANISM: Grammostola spatulata

<400> SEQUENCE: 71

Gly Cys Leu Glu Phe Trp Trp Lys Cys Asn Pro Asn Asp Asp Lys Cys
1               5                   10                  15

Cys Arg Pro Lys Leu Lys Cys Ser Lys Leu Phe Lys Leu Cys Asn Phe
            20                  25                  30

Ser Ser Gly
        35

<210> SEQ ID NO 72
<211> LENGTH: 60
<212> TYPE: PRT
<213> ORGANISM: Dendroaspis polylepis

```
<400> SEQUENCE: 72

Arg Ile Cys Tyr Ile His Lys Ala Ser Leu Pro Arg Ala Thr Lys Thr
1               5                   10                  15

Cys Val Glu Asn Thr Cys Tyr Lys Met Phe Ile Arg Thr Gln Arg Glu
            20                  25                  30

Tyr Ile Ser Glu Arg Gly Cys Gly Cys Pro Thr Ala Met Trp Pro Tyr
        35                  40                  45

Gln Thr Glu Cys Cys Lys Gly Asp Arg Cys Asn Lys
    50                  55                  60

<210> SEQ ID NO 73
<211> LENGTH: 190
<212> TYPE: PRT
<213> ORGANISM: Corynebacterium diphtheriae

<400> SEQUENCE: 73

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Ala Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg
            180                 185                 190

<210> SEQ ID NO 74
<211> LENGTH: 31
<212> TYPE: PRT
<213> ORGANISM: Artificial Sequence
<220> FEATURE:
<223> OTHER INFORMATION: synthetic construct; peptide from marine cone
      snails

<400> SEQUENCE: 74

Asp Gly Cys Ser Ser Gly Gly Thr Phe Cys Gly Ile His Pro Gly Leu
1               5                   10                  15

Cys Cys Ser Glu Phe Cys Phe Leu Trp Cys Ile Thr Phe Ile Asp
            20                  25                  30
```